US009732357B2

(12) United States Patent
Deshpande et al.

(10) Patent No.: US 9,732,357 B2
(45) Date of Patent: Aug. 15, 2017

(54) EFFICIENT SELECTIVITY OF RECOMBINANT PROTEINS

(71) Applicant: REGENERON PHARMACEUTICALS, INC., Tarrytown, NY (US)

(72) Inventors: Dipali Deshpande, White Plains, NY (US); Darya Burakov, Yonkers, NY (US); Gang Chen, Yorktown Heights, NY (US); James Fandl, LaGrangeville, NY (US)

(73) Assignee: REGENERON PHARMACEUTICALS, Tarrytown, NY (US)

( * ) Notice: Subject to any disclaimer, the term of this patent is extended or adjusted under 35 U.S.C. 154(b) by 13 days.

(21) Appl. No.: 14/829,834

(22) Filed: Aug. 19, 2015

(65) Prior Publication Data
US 2016/0053280 A1 Feb. 25, 2016

Related U.S. Application Data
(60) Provisional application No. 62/039,416, filed on Aug. 19, 2014.

(51) Int. Cl.
C12N 15/52 (2006.01)
C12Q 1/48 (2006.01)
C12N 15/85 (2006.01)
C12P 21/00 (2006.01)

(52) U.S. Cl.
CPC ............ *C12N 15/85* (2013.01); *C12P 21/005* (2013.01); *C07K 2319/30* (2013.01)

(58) Field of Classification Search
CPC  C12Y 207/08015; C12N 15/52; C12N 21/05; C12Q 1/48
See application file for complete search history.

(56) References Cited

U.S. PATENT DOCUMENTS

| | | | |
|---|---|---|---|
| 4,634,665 A | 1/1987 | Axel et al. | |
| 4,656,134 A | 4/1987 | Ringold | |
| 5,589,466 A | 12/1996 | Felgner et al. | |
| 5,972,650 A | 10/1999 | Yao | |
| 5,973,972 A | 10/1999 | Kwon et al. | |
| 6,077,835 A | 6/2000 | Hanson et al. | |
| 7,192,737 B2 | 3/2007 | Horwitz | |
| 7,384,744 B2 | 6/2008 | Enenkel et al. | |
| 7,435,553 B2 | 10/2008 | Fandl et al. | |
| 2009/0117618 A1* | 5/2009 | Herrmann | C07K 14/5443 435/69.52 |
| 2009/0162900 A1 | 6/2009 | Enenkel et al. | |
| 2009/0162901 A1 | 6/2009 | Chen et al. | |
| 2010/0291626 A1 | 11/2010 | Chen et al. | |
| 2011/0091495 A1* | 4/2011 | Marcotrigiano | A61K 39/29 424/189.1 |
| 2011/0107455 A1 | 5/2011 | Lira et al. | |

FOREIGN PATENT DOCUMENTS

WO  WO 00/70087 A1  11/2000
WO  WO 2009/066919 A2  5/2009
WO  WO 2013/186371 A1  12/2013

OTHER PUBLICATIONS

Eckert et al. 1998; Cloning and functional expression of the human GlcNAc-1-P transferase, the enzyme for the committed step of the dolichol cycle, by heterologous complementation in Saccharamyces cerevisiae. Glycobiology. 8(1): 77-85.*
International Search Report and Written Opinion dated Jan. 28, 2016 received in International Application No. PCT/US15/45793.
GenBank Accession No. M55621.1 (Nov. 8, 1994) (2 pages total).
Kumar R. et al., "Cloning and Expression of N-Acetylglucosaminyltransferase I, the Medial Golgi Transferase that Initiates Complex N-Linked Carbohydrate Formation", Proc. Natl. Acad. Sci. USA 87:9948-9952 (Dec. 1990).
International Preliminary Report on Patentability and Annex dated Aug. 25, 2016 received in International Application No. PCT/US15/45793.
Araki K. et al., "Site-Directed Integration of the Cre Gene Mediated by Cre Recombinase Using a Combination of Mutant Lox Sites", Nucleic Acids Research 30(19):e103 (2002).
Araki K. et al., "Site-Specific Recombination of a Transgene in Fertilized Eggs by Transient Expression of Cre Recombinase", Proc. Natl. Acad. Sci. USA 92:160-164 (Jan. 1995).
Bitter G.A. et al., "Expression and Secretion Vectors for Yeast", Methods in Enzymology 153:516-544 (1987).
Boch J. et al., "Breaking the Code of DNA Binding Specificity of TAL-Type III Effectors", Science 326:1509-1512 (Dec. 11, 2009).
Bork K. et al., "Increasing the Sialylation of Therapeutic Glycoproteins: The Potential of the Sialic Acid Biosynthetic Pathway", Journal of Pharmaceutical Sciences 98(10):3499-3508 (Oct. 2009).
Breyer D. et al., "Alternatives to Antibiotic Resistance Marker Genes for In Vitro Selection of Genetically Modified Plants-Scientific Developments, Current Use, Operational Access and Biosafety Considerations", Critical Reviews in Plant Sciences 33:286-330 (2014).
Chen H. et al., "Cut Site Selection by the Two Nuclease Domains of the Cas9 RNA-Guided Endonuclease", The Journal of Biological Chemistry 289(19):13284-13294 (May 9, 2014).
Crick D.C. et al., "Induction of Dolichyl-Saccharide Intermediate Biosynthesis Corresponds to Increased Long Chain Cis-Isoprenyltransferase Activity During the Mitogenic Response in Mouse B Cells", The Journal of Biological Chemistry 269(14):10559-10565 (Apr. 8, 1994).

(Continued)

*Primary Examiner* — Karen Cochrane Carlson
(74) *Attorney, Agent, or Firm* — Scully, Scott, Murphy & Presser, P.C.

(57) ABSTRACT

The invention provides a new expression system comprising a mammalian selectable marker that promotes desirable post-translational modifications of glycoproteins. In particular, the invention includes methods and compositions for optimal recombinant protein expression in mammalian cells by employing a selection marker system based on GPT genes of mammalian origin. The invention includes methods that facilitate selectivity and enhanced expression copies as well as protein yield of recombinant proteins in mammalian cells, and methods of using GPT expression systems.

41 Claims, 17 Drawing Sheets

(56) References Cited

OTHER PUBLICATIONS

Cumming D.A., "Glycosylation of Recombinant Protein Therapeutics: Control and Functional Implications", Glycobiology 1(2):115-130 (1991).
Dal Nogare A.R. et al., "Conserved Sequences in Enzymes of the UDP-GlcNAc/MurNAc Family are Essential in Hamster UDP-GlcNAc:Dolichol-P GlcNAc-1-P Transferase", Glycobiology 8(6):625-632 (1998).
Dan N. et al., "Hamster UDP-N-Acetylglucosamine:Dolichol-P N-Acetylglucosamine-1-P Transferase Has Multiple Transmembrane Spans and a Critical Cytosolic Loop", The Journal of Biological Chemistry 271(48):30717-30724 (Nov. 29, 1996).
Duong C.P.M. et al., "Cancer Immunotherapy Utilizing Gene-Modified T Cells: From the Bench to the Clinic", Molecular Immunology 67(2 Pt A):46-57 (Oct. 2015).
Dymecki S.M., "Flp Recombinase Promotes Site-Specific DNA Recombination in Embryonic Stem Cells and Transgenic Mice", Proc. Natl. Acad. Sci. USA 93:6191-6196 (Jun. 1996).
Eaker S. et al., "Concise Review: Guidance in Developing Commercializable Autologous/Patient-Specific Cell Therapy Manufacturing", Stem Cells Translational Medicine 2:871-883 (2013).
Feil R. et al., "Regulation of Cre Recombinase Activity by Mutated Estrogen Receptor Ligand-Binding Domains", Biochemical and Biophysical Research Communications 237:752-757 (1997).
Fiers W. et al., "Complete Nucleotide Sequence of SV40 DNA", Nature 273(5658):113-120 (May 11, 1978).
Gossen M. et al., "Tight Control of Gene Expression in Mammalian Cells by Tetracycline-Responsive Promoters", Proc. Natl. Acad. Sci. USA 89:5547-5551 (Jun. 1992).
Kaufman R.J., "Selection and Coamplification of Heterologous Genes in Mammalian Cells", Methods in Enzymology 185:537-566 (1990).
Kershaw M.H. et al., "Gene-Engineered T Cells for Cancer Therapy", Nature Reviews-Cancer 13:525:541 (Aug. 2013).
Kim H-S et al., "The UDP-N-Acetylglucosamine:Dolichol Phosphate-N-Acetylglucosamine-Phosphotransferase Gene as a New Selection Marker for Potato Transformation", Biosci. Biotechnol. Biochem. 77(7):1589-1592 (2013).
Kim S.K. et al., "Stable Reduction of Thymidine Kinase Activity in Cells Expressing High Levels of Anti-Sense RNA", Cell 42:129-138 (Aug. 1985).
King I.A. et al., "Effect of Tunicamycin on Epidermal Glycoprotein and Glycosaminoglycan Synthesis In Vitro", Biochem. J. 198:331-338 (1981).
Koizumi N. et al., "Overexpression of a Gene that Encodes the First Enzyme in the Biosynthesis of Asparagine-Linked Glycans Makes Plants Resistant to Tunicamycin and Obviates the Tunicamycin-Induced Unfolded Protein Response", Plant Physiology 121:353-361 (Oct. 1999).
Lehrman M.A. et al., "Amplification and Molecular Cloning of the Hamster Tunicamycin-Sensitive N-Acetylglucosamine-1-Phosphate Transferase Gene", The Journal of Biological Chemistry 263(36):19796-19803 (Dec. 25, 1988).
Lupton S.D. et al., "Dominant Positive and Negative Selection Using a Hygromycin Phosphotransferase-Thymidine Kinase Fusion Gene", Molecular and Cellular Biology 11(6):3374-3378 (Jun. 1991).
McLachlan K.R. et al., "Substrate Specificity of N-Acetylglucosamine 1-Phosphate Transferase Activity in Chinese Hamster Ovary Cells", Glycobiology 2(4):313-319 (1992).
Nadanaka S. et al., "Activation of Mammalian Unfolded Protein Response is Compatible With the Quality Control System Operating in the Endoplasmic Reticulum", Molecular Biology of the Cell 15:2537-2548 (Jun. 2004).
Nagy A., "Cre Recombinase: The Universal Reagent for Genome Tailoring", Genesis 26:99-109 (2000).
Ron D. et al., "Signal Integration in the Endoplasmic Reticulum Unfolded Protein Response", Nature Reviews—Molecular Cell Biology 8:519-529 (Jul. 2007).
Scocca J.R. et al., "Sequence of a cDNA that Specifies the Uridine Diphosphate N-Acetyl-D-Glucosamine: Dolichol Phosphate N-Acetylglucosamine-1-Phosphate Transferase from Chinese Hamster Ovary Cells", The Journal of Biological Chemistry 265(33):20621-20626 (Nov. 25, 1990).
Scocca J.R. et al., "Evidence of Gene Amplification in Tunicamycin-Resistant Chinese Hamster Ovary Cells", Biochemical and Biophysical Research Communications 156(3):1063-1069 (Nov. 15, 1988).
Scocca J.R. et al., "Genomic Organization and Expression of Hamster UDP-N-Acetylglucosamine:Dolichyl Phosphate N-Acetylglucosaminyl Phosphoryl Transferase", Glycobiology 5(1):129-136 (1995).
Stella S. et al., "BuD, a Helix-Loop-Helix DNA-Binding Domain for Genome Modification", Acta Crystallographica D70:2042-2052 (2014).
Sykes K.F. et al., "Linear Expression Elements: A Rapid, In Vivo, Method to Screen for Gene Functions", Nature Biotechnology 17:355-359 (Apr. 1999).
Tanaka Y. et al., "Development of Gateway Binary Vectors R4L1pGWB Possessing the Bialaphos Resistance Gene (bar) and the Tunicamycin Resistance Gene as Markers for Promoter Analysis in Plants", Biosci. Biotechnol. Biochem. 77(8):1795-1797 (2013).
Tanaka Y. et al., "Development of a Series of Gateway Binary Vectors Possessing a Tunicamycin Resistance Gene as a Marker for the Transformation of Arabidopsis Thaliana", Biosci. Biotechnol. Biochem. 75(4):804-807 (2011).
Waldman B.C. et al., "A Clonal Derivative of Tunicamycin-Resistant Chinese Hamster Ovary Cells With Increased N-Acetylglucosamine-Phosphate Transferase Activity Has Altered Asparagine-Linked Glycosylation", Journal of Cellular Physiology 131:302-317 (1987).
GenBank Accession No. M36899.1 (1990) (2 pages total).
GenBank Accession No. D88037.1 (1999) (2 pages total).

* cited by examiner

```
       ****  *.;*.    ***.;**.     **********************.;*********.  ;.********
  1    MWAFSELP---MPLLINLIVSLLGFVATVTLIPAFRGHFIAARLCGQDLNKTSRQQIPESQ        58    GPT_HUMAN
  1    MWAFSELP---MPLLLVNLIVSLLGFVATVTLIPAFRGHFIAARLCGQDLNKTSRQQIPESQ       58    GPT_MACMU
  1    MWAFSELP---MPLLINLIVSLLGFVATVTLIPAFRGHFIAARLCGQDLNKTSRQQIPESQ        58    GPT_PANTR
  1    MWAFPELP---MPLLVNLVGSLLGFVATVTLIPAFRGHFIAAHLCGQDLNKTGRQQIPESQ        58    GPT_CANFA
  1    MWAFSEVP---IPLLVNLIGSLLGFVATLTLIPAFRGHFIAARLCGQDLNKTNRQQIPESQ        58    GPT_CAVPO
  1    MWAFPELPLPLPLLVNLIGSLLGFVATVTLIPAFRSHFIAARLCGQDLNKLSRQQIPESQ         60    GPT_RAT
  1    MWAFPELPLPLPLLVNLIGSLLGFVATVTLIPAFRSHFIAARLCGQDLNKLSQQIPESQ          60    GPT_MOUSE
  1    MWAFPEIPL--PLLVNLFGSLLGFVATVTLIPAFRSHFIAARLCGQDLNKLSRQQIPESQ         58    GPT_CRIGR

***.;********************************;;***************
 59    GVISGAVFLIILFCFIPFPFFLNCFIPFPFFLNCFVKEQCKAFPHHEFVALIGALLAICCMIFLGFADDVL      118   GPT_HUMAN
 59    GVISGAVFLIILFCFIPFPFFLNCFIPFPFFLNCFVKEQCKAFPHHEFVALIGALLAICCMIFLGFADDVL      118   GPT_MACMU
 59    GVISGAVFLIILFCFIPFPFFLNCFIPFPFFLNCFVKEQCKAFPHHEFVALIGALLAICCMIFLGFADDVL      118   GPT_PANTR
 59    GVISGAVFLIILFCFIPFPFFLNCFIPFPFFLNCFMEEQCKAFPHHEFVALIGALLAICCMIFLGFADDVL      118   GPT_CANFA
 59    GVISGAVFLIILFCFIPFPFFLNCFIPFPFFLNCFVKEQCKAFPHHEFVALIGALLAICCMIFLGFADDVL      118   GPT_CAVPO
 61    GVISGAVFLIILFCFIPFPFFLNCFVEEQCKAFPHHEFVALIGALLAICCMIFLGFADDVL               120   GPT_RAT
 61    GVISGAVFLIILFCFIPFPFFLNCFVEEQCKAFPHHEFVALIGALLAICCMIFLGFADDVL               120   GPT_MOUSE
 59    GVICGAVFLIILFCFIPFPFFLNCFVREQCKAFPHHEFVALIGALLAICCMIFLGFADDVL               118   GPT_CRIGR

****************************************.;****************  ;;***********
119    NLRWRHKILLPTAASLPLIMVYFTNFGNTTIVVPKPFRPILGLHLDLGILYYVYMGLLAV                178   GPT_HUMAN
119    NLRWRHKILLPTAASLPLIMVYFTNFGNTTIVVPKPFRPILGLHLDLGILYYVYMGLLAV                178   GPT_MACMU
119    NLRWRHKILLPTAASLPLIMVYFTNFGNTTIVVPKPFRPILGLHLDLGILYYVYMGLLAV                178   GPT_PANTR
119    NLRWRHKILLPTAASLPLIMVYFTNFGNTTIVVPKPFRPTLGLHLDLGILYYVYMGLLAV                178   GPT_CANFA
119    NLRWRHKILLPTAASLPLIMVYFTNFGNTTIVVPKPFRPVLGLHLDLGILYYVYMGLLAV                178   GPT_CAVPO
121    NLRWRHKILLPTAASLPLIMVYFTNFGNTTIVVPKPFRWILGLHLDLGILYYVYMGLLAV                180   GPT_RAT
121    NLRWRHKILLPTAASLPLIMVYFTNFGNTTIVVPKPFRWILGLHLDLGILYYVYMGLLAV                180   GPT_MOUSE
119    NLRWRHKILLPTAASLPLIMVYFTNFGNTTIVVPKPFRWILGLHLDLGILYYVYMGLLAV                178   GPT_CRIGR
```

FIG. 2A

```
179  FCTNAINILAGINGLEAGQSLVISASIIVFNLVELEGDCRDDHVFSLYFMIPFFTTLGL  238  GPT_HUMAN
179  FCTNAINILAGINGLEAGQSLVISASIIVFNLVELEGDCRDDHVFSLYFMIPFFTTLGL  238  GPT_MACMU
179  FCTNAINILAGINGLEAGQSLVISASIIVFNLVELEGDCRDDHVFSLYFMIPFFTTLGL  238  GPT_PANTR
179  FCTNAINILAGINGLEAGQSLVISASIIVFNLVELEGDYRDDHVFSLYFMIPFFTTLGL  238  GPT_CANFA
179  FCTNAINILAGINGLEAGQSLVISASIIVFNLVELQGDYRDDHVFSLYFMIPFFTTLGL  238  GPT_CAVPO
179  FCTNAINILAGINGLEAGQSLVISASIIVFNLVELEGDYRDDHVFSLYFMIPFFTTLGL  238  GPT_RAT
181  FCTNAINILAGINGLEAGQSLVISASIIVFNLVELEGDYRDDHIFSLYFMPFFTTLGL   240  GPT_RAT
181  FCTNAINILAGINGLEAGQSLVISASIIVFNLVELEGDYRDDHVFSLYFMPFFTTLGL   240  GPT_MOUSE
179  FCTNAINILAGINGLEAGQSLVISASIIVFNLVELEGDYRDDHVFSLYFMIPFFTTLGL  238  GPT_CRIGR
     *********:*********************:************;;***********

239  LYHNWYPSRVFVGDTFCYFAGMTFAVVGILGHFSKTMLLFFMPQVFNFLYSLPQLLHIIP  298  GPT_HUMAN
239  LYHNWYPSRVFVGDTFCYFAGMTFAVVGILGHFSKTMLLFFMPQVFNFLYSLPQLLHIIP  298  GPT_MACMU
239  LYHNWYPSRVFVGDTFCYFAGMTFAVVGILGHFSKTMLLFFMPQVFNFLYSLPQLLHIIP  298  GPT_PANTR
239  LYHNWYPSQVFVGDTFCYFAGMTFAVVGILGHFSKTMLLFFMPQVFNFLYSLPQLLHIIP  298  GPT_CANFA
239  LYHNWYPSQVFVGDTFCYFAGMTFAVVGILGHFSKTMLLFFMPQVFNFLYSLPQLLHIIP  298  GPT_CAVPO
239  LYHNWYPSQVFVGDTFCYFAGMTFAVVGILGHFSKTMLLFFMPQVFNFLYSLPQLLHIIP  298  GPT_RAT
241  LYHNWYPSQVFVGDTFCYFAGMTFAVVGILGHFSKTMLLFFMPQVFNFLYSLPQLFHIIP  300  GPT_RAT
241  LYHNWYPSQVFVGDTFCYFAGMTFAVVGILGHFSKTMLLFFMPQVFNFLYSLPQLFHIIP  300  GPT_MOUSE
239  LYHNWYPSQVFVGDTFCYFAGMTFAVVGILGHFSKTMLLFFIPQVFNFLYSLPQLLHAIP  298  GPT_CRIGR
     ********:*****.*********************:****.*******; ********

299  CPRHRIPRLNIKTGKLEMSYSKFKTKSLSFLGTFILKVAESLQLVTVHQSETEDGEFTEC  358  GPT_HUMAN
299  CPRHRIPRLNIKTGKLEMSYSKFKTKSLSFLGTFILKVAESLRLVTIHQSDTEDGEFTEC  358  GPT_MACMU
299  CPRHRIPRLNIKTGKLEMSYSKFKTKSLSFLGTFILKVAESLRLVTIHQSDTEDGEFTEC  358  GPT_PANTR
299  CPRHRIPRLNINKTGKLEMSYSKFKTKSLSFLGTFILKVAESLQLVTVHQSETEDGAFTEC 358  GPT_CANFA
299  CPRHRIPRLNTKTGKLEMSYSKFKTKSLSFLGNFILKVAASLQLVTVHQSENEDGAFTEC  358  GPT_CAVPO
299  CPRHRIPRLNIKTGKLEMSYSKFKTNSLSFLGTFILKVAERLQLVTVHRSEGEDGAFTEC  358  GPT_RAT
301  CPRHRMPRLNIKTGKLEMSYSKFKTKSLSFLGTFILKVAESLRLVTVHRGESEDGAFTEC  360  GPT_RAT
301  CPRHRMPRLNAKTGKLEMSYSKFKTKNLSFLGTFILKVAENLRLVTVHQGESEDGAFTEC  360  GPT_MOUSE
299  CPRHRIPRLNPKTGKLEMSYSKFKTKNLSFLGTFILKVAERLQLVTVHRGESEDGAFTEC  358  GPT_CRIGR
     *****; ***** ****************:*****.******; ;; *** ****
```

FIG. 2B

```
        *****:;***** ::;**  *******:;****** ::.**  *****************
359  NNMTLINLLLLKVLGPIHERNLTLLLLLLQILGSAITFSIRYQLVRLFYDV  408  GPT_HUMAN
359  NNMTLINLLLLKIFGPIHERNLTLLLLLLQILGSAFTFSIRYQLVRLFYDV  408  GPT_MACMU
359  NNMTLINLLLLKILGPIHERNLITLLLLLLQILGSAITFSIRYQLVRLFYDV 408  GPT_PANTR
359  NNMTLLNLLLLKVLGPMHERNLTLLLLLLQILGSAVTFSIRYQLVRLFYDV  408  GPT_CANFA
359  NNMTLINLLLLKIFGPIHERNLTLLLLLLQIVGSAVTFSIRYQLVRLFYDV  408  GPT_CAVPO
361  NNMTLINLLLLKVFGPIHERNLTLFLLLLQVLSSAVTFSIRYQLVRLFYDV  410  GPT_RAT
361  NNMTLINLLLLKVFGPIHERNLITLLLLLLQVLSSAATFSIRYQLVRLFYDV 410  GPT_MOUSE
359  NNMTLINLLLLKIFGPIHERNLTLLLLLLQILSSAVTFSIRYQLVRLFYDV  408  GPT_CRIGR
```

FIG. 2C

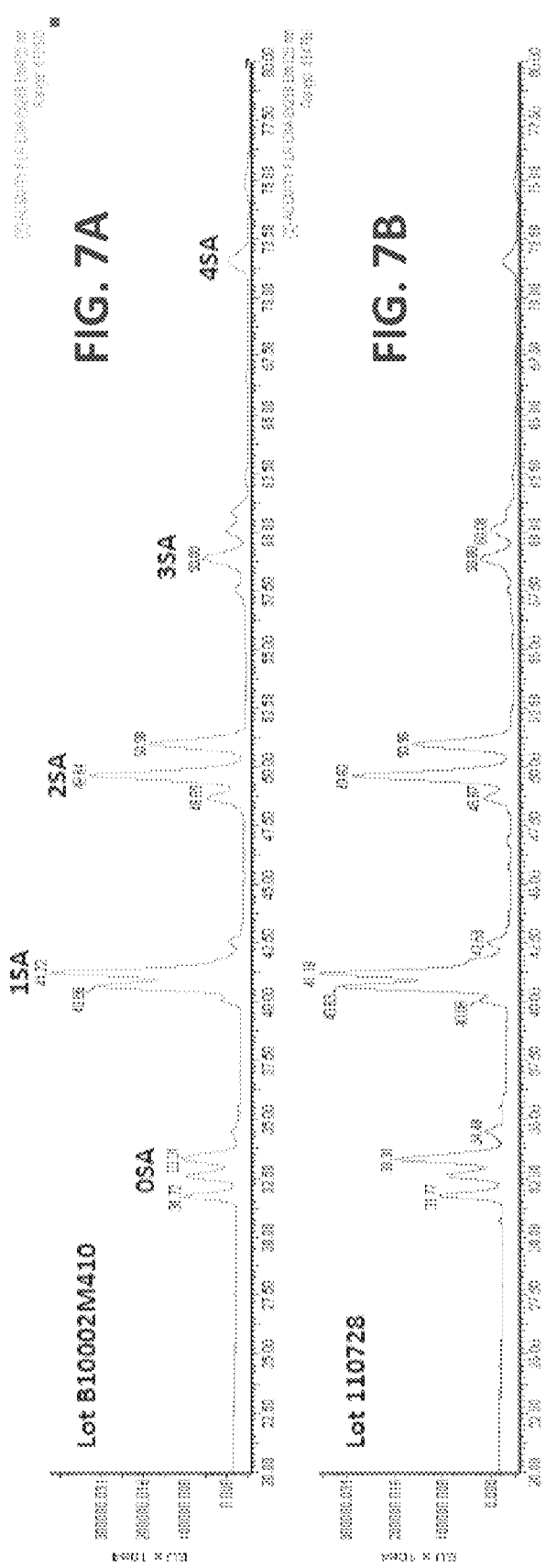

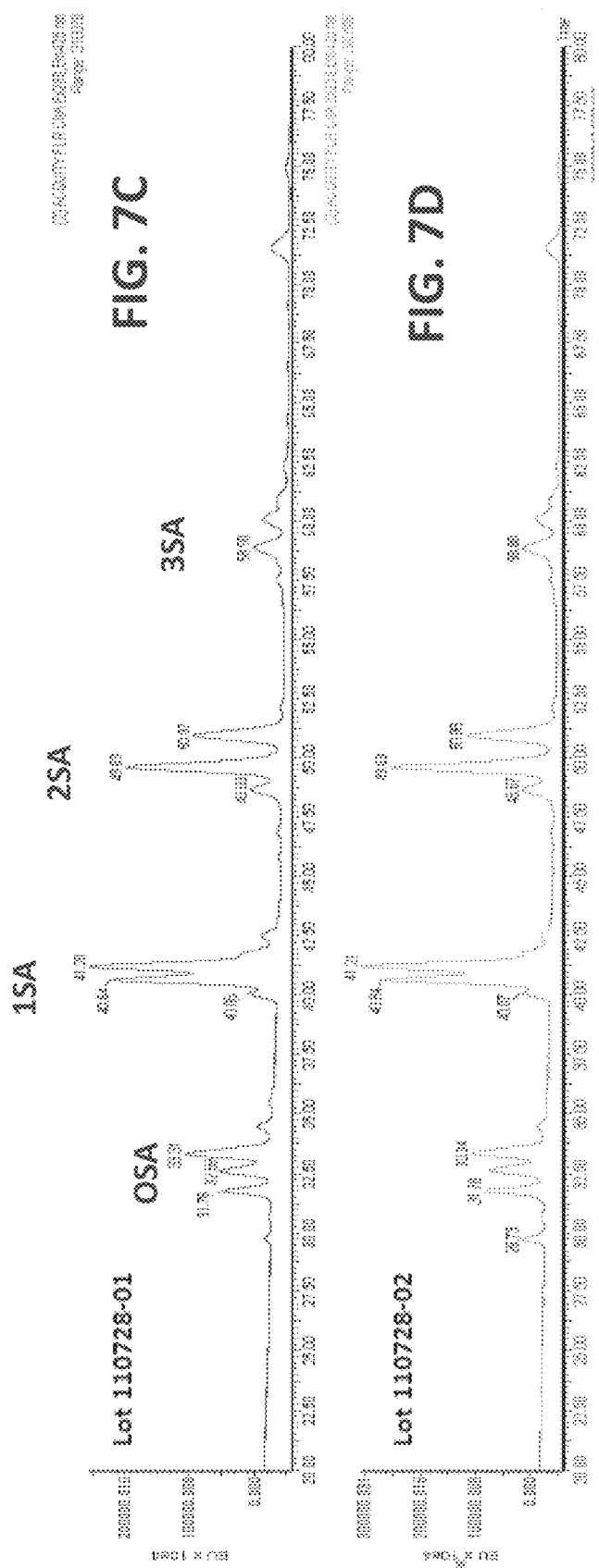

EFFICIENT SELECTIVITY OF RECOMBINANT PROTEINS

CROSS-REFERENCE TO RELATED APPLICATIONS

This application claims the benefit under 35 USC 119(e) of U.S. Provisional Application No. 62/039,416, filed Aug. 19, 2014; which application is incorporated herein by reference in its entirety for all purposes.

BACKGROUND

Sequence Listing

This application incorporates by reference the Sequence Listing submitted in Computer Readable Form as file 8700US_ST25.txt created on Aug. 19, 2015 (75,771 bytes).

Field of the Invention

The invention provides for expression of recombinant proteins in mammalian cells in a consistent and efficient manner. In particular, the invention includes methods and compositions for improved expression of proteins in mammalian cells by employing mammalian selection markers. The invention includes methods that facilitate selectivity and enhanced expression copies as well as protein yield of recombinant proteins in mammalian cells, and methods of using such expression systems.

Description of Related Art

The development of cellular expression systems is an important goal for providing a reliable and efficient source of a given protein for research and therapeutic use. Recombinant protein expression in mammalian cells is often preferred for manufacturing therapeutic proteins due to, for example, the ability of mammalian expression systems to appropriately post-translationally modify recombinant proteins.

Various vectors are available for expression in mammalian hosts, each containing selection markers that enable ease of isolation of recombinant protein-expressing cells during cell culture. Selectable marker genes (SMGs) are utilized in such systems because they confer a selective advantage for cells expressing the protein of interest, however SMGs must be optimized for their phenotypic neutrality, efficiency and versatility, among other reasons.

Despite the availability of numerous vectors and expression systems hosting SMGs, the expression of a recombinant protein achieved in mammalian systems is often unsatisfactory, whether in quantity or quality or both. The biological "fingerprint" of a molecule, for example post-translational modifications like glycosylation, is of particular importance in defining the molecule's utility and efficacy in the development of a recombinant protein therapeutic (Cumming, D. A., 1990, *Glycobiology*, 1(2):115-130). SMGs that do not negatively impact the biological properties of an expressed protein of interest are particularly advantageous.

Most SMGs are of bacterial origin and impart other disadvantages for use in mammalian systems due to growing concern for the risk of horizontal transfer of bacterial antibiotic resistance genes to environmental bacteria (Breyer, D. et al., 2014, *Critical Reviews in Plant Sciences* 33:286-330). Elimination of use of bacterial antibiotic resistance genes could have positive effects on consumer acceptance and alleviating such perceived risks.

Gene-engineered autologous cells are rapidly becoming a clinical success (see e.g. Kershaw, M. H. et al., 2013, *Nature Reviews: Cancer* 13:525-541). The choice and design of vectors for genetic modifications in human autologous cell products is critical, especially since the unwanted introduction of non-human components to a human autologous cell could have serious consequences for patient safety (Eaker, et al. 2013, *Stem cells Trans. Med.* 2:871-883; first published online in SCTMEXPRESS Oct. 7, 2013). A vector system having only components of mammalian origin, rather than bacterial, would be advantageous for use in patient-specific T cells for adoptive immunotherapy.

Thus it is desirable to introduce mammalian selectivity genes, especially those that give the transformed cells a phenotypic or metabolic advantage in expression systems for the production of mammalian proteins of interest. Moreover, a cell line that reliably expresses sufficiently high levels of a therapeutic protein, and appropriately and consistently modifies the therapeutic protein post-translationally, is highly desirable. Accordingly, there is a need in the art for improved mammalian expression systems.

BRIEF SUMMARY

The use of a mammalian tunicamycin (Tn) resistance gene as a selectable marker in a mammalian expression system can increase efficiency and copy number of transfectants. It has been observed that the use of a Tn resistance gene operably linked to a gene of interest creates selective pressure on a population of mammalian cells thereby increasing random integration of the transfectant (i.e. gene of interest). It is understood that selectable marker systems may foster selection of desired transfectants, however the methods of the invention impart an unexpected increase in both efficiency and random integration of the gene of interest, as well as reliable biological qualities of the desired protein. The compositions and methods of the invention thus allow the advantageous selection of qualitatively favorable post-translational modifications for expressed proteins.

In one aspect, the invention provides an isolated cell comprising a mammalian tunicamycin (Tn)-resistance gene encoding a protein having at least 93% identity to the amino acid sequence of SEQ ID NO:3, operably linked to a gene of interest (GOI) and at least one regulatory element. In a further aspect, the isolated cell comprises i) a mammalian tunicamycin (Tn)-resistance gene encoding a protein having at least 93% identity to the amino acid sequence of SEQ ID NO: 3, operably linked to at least one regulatory element, and ii) an exogenously added gene of interest (GOI).

In another aspect, the invention provides a method of producing a recombinant protein of interest (POI), wherein the method comprises: providing a mammalian host cell encoding a nucleic acid molecule comprising (i) a mammalian tunicamycin (Tn)-resistance gene and (ii) a gene encoding the POI; culturing the cell in the presence of a first concentration of Tn; isolating a cell population expressing at least one copy of the Tn-resistance gene; culturing the cell population in the presence of increasing concentrations of Tn, wherein increasing the concentration of Tn increases production of the POI; and isolating the POI from the cell culture.

In yet another aspect, the invention provides a method of glycosylating a N-glycan protein substrate, wherein the method comprises: providing a mammalian host cell encoding a nucleic acid molecule comprising a mammalian tunicamycin (Tn)-resistance gene operably linked to a gene encoding the protein substrate in need of glycosylation; culturing the cell in the presence of a first concentration of Tn; isolating a cell population expressing at least one copy of the Tn-resistance gene; culturing the cell population in the presence of increasing concentrations of Tn, wherein increasing the concentration of Tn increases production of the POI; and isolating the protein substrate from the cell culture.

In some embodiments of the methods, the Tn-resistance gene is operably linked to the gene encoding the POI, and the gene encoding the POI is operably linked to at least one regulatory element.

In some embodiments, the Tn-resistance gene is exogenously added to the cell. In other embodiments, the Tn-resistance gene encodes the protein having at least 93% identity to the amino acid sequence of SEQ ID NO:3. In other embodiments, the Tn-resistance gene encodes the protein having at least 94% identity to the amino acid sequence of SEQ ID NO:3. In some embodiments, the Tn-resistance gene encodes the protein having at least 93% identity to the amino acid sequence of SEQ ID NO:4. In still other embodiments, the Tn-resistance gene encodes the protein having at least 94% identity to the amino acid sequence of SEQ ID NO:4.

In some embodiments, the mammalian Tn-resistance gene comprises a Chinese hamster (*Cricetulus griseus*) Tn-resistance gene. In other embodiments, the mammalian Tn-resistance gene comprises a human Tn-resistance gene.

The Tn-resistance gene may also comprise the nucleic acid sequence selected from the group consisting of SEQ ID NO:2, SEQ ID NO:11, SEQ ID NO:12, SEQ ID NO:13, SEQ ID NO:14, SEQ ID NO:15, SEQ ID NO:16 and SEQ ID NO:17.

In certain embodiments of the aforementioned inventions, the mammalian Tn-resistance gene comprises a nucleic acid sequence having at least 92% identity to the nucleic acid sequence of SEQ ID NO:2. In some embodiments, the mammalian Tn-resistance gene comprises a nucleic acid sequence having at least 92% identity to the nucleic acid sequence of SEQ ID NO:12.

At least one regulatory element operably linked to the Tn-resistance gene is provided in the isolated cell of the invention, wherein the regulatory element includes, but is not limited to a promoter, ribosome-binding site, and enhancer. In still another embodiment, the GOI is operably linked to a promoter. In another embodiment, the GOI is operably linked to a ribosome-binding site, such as an IRES. As such, the cell is a recombinant cell comprising an expression cassette comprising a Tn-resistance gene operably linked to at least one regulatory element. In an embodiment, the expression cassette is exogenously added by well known methods including those described herein.

In some embodiments, the isolated cells and methods of the invention further comprise a second gene of interest (GOI), whereas the GOI encodes the protein of interest (POI). In one embodiment, the gene of interest (GOI) is an exogenously added GOI. In another embodiment, the exogenously-added GOI is a human gene. In yet another embodiment, the regulatory element is an exogenously added regulatory element.

In other embodiments, the first and/or second GOI encodes a POI including, but not limited to an antibody heavy chain, antibody light chain, antigen-binding fragment, and/or Fc-fusion protein.

In another embodiment, the first GOI and the second GOI are independently selected from the group consisting of a gene encoding for an antibody light chain or antigen-specific fragment thereof, an antibody heavy chain or antigen-specific fragment thereof, an Fc-fusion protein or a fragment thereof, and a receptor or ligand-specific fragment thereof. In one embodiment, a recombinase recognition site is present between the first GOI and the second GOI. In other embodiments, the invention further provides a recombinase recognition site 5' to the first GOI and a recombinase recognition site 3' with respect to the second GOI.

In still another embodiment, the GOI encodes a glycoprotein selected from an antibody light chain or antigen-binding fragment thereof, an antibody heavy chain or antigen-binding fragment thereof, an Fc-fusion protein or a fragment thereof, a ligand, and a receptor or ligand-binding fragment thereof.

The isolated, non-naturally occurring cells of the invention may be derived from a eukaryotic cell. In one embodiment, the cell is a mammalian cell. In some embodiments, the isolated cell is an ex vivo human cell. In other embodiments, the cell is selected from the group consisting of CHO (e.g. CHO K1, DXB-11 CHO, Veggie-CHO), COS (e.g. COS-7), lymphocyte, stem cell, retinal cell, Vero, CV1, kidney (e.g. HEK293, 293 EBNA, MSR 293, MDCK, HaK, BHK21), HeLa, HepG2, WI38, MRC 5, Colo25, HB 8065, HL-60, Jurkat, Daudi, A431 (epidermal), CV-1, U937, 3T3, L cell, C127 cell, SP2/0, NS-0, MMT cell, tumor cell, and a cell line derived from an aforementioned cell. In certain embodiments, the isolated cell of the invention is a CHO-K1 cell, a lymphocyte, retinal cell, or stem cell.

In one embodiment, the first concentration of Tn is 1 µg/mL. In another embodiment, the increasing concentrations of Tn comprises a second and third concentration of Tn.

In some embodiments, the second concentration is greater than the first concentration of Tn, and the third concentration is greater than the second concentration of Tn. In certain embodiments, the second concentration of Tn is 2.5 µg/ml, and the third concentration is 5 µg/mL.

In still other embodiments, the increasing concentrations of Tn comprises a second concentration of Tn, wherein the second concentration of Tn is 2.5 µg/ml or 5 µg/mL.

Any of the aspects and embodiments of the invention can be used in conjunction with any other aspect or embodiment of the invention, unless otherwise specified or apparent from the context.

Other objects and advantages will become apparent from a review of the ensuing detailed description.

BRIEF DESCRIPTION OF THE FIGURES

FIGS. 2A to 2C represent an alignment of mammalian GPT amino acid sequences, namely human (GPT_HUMAN; UniProtKB Accn. No. Q9H3H5; SEQ ID NO:4), Rhesus macaque (GPT_MACMU; UniProtKB Accn. No. F6TXM3; SEQ ID NO:5), chimpanzee (GPT_PANTR; UniProtKB Accn. No. H2R346; SEQ ID NO:6), dog (GPT_CANFA; UniProtKB Accn. No. E2RQ47; SEQ ID NO:7), guinea pig (GPT_CAVPO; UniProtKB Accn. No. E2RQ47; SEQ ID NO:8), rat (GPT_RAT; UniProtKB Accn. No. Q6P4Z8; SEQ ID NO:9), and mouse (GPT_MOUSE; UniProtKB Accn. No. P42867; SEQ ID NO:10) compared to Chinese hamster (GPT_CRIGR; UniProtKB Accn. No. P24140; SEQ ID NO:3) GPT amino acid sequences.

FIG. 3A depicts the method of selecting a positive cell transfectant from a first cell pool cultured with 1 µg/mL tunicamycin (Tn). Subsequently, a second cell culture with an increased concentration of tunicamycin, e.g. 2.5 µg/mL or 5 µg/mL, to enhance protein expression. FIG. 3B: depicts a method of selecting a positive cell transfectant from a first cell pool cultured with 1 µg/mL tunicamycin (Tn), and then serially increasing concentrations of Tn in subsequent cell cultures in order to optimize protein expression.

FIG. 4A: Cells are transfected with a Cre recombinase vector and hpt expression vector comprising eGFP; but cultured without hygromycin in culture. FIG. 4B: Cells are transfected with a Cre recombinase vector and hpt expression vector comprising eGFP; in the presence of 400 µg/mL hygromycin.

FIG. 5A: Cells are transfected with a Cre recombinase vector and CHO-GPT expression vector comprising eGFP; but without tunicamycin in culture. FIG. 5B: Cells are transfected with a Cre recombinase vector and CHO-GPT expression vector comprising eGFP; in the presence of 1 µg/mL Tn. FIG. 5C: Cells are transfected with a Cre recombinase vector and CHO-GPT expression vector comprising eGFP; in the presence of 2.5 µg/mL Tn. FIG. 5D: Cells are transfected with a Cre recombinase vector and Human GPT expression vector comprising eGFP; but without tunicamycin in culture. FIG. 5E: Cells are transfected with a Cre recombinase vector and Human GPT expression vector comprising eGFP; in the presence of 1 µg/mL Tn. FIG. 5F: Cells are transfected with a Cre recombinase vector and Human GPT expression vector comprising eGFP; in the presence of 2.5 µg/mL Tn.

FIG. 6A: illustrates the relative number of gene copies of CHO-GPT as measured by PCR for cell pools as follows: Pool-49 cells (no exogenous GPT added) without Tn selection; Pool-49 cells (no exogenous GPT) with 5 ug Tn selection; Pool-1 cells naturally express higher amounts of GPT (data not shown), and are tested without Tn selection; Pool-78 cells (no exogenous GPT) without Tn selection; CHO cells expressing exogenously-added hpt and 400 µg/mL Hygromycin selection; CHO cells expressing exogenous GPT under 1 µg/mL Tn selection conditions; CHO cells expressing exogenous GPT selected from a 1 µg/mL Tn selection pool further cultured in 1 µg/mL Tn; CHO cells expressing exogenous GPT selected from a 1 µg/mL Tn selection pool further cultured in 2.5 µg/mL Tn; CHO cells expressing exogenous GPT selected from a 1 µg/mL Tn selection pool further cultured in 5 µg/mL Tn. FIG. 6B: illustrates the relative number of gene copies of a gene of interest, eGFP, as measured by qPCR for the same cell pools (as FIG. 6A).

FIGS. 7A to 7D illustrate glycoform characteristics of Fc-fusion protein 1 (FcFP1) produced from cell culture as follows, FIG. 7A: CHO cells not expressing GPT using a standard protocol (Lot B10002M410), compared to FIG. 7B: CHO cells expressing CHO-GPT and no Tn selection (Lot 110728). FIG. 7C: CHO cells expressing CHO-GPT and selected with 1 µg/mL Tn (Lot 110728-01), compared to FIG. 7D: CHO cells expressing CHO-GPT and selected with 5 µg/mL Tn (Lot 110728-02). Each chromatogram indicates fractions containing sialylated residues as follows: OSA=zero sialic acid residues; 1SA=one sialic acid residue; 2SA=two sialic acid residues; 3SA=three sialic acid residues; 4SA=four sialic acid residues.

DETAILED DESCRIPTION

Figure 1:
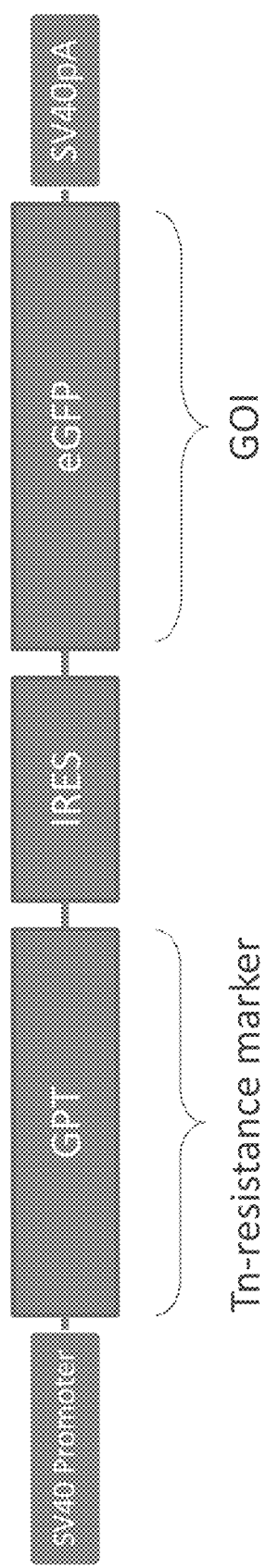
FIG. 1 illustrates a schematic diagram of the operative expression cassette in a cloning vector construct, used for introduction of the nucleic acid sequence encoding a gene of interest, for example eGFP, into a cell genome. SV40 Promoter: Simian virus 40 Promoter; GPT: GlcNAc-1-P transferase (e.g. CHO-GPT, SEQ ID NO:2; or hGPT, SEQ ID NO:12); IRES: internal ribosomal entry site; eGFP: enhanced Green Fluorescent Protein; SV40polyA: Simian virus 40 polyA.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure.

Unless defined otherwise, or otherwise specified, all technical and scientific terms used herein have the same meaning as commonly understood by one of ordinary skill in the art to which this invention belongs.

Although any methods and materials similar or equivalent to those described herein can be used in the practice or testing of the present invention, particular methods and materials are now described. All publications mentioned herein are incorporated herein by reference in their entirety.

A variety of genes well-known in the art may confer a selectable phenotype on mammalian cells in culture. Commonly, selectable marker genes express proteins, usually enzymes that confer resistance to various antibiotics in cell culture. In some selective conditions, cells that express a flourescent protein marker are made visible, and are thus selectable. Examples in the art include beta-lactamase (bla; beta-lactam antibiotic resistance gene or ampR; ampicillin resistance gene), bls (blasticidin resistance acetyl transferase gene), hygromycin phosphotransferase (hpt; hygromycin resistance gene), and others.

The methods described herein rely on the use of tunicamycin and enzymes (markers) that can allow cells resistant to tunicamycin to grow in cell culture. Tunicamycin (Tn) is mixture of antibiotics that act as inhibitors of bacterial and eukaryote N-acetylglucosamine transferases preventing formation of N-acetylglucosamine lipid intermediates and glycosylation of newly synthesized glycoproteins. (King, I. A., and Tabiowo, A., 1981, Effect of tunicamycin on epidermal glycoprotein and glycosaminoglycan synthesis in vitro. Biochem. J., 198(2):331-338). Tn is cytotoxic because it specifically inhibits UDP-N-acetylglucosamine: dolichol phosphate N-acetylglucosamine-1-P transferase (GPT), an enzyme that catalyzes the initial step of the biosynthesis of dolichol-linked oligosaccharides. In the presence of tunicamycin, asparagine-linked glycoproteins made in the endoplasmic reticulum (ER) are not glycosylated with N-linked glycans, and therefore may not fold correctly in the ER and thus, may be targeted for breakdown (Koizumi, et al. 1999, Plant Physiol. 121(2):353-362). Hence, Tn is a notable inducer of the unfolded protein response (UPR) which leads to apoptosis in bacterial and eukaryotic cells.

The gene for uridine diphosphate GPT (also known as GlcNAc-1-P transferase) was identified as being overexpressed under certain cellular conditions in order to confer resistance to Tn (Criscuolo and Krag, 1982, *J Biol Chem*, 263(36):19796-19803; Koizumi, et al., 1999, *Plant Physiology*, Vol. 121, pp. 353-361). The gene encoding GPT, also described as GenBank Accn. No. M36899 (SEQ ID NO: 2), was isolated from a Tn-resistant Chinese hamster ovary cell line and encodes a 408 amino acid protein (SEQ ID NO: 3) (Scocca and Krag, 1990, *J Biol Chem* 265(33):20621-20626; Lehrman, M. et al., 1988, *J Biol Chem* 263(36):19796-803). Hamster GPT was overexpressed in yeast cells (*S. pombe*) and conferred Tn resistance in these cells; also providing a convenient source for the purification of the GPT enzyme (Scocca JR , et al. 1995, *Glycobiology*, 5(1):129-36). Transcript levels of GPT were analyzed in hybridoma cells (B cells expressing IgG, vs. quiescent B cells) whereas it was observed that IgG-producing cells did not exhibit increased levels of GPT transcript or activity, yet a small increase in GPT was seen in the transition from quiescent to active B cells. It was concluded that GPT levels may correspond with the early development of proliferative response to LPS (antigen) stimulation in B cells (Crick, D. C. et al, 1994, *J Biol Chem* 269(14):10559-65).

Furthermore, it was previously unknown whether altering the expression of GPT, with or without the presence of Tn, in a cellular expression system will have an effect on the glycosylation of protein product, and therefore on product quality. It is understood that optimal and consistent glycosylation is a critical protein attribute in the production of therapeutic glycoproteins.

The present invention provides an improved method for production of recombinant proteins in mammalian cell systems utilizing a mammalian Tn-resistance gene, GPT, as a regulatable selection marker, whereas increased copy number of a gene of interest operably linked to GPT correlates with increased random integration of a GPT expression cassette into the cell.

The art has recognized that the manufacture of therapeutic proteins, particularly glycoproteins, relies on mammalian-type expression systems that mimic natural glycosylation of such proteins. (For review, see Bork, K. et al, 2009, J Pharm Sci. 98(10):3499-3508.) For example, the terminal monosaccharide of certain glycoproteins such as N-linked complex glycans is typically occupied by sialic acid. Sialylation may affect the glycoprotein's pharmacokinetic properties, such as absorption, serum half-life, and clearance, or other physicochemical or immunogenic properties of the glycoprotein. Overexpressed recombinant glycoproteins often have incomplete or inconsistent glycosylation. Reliable methods are critical for process consistency and quality of therapeutic glycoproteins produced in mammalian cell lines.

The present invention also provides an improved method for the glycosylation of recombinant proteins, i.e. a method for making glycoproteins, in mammalian cell systems in order to provide consistent quality yield of the desired proteins.

Definitions

DNA regions are operably linked when they are functionally related to each other. For example, a promoter is operably linked to a coding sequence if the promoter is capable of participating in the transcription of the sequence; a ribosome-binding site is operably linked to a coding sequence if it is positioned so as to permit translation. Generally, operably linked can include, but does not require, contiguity. In the case of sequences such as secretory leaders, contiguity and proper placement in a reading frame are typical features. A production enhancing sequence, such as a promoter, is operably linked to a gene of interest (GOI) where it is functionally related to the GOI, for example, where its presence results in increased expression of the GOI.

As such, the phrase "operably linked", such as in the context of DNA expression vector constructs, a control sequence, e.g., a promoter or operator or marker, is appropriately placed at a position relative to a coding sequence such that the control sequence directs or permits the production of a polypeptide/protein of interest encoded by the coding sequence. For example, where a selection marker is required for cells to survive in certain culture conditions, the gene of interest is operably linked to the selection marker gene because expression will not occur without the presence of an operable selection marker protein.

"Promoter" as used herein indicates a DNA sequence sufficient to direct transcription of a DNA sequence to which it is operably linked, i.e., linked in such a way as to permit transcription of the gene of interest and/or selection marker gene when the appropriate signals are present. The expression of a gene may be placed under control of any promoter or enhancer element known in the art.

An "expression vector" in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an Fc-fusion protein or polypeptide-encoding nucleic acid molecule is comprised in a naked DNA or RNA vector, including, for example, a linear expression element (as described in, for instance, Sykes and Johnston, 1997, *Nat Biotech* 12, 355-59), a compacted nucleic acid vector (as described in for instance U.S. Pat. No. 6,077,835 and/or WO00/70087), or a plasmid vector such as pBR322, pUC 19/18, or pUC 118/119. Such nucleic acid vectors and the usage thereof are well known in the art (see, for instance, U.S. Pat. No. 5,589,466 and U.S. Pat. No. 5,973,972).

As used herein "operator" indicates a DNA sequence that is introduced in or near a gene in such a way that the gene may be regulated by the binding of a repressor protein to the operator and, as a result, prevent or allow transcription of the GOI, i.e. a nucleotide encoding a polypeptide or protein of interest.

Ribosome binding sites include "internal ribosome entry sites" (IRESs) or may include a 5' cap. Many IRES sequences are well-known in the art. IRES represents a translation control sequence, wherein the IRES site is typically located 5' of a gene of interest and allows translation of the RNA in a cap-independent manner. Transcribed IRESs may directly bind ribosomal subunits such that the location of the mRNA's initiator codons is oriented properly in the ribosome for translation. IRES sequences are typically located in the 5' UTR of the mRNA (directly upstream of the initiation codon). IRESs functionally replace the need for various protein factors that interact with eukaryotic translation machinery.

The terms "enhanced" or "improved" when used to describe protein expression include an increase in the quantity and/or consistency of quality of the protein (i.e. gene product) produced by the expression system or methods of the invention. As such, this includes an enhancement of at least about 1.5-fold to at least about 3-fold enhancement in expression over what is typically observed by random integration into a genome, for example, as compared to a pool of integrants using another selectable marker construct. As such, fold-expression enhancement observed for proteins of interest is compared to an expression level of the same gene, measured under substantially the same conditions, in the absence of an expression cassette or cell of the invention comprising a GPT gene, or in the presence of an expression cassette or cell comprising a different selectable marker. Expression enhancement may also be measured by the resulting number of random integration events. Enhanced recombination efficiency includes an enhancement of the ability of a locus to recombine (for example, employing recombinase-recognition sites). Enhancement refers to a measurable efficiency over random recombination, which is typically 0.1%. In certain conditions, enhanced recombination efficiency is about 10-fold over random, or about 1%. Unless specified, the claimed invention is not limited to a specific recombination efficiency. Expression enhancement may also be measured by the resulting number of gene copies as measured by quantitative polymerase chain reaction (qPCR), or other well-known technique.

Enhanced or improved product also refers to the more consistent quality, for example, post-translational modifications observed with the GPT expression system of the invention. Consistent quality includes having e.g. a desirable glycosylation profile after replicate production lines. Consistency, with respect to quality, refers to a degree of uniformity and standardization, whereas replicate production batches are essentially free from variation. Calculating a Z-number to measure consistency is taught herein. Other statistical measures are known in the art for measuring consistency.

The phrase "selective pressure" is the force or stimulus applied to a living organism (e.g. a cell) or system (e.g. as an expression system) which alters the behavior and survival (such as ability to survive) of the living organism or system within a given environment.

The phrase "gene amplification" means an increase in the number of identical copies of a gene sequence. Certain cellular processes are characterized by the production of multiple copies of a particular gene or genes that amplify the phenotype that the gene confers on the cell, for example antibiotic resistance.

Where the phrase "exogenously added gene" or "exogenously added GOI" is employed with reference to an expression cassette, the phrase refers to any gene not present within the cell genome as found in nature, or an additional gene copy integrated into (a different locus within) the genome. For example, an "exogenously added gene" within a CHO genome (e.g., an selectable marker gene), can be a hamster gene not found within the particular CHO locus in nature (i.e., a hamster gene from another locus in the hamster genome), a gene from any other species (e.g., a human gene), a chimeric gene (e.g., human/mouse), or can be a hamster gene not found within the CHO genome in nature (i.e., a hamster gene having less than 99.9% identity to the gene from another locus in the hamster genome), or any other gene not found in nature to exist within the CHO natural genome.

Random integration events differ from targeted integration events, whereas insertion of a gene into the genome of the cell is not site-specific in random integration events. An example of targeted integration is homologous recombination. Random (nonhomologous) integration means that the location (locus) of the resulting integrant is not known or specified. Random integration is thought to occur by non-homologous end joining (NHEJ), however is not limited to this method.

Selection efficiency means the percent population of surviving cells expressing the selectable marker and, if applicable, the protein of interest under the control of the selectable marker.

Percent identity, when describing a Tn-resistance protein, is meant to include homologous sequences that display the recited identity along regions of contiguous homology, but the presence of gaps, deletions, or insertions that have no homolog in the compared sequence are not taken into account in calculating percent identity. In explaining the usage of "percent identity" in this context, the following amino acid sequence comparison will be referred to:

```
1 MWAFPELPLPLPLLVNLIGSLLGFVATVTLIPAFRSHFIAARLCGQDLNKLSQQQIPESQ  60 GPT_MOUSE

1 MWAFPELPL--PLLVNLFGSLLGFVATVTLIPAFRSHFIAARLCGQDLNKLSRQQIPESQ  58 GPT_CRIG
```

As used herein, a "percent identity" determination between the "GPT_CRIG" sequence above (for a Chinese hamster GPT) with a mouse homolog ("GPT_MOUSE") would not include a comparison of hamster amino acids 10 and 11, since the hamster homolog has no homologous sequence to compare in an alignment (i.e., the mouse GPT has an insertion at that point, or the hamster homolog has a gap or deletion, as the case may be). Thus, in the comparison above, the percent identity comparison would extend from the "MWA" at the 5' end to the "ESQ" at the 3' end. In that event, the mouse homolog differs only in that it has an "R" at hamster GPT position 51. Since the comparison is over 58 contiguous bases in a 60 base pair stretch, with only one amino acid difference (which is not a gap, deletion, or insertion), there is over 98% identity between the two sequences (hamster and mouse) from hamster GPT position 1 to hamster GPT position 58 (because "percent identity"

does not include penalties for gaps, deletions, and insertions). Although the above example is based on an amino acid sequence, it is understood that nucleic acid sequence percent identity would be calculated in the same manner.

The term "cell" includes any cell that is suitable for expressing a recombinant nucleic acid sequence. Cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g. *S. cerevisiae, S. pombe, P. partoris, P. methanolica*, etc.), plant cells, insect cells (e.g. SF-9, SF-21, baculovirus-infected insect cells, *Trichoplusia ni*, etc.), non-human animal cells, mammalian cells, human cells, or cell fusions such as, for example, hybridomas or quadromas. In certain embodiments, the cell is a human, monkey, ape, hamster, rat or mouse cell. In other embodiments, the cell is eukaryotic and is selected from the following cells: CHO (e.g. CHO K1, DXB-11 CHO, Veggie-CHO), COS (e.g. COS-7), retinal cells, Vero, CV1, kidney (e.g. HEK293, 293 EBNA, MSR 293, MDCK, HaK, BHK21), HeLa, HepG2, WI38, MRC 5, Colo25, HB 8065, HL-60, Jurkat, Daudi, A431 (epidermal), CV-1, U937, 3T3, L cell, C127 cell, SP2/0, NS-0, MMT cell, tumor cell, and a cell line derived from an aforementioned cell. In some embodiments, the cell comprises one or more viral genes, e.g. a retinal cell that expresses a viral gene (e.g. a PER.C6® cell).

The phrase "integrated cell density", or "ICD" means the density of cells in a culture medium taken as an integral over a period of time, expressed as cell-days per mL. In some embodiments, the ICD is measured around the twelfth day of cells in culture.

"Glycosylation" or the phrase "glycosylating a protein" includes the formation of glycoproteins whereas oligosaccharides are attached either to the side chain of the asparagine (Asn) residue (i.e. N-linked) or serine (Ser)/threonine (Thr) residue (i.e. O-linked) of a protein. Glycans can be homo- or heteropolymers of monosaccharide residues, which can be linear or branched. N-linked glycosylation is known to initiate primarily in the endoplasmic reticulum, whereas O-linked glycosylation is shown to initiate in either the ER or Golgi apparatus.

An "N-glycan protein" or an "N-glycan protein substrate" includes proteins that contain or can accept N-linked oligosaccharides. N-glycans can be composed of N-acetyl galactosamine (GalNAc), mannose (Man), fucose (Fuc), galactose (Gal), neuraminic acid (NANA), and other monosaccharides, however N-glycans usually have a common core pentasaccharide structure including: three mannose and two N-acetylglucosamine (GlcNAc) sugars. Proteins with the consecutive amino acid sequence (i.e. sequon) Asn-X-Ser or Asn-X-Thr, where X is any amino acid except proline, can provide an attachment site for N-glycans.

General Description

The invention is based at least in part on the discovery that under certain conditions recombinant proteins may be produced in a cell wherein the gene encoding the protein is operably linked to a Tn-resistance gene, GPT, and selection of a protein-producing cell is formatted to increase random integration events in the cell genome and thus increase copy number of the gene of interest, and ultimately protein production.

The invention is also based at least in part on the finding that the protein-producing cell may be optimized to express proteins with consistent and reliable post-translational modifications. GPT expression cassettes can also be integrated in a cellular genome, as in expression constructs, such as via expression vectors, using various gene editing techniques known in the art. Expression vectors comprising GPT can be integrated into a genome by random or targeted recombination such as, homologous recombination or recombination mediated by recombinases that recognize specific recombination sites (e.g., Cre-lox-mediated recombination).

Homologous recombination in eukaryotic cells can be facilitated by introducing a break in the chromosomal DNA at the integration site. Model systems have demonstrated that the frequency of homologous recombination during gene targeting increases if a double-strand break is introduced within the chromosomal target sequence. This may be accomplished by targeting certain nucleases to the specific site of integration. DNA-binding proteins that recognize DNA sequences at the target locus are known in the art. Gene targeting vectors are also employed to facilitate homologous recombination. In the absence of a gene targeting vector for homology directed repair, the cells frequently close the double-strand break by non-homologous end-joining (NHEJ) which may lead to deletion or insertion of multiple nucleotides at the cleavage site. Gene targeting vector construction and nuclease selection are within the skill of the artisan to whom this invention pertains.

In some examples, zinc finger nucleases (ZFNs), which have a modular structure and contain individual zinc finger domains, recognize a particular 3-nucleotide sequence in the target sequence (e.g. site of targeted integration). Some embodiments can utilize ZFNs with a combination of individual zinc finger domains targeting multiple target sequences.

Transcription activator-like (TAL) effector nucleases (TALENs) may also be employed for site-specific genome editing. TAL effector protein DNA-binding domain is typically utilized in combination with a non-specific cleavage domain of a restriction nuclease, such as Fokl. In some embodiments, a fusion protein comprising a TAL effector protein DNA-binding domain and a restriction nuclease cleavage domain is employed to recognize and cleave DNA at a target sequence within the locus of the invention (Boch J et al., 2009 *Science* 326:1509-1512).

RNA-guided endonucleases (RGENs) are programmable genome engineering tools that were developed from bacterial adaptive immune machinery. In this system—the clustered regularly interspaced short palindromic repeats (CRISPR)/CRISPR-associated (Cas) immune response—the protein Cas9 forms a sequence-specific endonuclease when complexed with two RNAs, one of which guides target selection. RGENs consist of components (Cas9 and tracrRNA) and a target-specific CRISPR RNA (crRNA). Both the efficiency of DNA target cleavage and the location of the cleavage sites vary based on the position of a protospacer adjacent motif (PAM), an additional requirement for target recognition (Chen, H. et al, *J. Biol. Chem.* published online Mar. 14, 2014, as Manuscript M113.539726).

Still other methods of homologous recombination are available to the skilled artisan, such as BuD-derived nucleases (BuDNs) with precise DNA-binding specificities (Stella, S. et al. *Acta Cryst.* 2014, D70, 2042-2052). Precise genome modification methods are chosen based on the tools available compatible with unique target sequences within the genome so that disruption of the cell phenotype is avoided.

Cells and methods are provided for stably integrating a nucleic acid sequence (gene of interest) into a mammalian cell, wherein the nucleic acid sequence is capable of enhanced expression by virtue of being integrated with a GPT sequence. Compositions and methods are also provided for using GPT in connection with expression constructs, for example, expression vectors, and for adding an exogenous GPT into a mammalian cell of interest. Cells and methods are provided for use in a consistent yet robust method of making glycoproteins, particularly therapeutic glycoproteins.

Construction of a GPT Selection Marker Cassette

Expression vectors comprising an operative GPT expression cassette are provided herein. The expression cassette comprises the necessary regulatory elements to permit and drive transcription and translation of mammalian GPT and the desired gene product.

Various combinations of the genes and regulatory sequences described herein can also be developed. Examples of other combinations of the appropriate sequences described herein that can also be developed include sequences that include multiple copies of the GPT genes disclosed herein, or sequences derived by combining the disclosed GPT with other nucleotide sequences to achieve optimal combinations of regulatory elements. Such combinations can be contiguously linked or arranged to provide optimal spacing of GPT oriented to the gene of interest and the regulatory elements.

Homologous sequences of genes encoding GPT are known to exist in cells from other mammalian species (such as, for example, humans; see FIG. 2) as well as in cell lines derived from other mammalian tissue types, and can be isolated by techniques that are well-known in the art. An exemplary list of mammalian GPT amino acid sequences is provided in FIG. 2. Changes in nucleotide sequence, such as codon optimization, can be made to nucleotide sequences set forth in SEQ ID NOs:2 and 11-17 in order to permit optimal expression of the corresponding GPT proteins set forth in SEQ ID NOs:3-10. In addition, changes can be made in the amino acid sequence set forth in SEQ ID NOs:3-10 by making changes to the nucleotide sequences encoding GPT. Such techniques including, but not limited to, site-directed or random mutagenesis techniques are well known in the art.

The resulting GPT variants can then be tested for GPT activity as described herein, e.g. tested for resistance to tunicamycin. GPT proteins that are at least about 93% identical, or at least about 95% identical, or at least about 96% identical, or at least about 97% identical, or at least about 98% identical in amino acid sequence to SEQ ID NO:3 having GPT activity are isolatable by routine experimentation, and are expected to exhibit the same resistance to Tn, selectivity efficiency and post-translational benefits as for SEQ ID NO:3. Accordingly, mammalian homologs of GPT and variants of GPT are also encompassed by embodiments of the invention. FIGS. 2A to 2C show an alignment of various mammalian GPT amino acid sequences (namely, SEQ ID NOs: 3-10). The mammalian GPT sequences (nucleic acid and amino acid) are conserved among hamster, human, mouse and rat genomes. Table 1 identifies exemplary mammalian GPT proteins and their degree of homology.

TABLE 1A

Amino acid identity of GPT homologs

| Animal | SEQ ID NO | % id Human | % id Mouse | % id Rat | % id Hamster |
|---|---|---|---|---|---|
| Hamster | 3 | 93.87 | 96.08 | 96.08 | — |
| Mouse | 10 | 94.12 | — | 97.07 | 96.08 |
| Human | 4 | — | 94.12 | 93.63 | 93.87 |
| Rat | 9 | 93.63 | 97.07 | — | 96.08 |

TABLE 1B

Nucleic acid identity of representative GPT homologs

| Animal | SEQ ID NO | % id Hamster |
|---|---|---|
| Hamster | 2 | — |
| Mouse | 11 | 92 |
| Human | 12 | 92 |
| Rat | 13 | 94 |
| Macaque | 14 | 92 |
| Chimp | 15 | 92 |

Cell populations expressing enhanced levels of a protein of interest can be developed using the GPT/tunicamycin methods provided herein. The absolute level of expression will vary with the specific protein, depending on how efficiently the protein is processed by the cell.

Accordingly, the invention also includes a GPT-expressing nucleotide sequence selected from the group consisting of SEQ ID NOs:2 and 11-17. The invention also encompasses a GPT-expressing nucleotide sequence that is at least 92% identical, at least 93% identical, at least 94% identical, at least 95% identical, at least 96% identical, at least 98% identical, or at least 99% identical to the nucleotide sequence selected from the group consisting of SEQ ID NOs:2 and 11-17.

The invention includes vectors comprising SEQ ID NO:1, SEQ ID NO:2 or SEQ ID NO:12. Vectors comprising a mammalian GPT gene, and optional regulatory elements, include vectors for transient or stable transfection.

In one embodiment, the GPT gene is employed to enhance the expression of a GOI, as illustrated in FIG. 1. FIG. 1 shows a GOI operably linked with an IRES sequence and a GPT selectable marker. The GPT cassette further includes a promoter sequence, e.g. SV40 promoter, and a polyadenylation (poly(A)) sequence, e.g. SV40 poly(A).

Figure 3B:
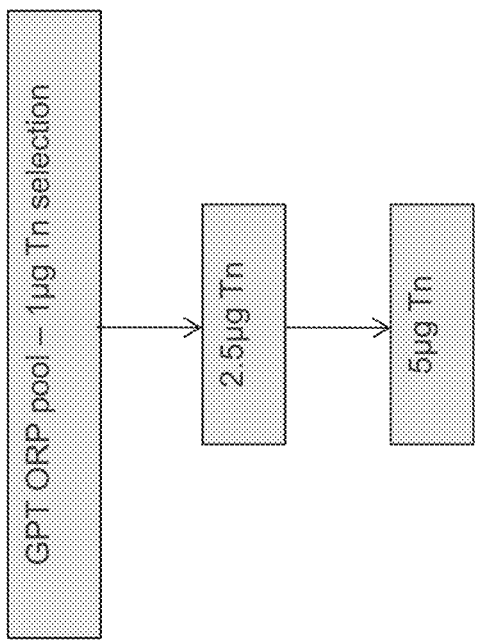
FIGS. 3A and 3B exemplifies how protein optimization can be achieved using the methods and compositions of the invention.
Figure 3A:
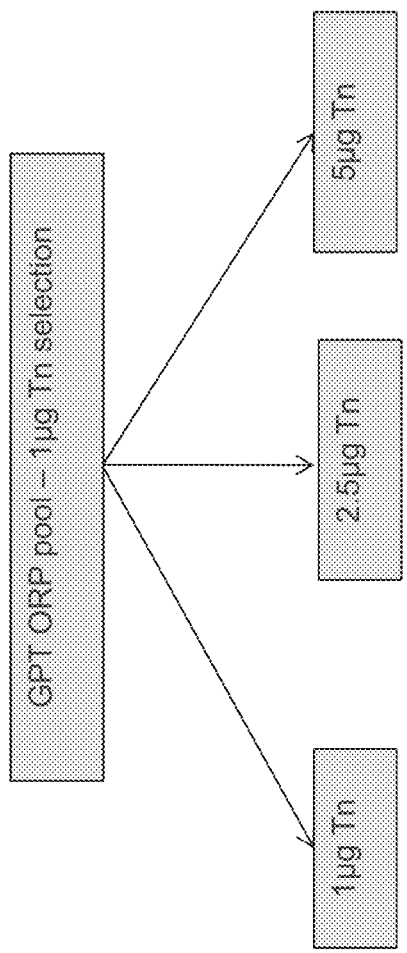

The expression-enhancing cassette (including GPT and an upstream promoter) is optimally integrated in a cell genome. Using the methods of the invention, a GOI is expressed within the GPT expression cassette under culture conditions based on increasing concentrations of Tn (FIG. 3A or FIG. 3B). A FACS readout, such as that shown in FIGS. 5B, 5C, 5E and 5F, exemplifies the distribution of expression in a stably transfected population of cells, in particular the dramatic increase in selection efficiency using mammalian Tn-resistant selection markers, CHO-GPT and hGPT. Mammalian GPT expression further enhances expression of a gene product of interest, for example production of a fluorescent protein, eGFP. Consecutive cultures of increasing concentrations of Tn result in an enhanced expression of about two-fold in comparison to the GOI expressed in an expression system using GPT under culture conditions based on one concentration of Tn, such as that exemplified in FIG. 6B.

The invention includes a mammalian cell comprising such a GPT gene wherein the GPT gene is exogenous and is integrated into the cell genome by the methods of the invention. Cells comprising such a GPT gene having at least one exogenously-added gene of interest (GOI) that is upstream or downstream to the GPT gene.

In various embodiments, expression of a GOI can be enhanced by placing the GOI under the control of a mammalian selectable marker GPT. In other embodiments, the random integration events of a GOI can be enhanced by placing the GOI under the control of a mammalian selectable marker GPT and providing cell culture conditions comprising greater than 0.5 µg/mL Tn concentration. In some embodiments, the cell culture conditions comprise greater than 1 µg/mL Tn concentration. A regulatory element may be operably linked to the GOI where expression of the GOI—at the selected distance from the GOI and GPT (in the 5' or 3' direction)—retains the ability to enhance expression of the GOI over, for example, expression typically observed due to a random integration event. In various embodiments, enhancement is at least about 1.5-fold to about 2-fold or more. Enhancement in expression as compared to a random integration, or random expression, is about 1.5-fold or about 2-fold or more.

In another embodiment, uniformly glycosylated proteins can be attained using the methods and compositions of the invention. As shown in Table 4, GPT/GOI recombinant protein batches treated with Tn allow replicate batches with equivalent glycosylation profiles. As such, enhanced protein expression such as consistent glycosylation profiles can be directly compared by calculating Z-number as taught herein. The Z-number equation takes into consideration takes into account the relative number of peaks on a chromatogram representing sialic acid (SA) moieties, as well as the relative shape and intensity of each peak. Z-number is based on the area occupied by each peak and may be used as a measure of consistency for complex glycoproteins (see e.g. FIGS. 7A-7D, FIG. 8, and Example 3, described herein.

Protein expression optimization can also be achieved for each GOI, including, for example, expression cassette orientation or codon optimization. Protein optimization may also be achieved by varying the incremental Tn concentration in the cell culture methods.

Recombinant expression vectors can comprise synthetic or cDNA-derived DNA fragments encoding a protein, operably linked to a suitable transcriptional and/or translational regulatory element derived from mammalian, viral or insect genes. Such regulatory elements include transcriptional promoters, enhancers, sequences encoding suitable mRNA ribosomal binding sites, and sequences that control the termination of transcription and translation, as described in detail herein. Mammalian expression vectors can also comprise nontranscribed elements such as an origin of replication, other 5' or 3' flanking nontranscribed sequences, and 5' or 3' nontranslated sequences such as splice donor and acceptor sites. Additional selectable marker genes (such as fluorescent markers) to facilitate recognition of transfectants may also be incorporated.

In another embodiment, the vector comprises a nucleic acid molecule (or gene of interest) encoding a protein of interest, including an expression vector comprising the nucleic acid molecules (genes) described wherein the nucleic acid molecule (gene) is operably linked to an expression control sequence.

A vector comprising a gene of interest (GOI) is provided, wherein the GOI is operably linked to an expression control sequence suitable for expression in a mammalian host cell.

Useful promoters that may be used in the invention include, but are not limited to, the SV40 early promoter region, the promoter contained in the 3' long terminal repeat of Rous sarcoma virus, the regulatory sequences of the metallothionein gene, mouse or human cytomegalovirus IE promoter (Gossen et al., (1995) Proc. Nat. Acad. Sci. USA 89:5547-5551), the cauliflower mosaic virus 35S RNA promoter, and the promoter of the photosynthetic enzyme ribulose biphosphate carboxylase, promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I; insulin; immunoglobulin; mouse mammary tumor virus; albumin; a-fetoprotein; al-antitrypsin; 13-globin; and myosin light chain-2.

Nucleic acid molecules of the invention may also be operably linked to an effective poly (A) termination sequence, e.g. SV40 poly(A), an origin of replication for plasmid product in E. coli, and/or a convenient cloning site (e.g., a polylinker). Nucleic acids may also comprise a regulatable inducible promoter (inducible, repressable, developmentally regulated) as opposed to a constitutive promoter such as CMV IE (the skilled artisan will recognize that such terms are actually descriptors of a degree of gene expression under certain conditions).

The invention provides methods for producing a protein of interest whereas an expression vector is provided comprising a gene of interest (GOI) is provided. Such expression vectors may be used for recombinant production of any protein of interest. Transcriptional and translational control sequences in expression vectors useful for transfecting vertebrate cells may be provided by viral sources. For example, commonly used promoters and enhancers are derived from viruses such as polyoma, adenovirus 2, simian virus 40 (SV40), and human cytomegalovirus (CMV). Viral genomic promoters, control and/or signal sequences may be utilized to drive expression, provided such control sequences are compatible with the host cell chosen. Non-viral cellular promoters can also be used (e.g., the β-globin and the EF-1α promoters), depending on the cell type in which the recombinant protein is to be expressed.

DNA sequences derived from the SV40 viral genome, for example, the SV40 origin, early and late promoter, enhancer, splice, and polyadenylation sites may be used to provide other genetic elements useful for expression of a heterologous DNA sequence. Early and late promoters are particularly useful because both are obtained easily from the SV40 virus as a fragment that also comprises the SV40 viral origin of replication (Fiers et al., Nature 273:113, 1978). Smaller or larger SV40 fragments may also be used. Typically, the approximately 250 by sequence extending from the Hind III site toward the BglI site located in the SV40 origin of replication is included.

Bicistronic expression vectors used for the expression of multiple transcripts have been described previously (Kim S. K. and Wold B. J., Cell 42:129, 1985; Kaufman et al. 1991, supra) and can be used in combination with a GPT expression system. Other types of expression vectors will also be useful, for example, those described in U.S. Pat. No. 4,634,665 (Axel et al.) and U.S. Pat. No. 4,656,134 (Ringold et al.).

An integration site, for example, a recombinase recognition site, can be placed 5' or 3' to the gene sequence encoding the POI. One example of a suitable integration site is a lox p site. Another example of a suitable integration site is two recombinase recognition sites, for example, selected from the group consisting of a lox p site, lox and a lox 5511 site.

Gene Amplification Cassettes and Expression Vectors Thereof

Useful regulatory elements, described previously or known in the art, can also be included in the nucleic acid constructs used to transfect mammalian cells. FIG. 1 exemplifies an operative cassette in a GPT vector further comprising a promoter sequence, IRES sequence, gene of interest, and poly(A) sequence.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an antibody-encoding nucleic acid molecule is comprised in a naked DNA or RNA vector, including, for example, a linear expression element (as described in, for instance, Sykes and Johnston, *Nat Biotech* 12, 355-59 (1997)), a compacted nucleic acid vector (as described in for instance U.S. Pat. No. 6,077,835 and/or WO 00/70087), or a plasmid vector such as pBR322, pUC 19/18, or pUC 118/119. Such nucleic acid vectors and the usage thereof are well known in the art (see, for instance, U.S. Pat. No. 5,589,466 and U.S. Pat. No. 5,973,972).

An expression vector may alternatively be a vector suitable for expression in a yeast system. Any vector suitable for expression in a yeast system may be employed. Suitable vectors include, for example, vectors comprising constitutive or inducible promoters such as yeast alpha factor, alcohol oxidase and PGH (reviewed in: F. Ausubel et al., ed. Current Protocols in Molecular Biology, Greene Publishing and Wiley InterScience New York (1987), and Grant et al., *Methods in Enzymol* 153, 516-544 (1987)).

In certain embodiments, the vector comprises a nucleic acid molecule (or gene of interest) encoding a protein of interest, including an expression vector comprising the nucleic acid molecules (genes) described wherein the nucleic acid molecule (gene) is operably linked to an expression control sequence suitable for expression in the host cell.

Expression control sequences are engineered to control and drive the transcription of genes of interest, and subsequent expression of proteins in various cell systems. Plasmids combine an expressible gene of interest with expression control sequences (i.e. expression cassettes) that comprise desirable regulatory elements such as, for example, promoters, enhancers, selectable markers, operators, etc. In an expression vector of the invention, GPT and the proteins of interest, such as antibody-encoding nucleic acid molecules, may comprise or be associated with any suitable promoter, enhancer, operator, repressor protein, poly (A) termination sequences and other expression-facilitating elements.

The expression of a gene of interest, such as an antibody-encoding nucleotide sequence, may be placed under control of any promoter or enhancer element known in the art. Examples of such elements include strong expression promoters (e. g., human CMV IE promoter/enhancer or CMV major IE (CMV-MIE) promoter, as well as RSV, SV40 late promoter, SL3-3, MMTV, ubiquitin (Ubi), ubiquitin C (UbC), and HIV LTR promoters).

In some embodiments, the vector comprises a promoter selected from the group consisting of SV40, CMV, CMV-IE, CMV-MIE, RSV, SL3-3, MMTV, Ubi, UbC and HIV LTR.

Nucleic acid molecules of the invention may also be operably linked to an effective poly (A) termination sequence, an origin of replication for plasmid product in *E. coli*, an antibiotic resistance gene as selectable marker, and/or a convenient cloning site (e.g., a polylinker). Nucleic acids may also comprise a regulatable inducible promoter (inducible, repressable, developmentally regulated) as opposed to a constitutive promoter such as CMV IE (the skilled artisan will recognize that such terms are actually descriptors of a degree of gene expression under certain conditions).

Selectable markers are elements well-known in the art. In some circumstances, additional selectable markers may be employed, in addition to GPT, wherein such markers make the cells visible. Positive or negative selection may be used.

In some embodiments, the vector comprises one or more selectable marker genes encoding green fluorescent protein (GFP), enhanced green fluorescent protein (eGFP), cyano fluorescent protein (CFP), enhanced cyano fluorescent protein (eCFP), yellow fluorescent protein (YFP) or enhanced yellow fluorescent protein (eYFP).

For the purposes of this invention, gene expression in eukaryotic cells may be tightly regulated using a strong promoter that is controlled by an operator that is in turn regulated by a regulatory fusion protein (RFP). The RFP consists essentially of a transcription blocking domain, and a ligand-binding domain that regulates its activity. Examples of such expression systems are described in US20090162901A1, which is herein incorporated by reference in its entirety.

A number of operators in prokaryotic cells and bacteriophage have been well characterized (Neidhardt, ed. *Escherichia coli* and *Salmonella*; Cellular and Molecular Biology 2d. Vol 2 ASM Press, Washington D.C. 1996). These include, but are not limited to, the operator region of the LexA gene of *E. coli*, which binds the LexA peptide, and the lactose and tryptophan operators, which bind the repressor proteins encoded by the LacI and trpR genes of *E. coli*. These also include the bacteriophage operators from the lambda $P_R$ and the phage P22 ant/mnt genes which bind the repressor proteins encoded by lambda cl and P22 arc. In some embodiments, when the transcription blocking domain of the repressor protein is a restriction enzyme, such as NotI, the operator is the recognition sequence for that enzyme. One skilled in the art will recognize that the operator must be located adjacent to, or 3' to the promoter such that it is capable of controlling transcription by the promoter. For example, U.S. Pat. No. 5,972,650, which is incorporated by reference herein, specifies that tetO sequences be within a specific distance from the TATA box. In specific embodiments, the operator is preferably placed immediately downstream of the promoter. In other embodiments, the operator is placed within 10 base pairs of the promoter.

In certain embodiments, the operator is selected from the group consisting of tet operator (tetO), NotI recognition sequence, LexA operator, lactose operator, tryptophan operator and Arc operator (AO). In some embodiments, the repressor protein is selected from the group consisting of TetR, LexA, LacI, TrpR, Arc, LambdaCl and GAL4. In other embodiments, the transcription blocking domain is derived from a eukaryotic repressor protein, e.g. a repressor domain derived from GAL4.

In an exemplary cell expression system, cells are engineered to express the tetracycline repressor protein (TetR) and a protein of interest is placed under transcriptional control of a promoter whose activity is regulated by TetR. Two tandem TetR operators (tetO) are placed immediately downstream of a CMV-MIE promoter/enhancer in the vector. Transcription of the gene encoding the protein of interest directed by the CMV-MIE promoter in such vector may be blocked by TetR in the absence of tetracycline or some other suitable inducer (e.g. doxycycline). In the presence of an inducer, TetR protein is incapable of binding tetO, hence transcription then translation (expression) of the protein of interest occurs. (See, e.g., U.S. Pat. No. 7,435,553, which is herein incorporated by reference in its entirety.)

Another exemplary cell expression system includes regulatory fusion proteins such as TetR-$ER_{LBD}$T2 fusion protein, in which the transcription blocking domain of the fusion protein is TetR and the ligand-binding domain is the estrogen receptor ligand-binding domain ($ER_{LBD}$) with T2 mutations ($ER_{LBD}$T2; Feil et al. (1997) Biochem. Biophys. Res. Commun. 237:752-757). When tetO sequences were placed downstream and proximal to the strong CMV-MIE promoter, transcription of the nucleotide sequence of interest from the CMV-MIE/tetO promoter was blocked in the presence of tamoxifen and unblocked by removal of tamoxifen. In another example, use of the fusion protein Arc2-$ER_{LBD}$T2, a fusion protein consisting of a single chain dimer consisting of two Arc proteins connected by a 15 amino acid linker and the $ER_{LBD}$T2 (supra), involves an Arc operator (AO), more specifically two tandem arc operators immediately downstream of the CMV-MIE promoter/enhancer. Cell lines may be regulated by Arc2-$ER_{LBD}$T2, wherein cells expressing the protein of interest are driven by a CMV-MIE/ArcO2 promoter and are inducible with the removal of tamoxifen. (See, e.g., US 20090162901A1, which is herein incorporated by reference.)

In some embodiments, a vector of the invention comprises a CMV-MIE/TetO or CMV-MIE/AO2 hybrid promoter.

The vectors of the invention may also employ Cre-lox tools for recombination technology in order to facilitate the replication of a gene of interest. A Cre-lox strategy requires at least two components: 1) Cre recombinase, an enzyme that catalyzes recombination between two loxP sites; and 2) loxP sites (e.g. a specific 34-base pair by sequence consisting of an 8-bp core sequence, where recombination takes place, and two flanking 13-bp inverted repeats) or mutant lox sites. (See, e.g. Araki et al. PNAS 92:160-4 (1995); Nagy, A. et al. Genesis 26:99-109 (2000); Araki et al. Nuc Acids Res 30(19):e103 (2002); and US20100291626A1, all of which are herein incorporated by reference). In another recombination strategy, yeast-derived FLP recombinase may be utilized with the consensus sequence FRT (see also, e.g. Dymecki, S. PNAS 93(12): 6191-6196 (1996)).

In another aspect, a gene (i.e. a nucleotide sequence encoding a recombinant polypeptide of the invention) is inserted upstream or downstream of the GPT gene of the expression cassette, and is optionally operably linked to a promoter, wherein the promoter-linked gene is flanked 5' by a first recombinase recognition site and 3' by a second recombinase recognition site. Such recombinase recognition sites allow Cre-mediated recombination in the host cell of the expression system. In some instances, a second promoter-linked gene is downstream (3') of the first gene and is flanked 3' by the second recombinase recognition site. In still other instances, a second promoter-linked gene is flanked 5' by the second recombinase site, and flanked 3' by a third recombinase recognition site. In some embodiments, the recombinase recognition sites are selected from a loxP site, a lox511 site, a lox2272 site, and a FRT site. In other embodiments, the recombinase recognition sites are different. In a further embodiment, the host cell comprises a gene capable of expressing a Cre recombinase.

In one embodiment, the vector comprises a first gene encoding a light chain of an antibody or a heavy chain of an antibody of the invention, and a second gene encoding a light chain of an antibody or a heavy chain of an antibody of the invention.

In some embodiments, the vector further comprises an X-box-binding-protein 1 (mXBP1) gene capable of further enhancing protein production/protein secretion through control of the expression of genes involved in protein folding in the endoplasmic reticulum (ER). (See, e.g. Ron D, and Walter P. Nat Rev Mol Cell Biol. 8:519-529 (2007)).

Any cell is suitable for expressing a recombinant nucleic acid sequence of the invention. Cells used in the invention include mammalian cells such as non-human animal cells, human cells, or cell fusions such as, for example, hybridomas or quadromas. In certain embodiments, the cell is a human, monkey, hamster, rat or mouse cell. In other embodiments, the cell is eukaryotic and is selected from the following cells: CHO (e.g. CHO K1, DXB-11 CHO, Veggie-CHO), COS (e.g. COS-7), retinal cells, Vero, CV1, kidney (e.g. HEK293, 293 EBNA, MSR 293, MDCK, HaK, BHK21), HeLa, HepG2, WI38, MRC 5, Colo25, HB 8065, HL-60, Jurkat, Daudi, A431 (epidermal), CV-1, U937, 3T3, L cell, C127 cell, SP2/0, NS-0, MMT cell, tumor cell, and a cell line derived from an aforementioned cell. In some embodiments, the cell comprises one or more viral genes, e.g. a retinal cell that expresses a viral gene (e.g. a PER.C6® cell).

In an even further aspect, the invention relates to a recombinant mammalian host cell, such as a transfectoma, which produces an immunoglobulin, such as an antibody or a bispecific molecule. Examples of such host cells include engineered mammalian cells such as CHO or HEK cells. For example, in one embodiment, the present invention provides a cell comprising a nucleic acid stably integrated into the cellular genome that comprises a sequence coding for expression of an antibody comprising a recombinant polypeptide of the present invention. In another embodiment, the present invention provides a cell comprising a non-integrated (i.e., episomal) nucleic acid, such as a plasmid, cosmid, phagemid, or linear expression element, which comprises a sequence coding for expression of an antibody comprising the recombinant polypeptide of the invention. In other embodiments, the present invention provides a cell line produced by stably transfecting a host cell with a plasmid comprising an expression vector of the invention.

Thus, in one aspect, the invention provides a cell containing (a) a recombinant polynucleotide that encodes an exogenously-added mammalian GPT gene and (b) a polynucleotide that encodes a multi-subunit protein. In some embodiments, the exogenously-added GPT gene is 90% identical to the nucleic acid sequence of SEQ ID NO: 2, non-limiting examples of which are provided in SEQ ID NOs:11-17, and the multi-subunit protein is an antibody. In other embodiments, the cell also contains an exogenously-added GPT gene, and regulatory elements. In one embodiment, the cell is a mammalian cell, such as a CHO cell used in the manufacture of biopharmaceuticals.

In another aspect, the invention provides a cell line derived from the cell described in the previous aspect. By "derived from", what is meant is a population of cells clonally descended from an individual cell and having some select qualities, such as the ability to produce active protein at a given titer, or the ability to proliferate to a particular density. In some embodiments, the cell line, which is derived from a cell harboring the recombinant polynucleotide encoding a mammalian GPT gene and a polynucleotide encoding a multi-subunit protein, is capable of producing the multi-subunit protein at a titer of at least 3 grams per liter of media (g/L), at least 5 g/L, or at least 8 g/L. In some embodiments, the cell line can attain an integrated cell density (ICD) that is at least 30% greater, at least 50% greater, at least 60% greater, or at least 90% greater than the integrated cell density attainable by a cell line derived from what is essentially the same cell but without the recombinant polynucleotide encoding GPT.

A method for amplifying the GOI is provided. The exemplified methods apply increasing concentrations of tunicamycin to a eukaryotic GPT expression system, thus amplifying the gene copy of a GOI operably linked to an exogenously-added mammalian GPT gene.

Proteins of Interest

A nucleic acid sequence encoding a protein of interest can be conveniently integrated into a cell comprising an Tn resistance marker gene and an IRES, and optionally flanked by recombinase recognition sites. Any protein of interest suitable for expression in mammalian cells can be used, however glycoproteins will especially benefit from the methods of the invention. For example, the protein of interest can be an antibody or antigen-binding fragment thereof, a bispecific antibody or fragment thereof, a chimeric antibody or fragment thereof, an ScFv or fragment thereof, an Fc-tagged protein (e.g. Trap protein) or fragment thereof, a growth factor or a fragment thereof, a cytokine or a fragment thereof, or an extracellular domain of a cell surface receptor or fragment thereof.

Glycoproteins with asparagine-linked (N-linked) glycans are ubiquitous in eukaryotic cells. Biosynthesis of these glycans and their transfer to polypeptides takes place in the endoplasmic reticulum (ER). N-glycan structures are further modified by a number of glycosidases and glycosyl-transferases in the ER and the Golgi complex. Protein production using the invention is directed at consistency of the native N-glycan structure in order to eliminate immunogenic epitopes ("glycotopes").

Using the methods of the invention, recombinant protein lots display favorable characteristics. HPLC (with fluorescent detection) of replicate protein production batches demonstrated that the glycoproteins had uniform expression and glycosylation patterns, as exemplified in FIGS. 7-8 herein. A method of glycosylating a N-glycan protein substrate is provided, whereas a mammalian host cell encoding a nucleic acid molecule comprising a mammalian tunicamycin (Tn)-resistance gene operably linked to a gene encoding the protein substrate in need of glycosylation is provided; the cell is cultured in the presence of a first concentration of Tn; a cell population expressing at least one copy of the Tn-resistance gene is isolated; the cell population is cultured in the presence of increasing concentrations of Tn; and the N-glycan protein substrate is isolated from the cell culture. The N-glycan content of the protein substrate may be evaluated for the presence of monosaccharides and oligosaccharides by any method known in the art.

Detailed structural analysis of glycan-linked proteins may be correlated to functional features of the protein. Such analysis characterizing protein glycosylation typically involves several steps: i) an enzymatic or chemical release of the attached glycans; ii) derivatization of the released glycans via reductive amination with aromatic or aliphatic amines or permethylation; iii) analysis of the glycans. Many variations of analyzing glycosylation patterns in known to the skilled person. Glycoproteins may carry several types of glycoforms occupying various sites in specific quantities, and therefore their complexity may make it difficult to reproduce in certain production methods. Consistency of type and quantity of glycoform is measurable and represents a desirable outcome for therapeutic protein production.

Host Cells and Transfection

The mammalian host cells used in the methods of the invention are eukaryotic host cells, usually mammalian cells, including, e.g. CHO cells and mouse cells. In one embodiment, the invention provides a cell comprising a nucleic acid sequence that encodes a Tn resistance marker protein derived from Cricetulus griseus (Chinese hamster) (as set forth in SEQ ID NO:3), or a homolog or variant thereof. In some embodiments, the cell comprises multiple gene copies of the Tn resistance marker gene. In other embodiments, the invention provides a nucleic acid sequence that encodes a Tn resistance marker protein derived from human (SEQ ID NO:4), Rhesus monkey (SEQ ID NO:5), chimpanzee (SEQ ID NO:6), dog (SEQ ID NO:7), guinea pig (SEQ ID NO:8), rat (SEQ ID NO:9) or mouse (SEQ ID NO:10).

The invention includes a mammalian host cell transfected with an expression vector of the invention. Transfected host cells include cells that have been transfected with expression vectors that comprise a sequence encoding a protein or polypeptide of interest. Expressed proteins will typically be secreted into the culture medium, depending on the nucleic acid sequence selected, but may be retained in the cell or deposited in the cell membrane. Various mammalian cell culture systems can be employed to express recombinant proteins. Examples of suitable mammalian host cell lines include the COS-7 lines of monkey kidney cells, described by Gluzman (1981) Cell 23:175, and other cell lines capable of expressing an appropriate vector including, for example, CV-1/EBNA (ATCC CRL 10478), L cells, C127, 3T3, CHO, HeLa and BHK cell lines. Other cell lines developed for specific selection or amplification schemes will also be useful with the methods and compositions provided herein. In one embodiment of the invention, the cell is a CHO cell line designated K1 (i.e. a CHO K1 cell). In order to achieve the goal of high volume production of recombinant proteins, the host cell line should be pre-adapted to bioreactor medium in the appropriate case.

Several transfection protocols are known in the art, and are reviewed in Kaufman (1988) Meth. Enzymology 185: 537. The transfection protocol chosen will depend on the host cell type and the nature of the GOI, and can be chosen based upon routine experimentation. The basic requirements of any such protocol are first to introduce DNA encoding the protein of interest into a suitable host cell, and then to identify and isolate host cells which have incorporated the heterologous DNA in a relatively stable, expressible manner.

Certain reagents useful for introducing heterologous DNA into a mammalian cell include Lipofectin™ Reagent and Lipofectamine™ Reagent (Gibco BRL, Gaithersburg, Md.). Both of these reagents are commercially available reagents used to form lipid-nucleic acid complexes (or liposomes) which, when applied to cultured cells, facilitate uptake of the nucleic acid into the cells.

The transfection protocol chosen and the elements selected for use therein will depend on the type of host cell used. Those of skill in the art are aware of numerous different protocols and host cells, and can select an appropriate system for expression of a desired protein, based on the requirements of the cell culture system used. In a further aspect, the invention relates to an expression vector encoding a polypeptide, including but not limited to, an antibody, bispecific antibody, chimeric antibody, ScFv, antigen-binding protein, or Fc fusion protein. Such expression vectors may be used for recombinant production of polypeptides using the methods and compositions of the invention.

Other features of the invention will become apparent in the course of the following descriptions of exemplary embodiments which are given for illustration of the invention and are not intended to be limiting thereof.

EXAMPLES

The following examples are put forth so as to provide those of ordinary skill in the art how to make and use the methods and compositions described herein, and are not intended to limit the scope of what the inventors regard as their invention. Efforts have been made to ensure accuracy with respect to numbers used (e.g., amount, temperature, etc.) but some experimental error and deviation should be accounted for. Unless indicated otherwise, parts are parts by weight, molecular weight is average molecular weight, temperature is in degrees Centigrade, and pressure is at or near atmospheric.

Example 1

Selection Efficiency of Transfectant Cells Expressing GPT

Modified CHO K1 cells were transfected with a plasmid vector containing CHO-GPT (SEQ ID NO: 2), human GPT (SEQ ID NO:12) or a plasmid vector containing a hygromycin phosphotransferase (Hpt, Hygromycin resistant gene); e.g. the selectable marker gene (CHO-GPT or hpt) was transcriptionally linked to a downstream eGFP gene via an IRES sequence, in their respective vectors. For example, each plasmid was constructed to contain the following gene sequences, in 5' to 3' direction: a Lox site, a SV40 late promoter, either CHO-GPT (or Hpt), IRES, enhanced green fluorescent protein (eGFP), and a second Lox site. Purified recombinant plasmids were transfected together with a plasmid that expresses Cre recombinase, into a modified CHO host cell line containing: from 5' to 3', a lox site, YFP, and a second lox site, at a transcriptionally active locus. Consequently, the host CHO cell can be isolated by flow cytometry as a green-positive or a yellow-negative cell. When the recombinant plasmid expressing eGFP (transcriptionally regulated by the GPT or hpt genes) was transfected together with a plasmid expressing the Cre recombinase, recombination mediated by the Cre recombinase results in the site-specific integration of the GPT/eGFP cassette at the chromosomal locus containing the lox sites and replacement of the YFP gene occurs (i.e. a green-positive cell). Should the eGFP integrate randomly, both green-positive and yellow positive cells will result.

Figure 4A:
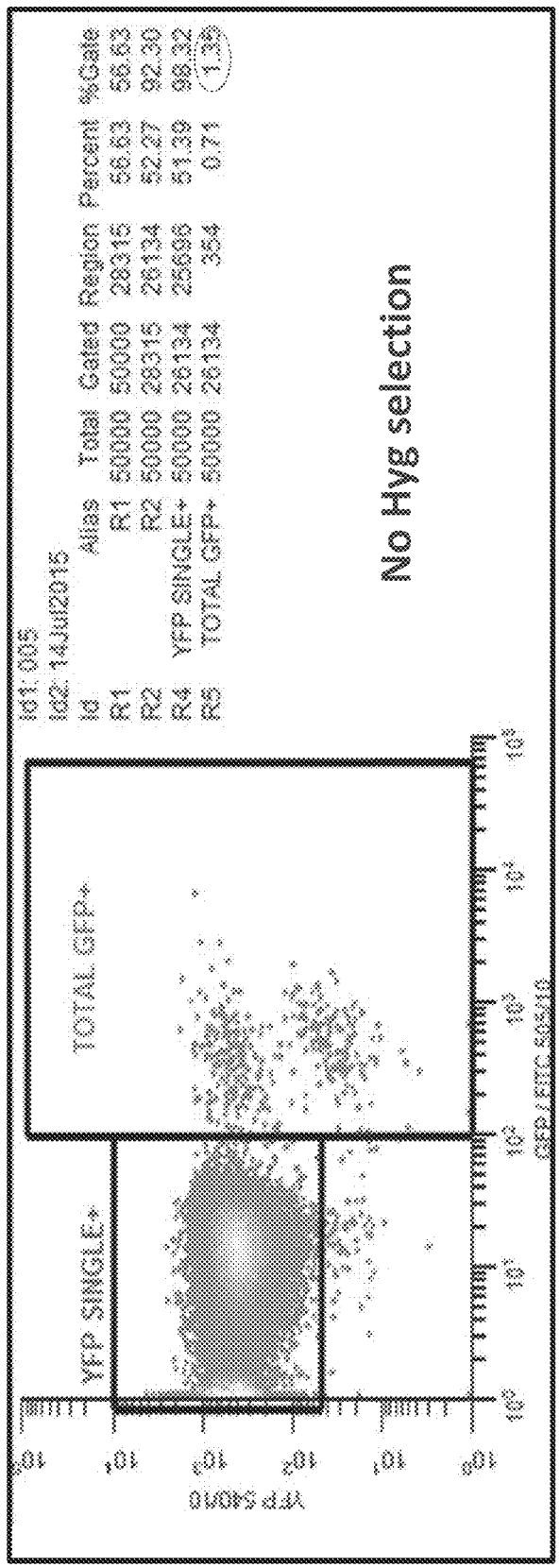
FIGS. 4A to 4B show FACS scatterplots representing various parameters of Hygromycin selectivity. Modified CHO cells comprise a YFP gene flanked by lox sites. Selection markers (antibiotic resistance gene and eGFP) flanked by lox sites incorporate at the YFP site and replace YFP via targeted integration with Cre recombinase. Random integrants express both YFP and eGFP
Figure 4B:
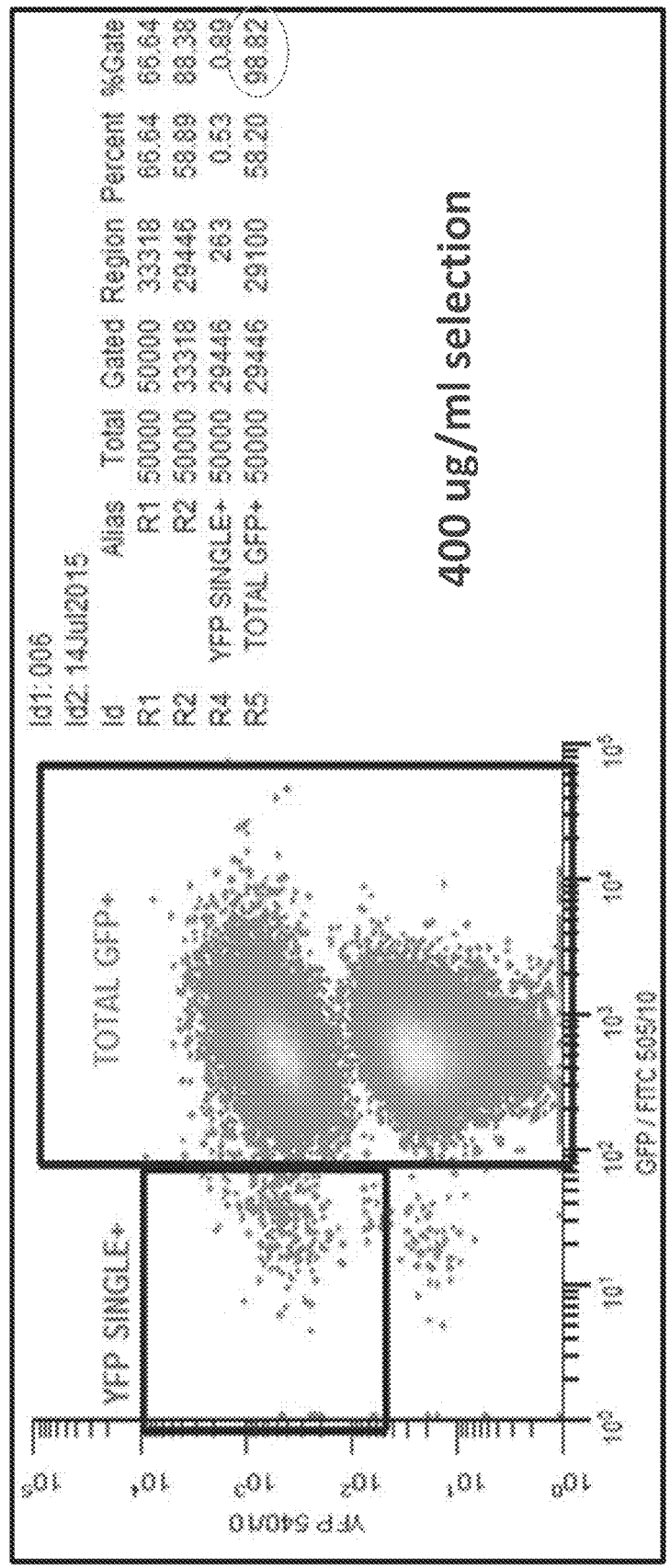
Figure 5A:
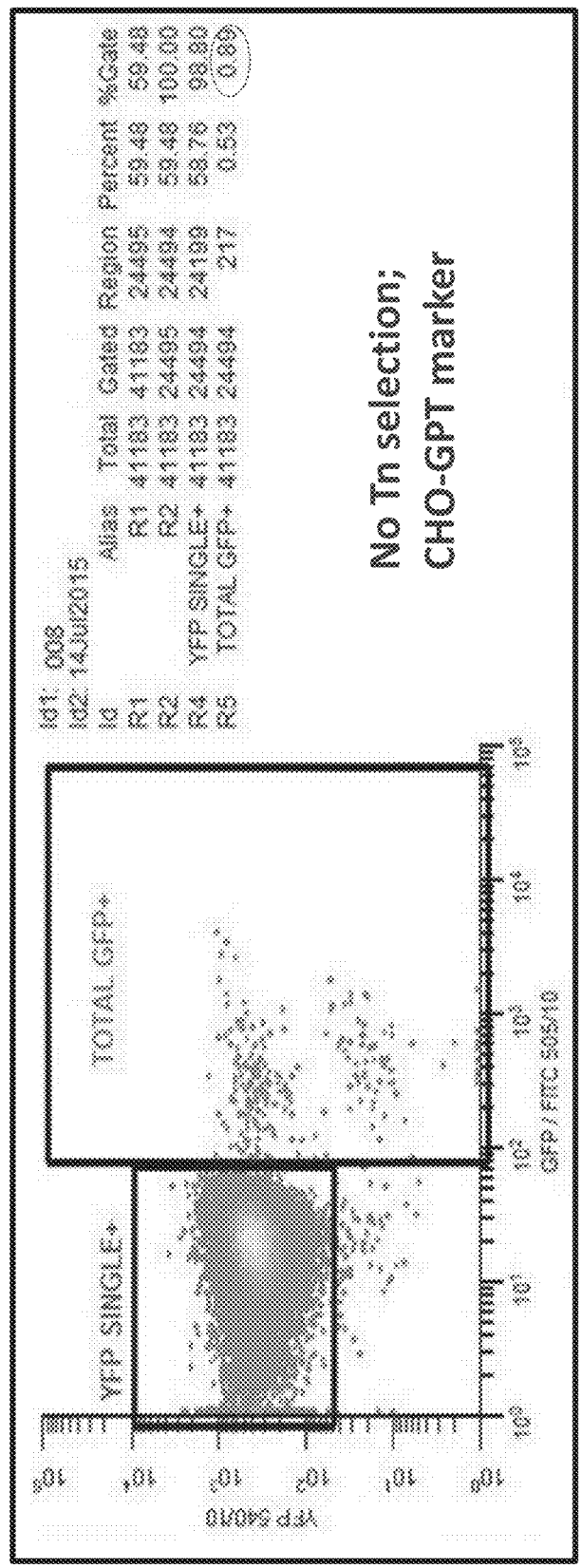
FIGS. 5A to 5F show FACS scatterplots representing various parameters of Tunicamycin (Tn) selectivity. Modified CHO cells comprise a YFP gene flanked by lox sites. Selection markers (antibiotic resistance gene and eGFP) flanked by lox sites incorporate at the YFP site and replace YFP via targeted integration with Cre recombinase. Random integrants express both YFP and eGFP
Figure 5B:
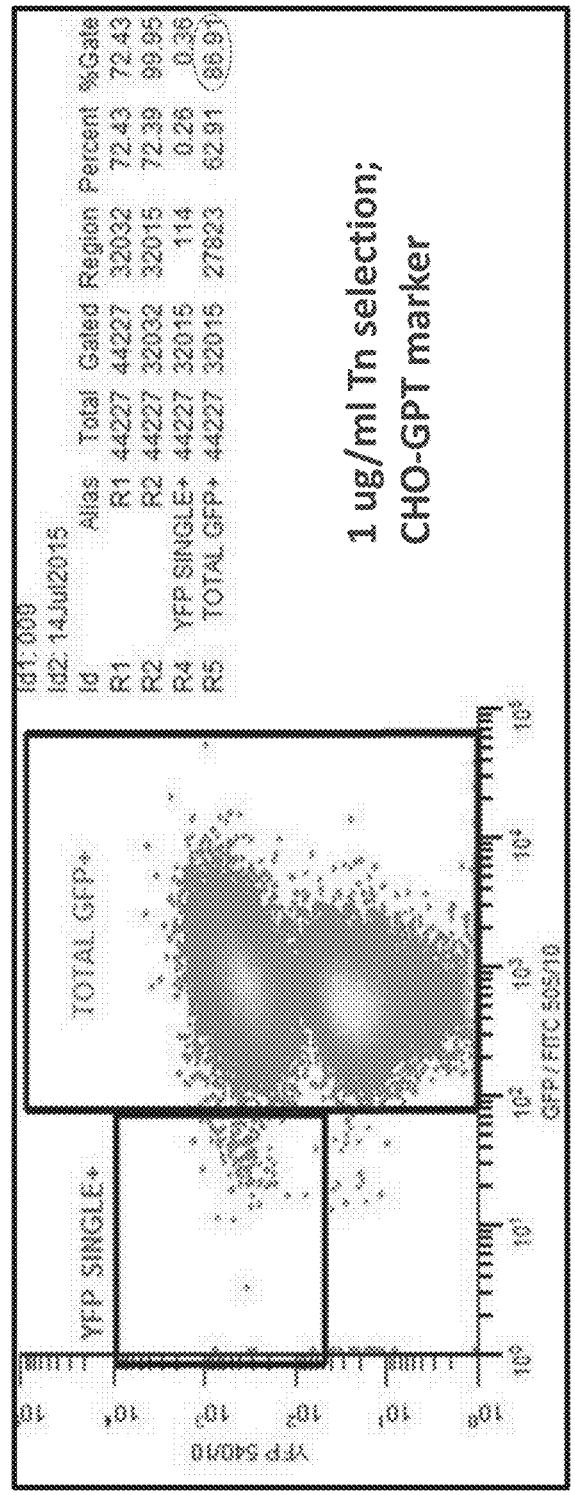
Figure 5C:
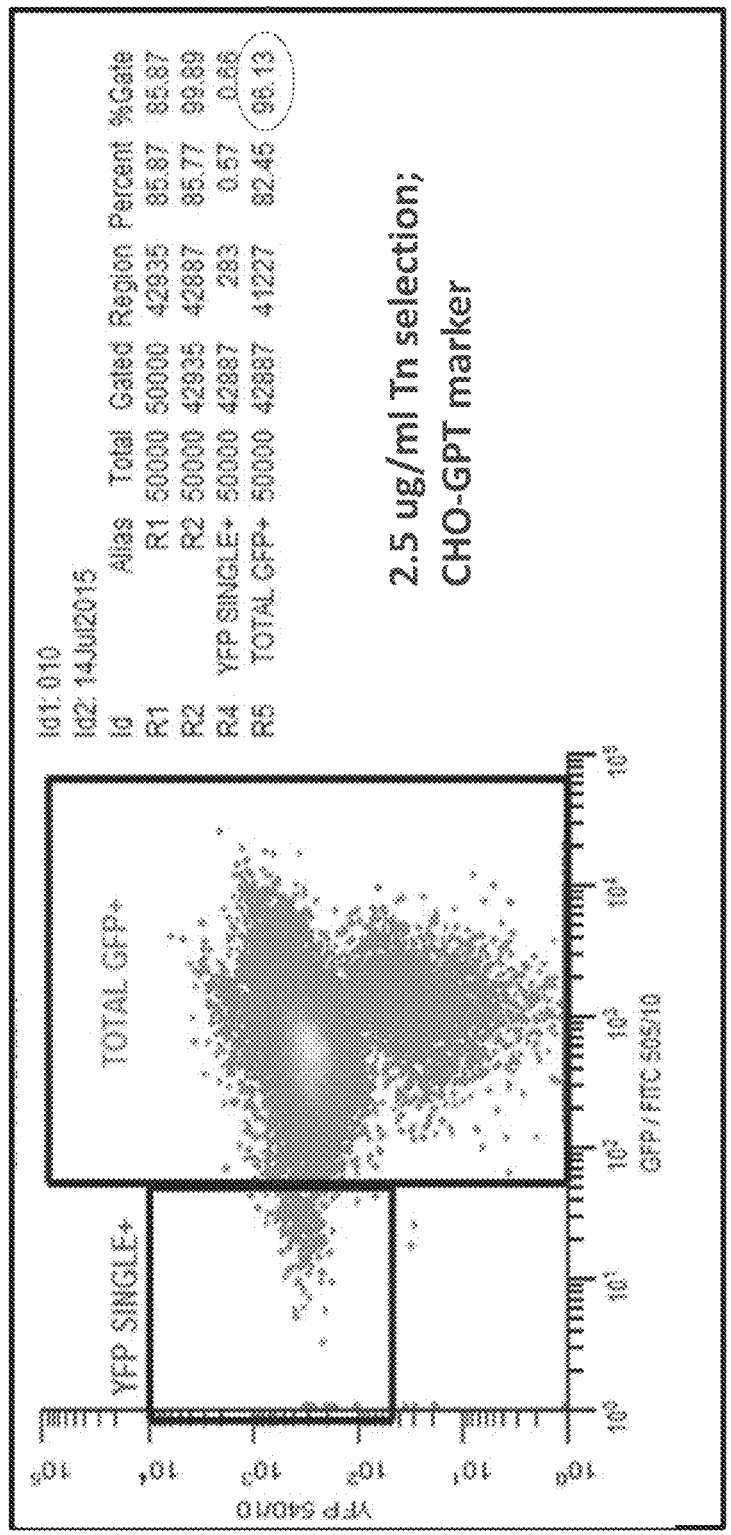
Figure 5D:
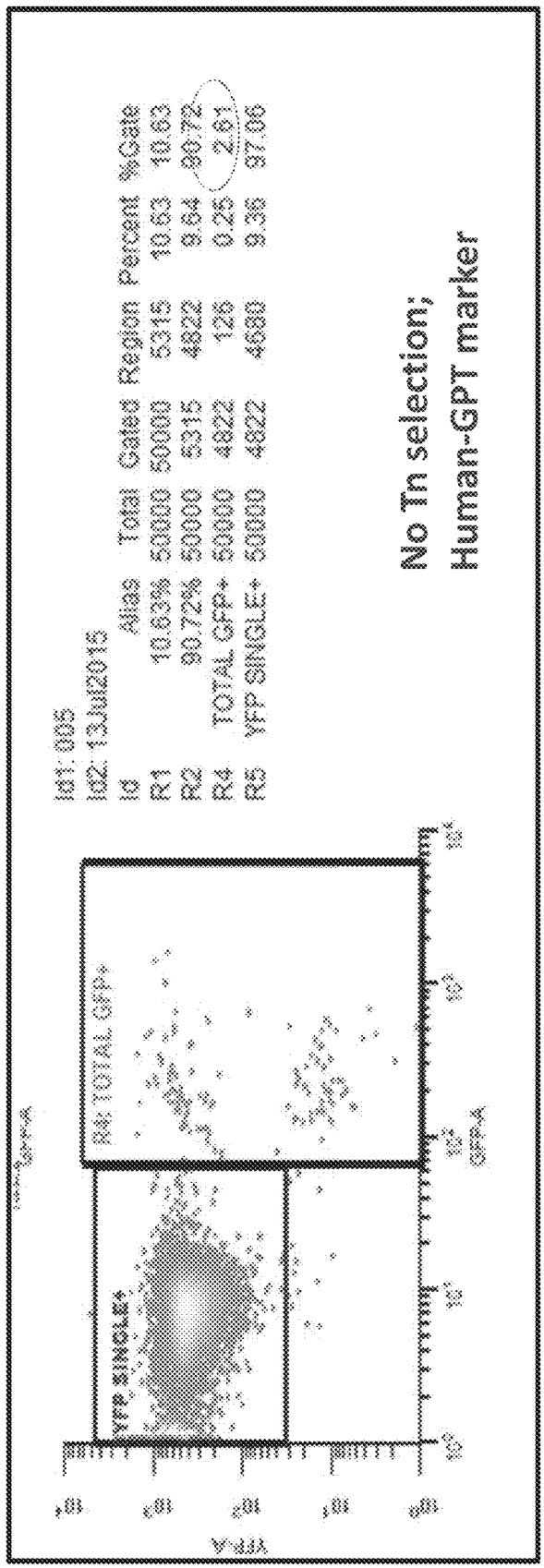
Figure 5E:
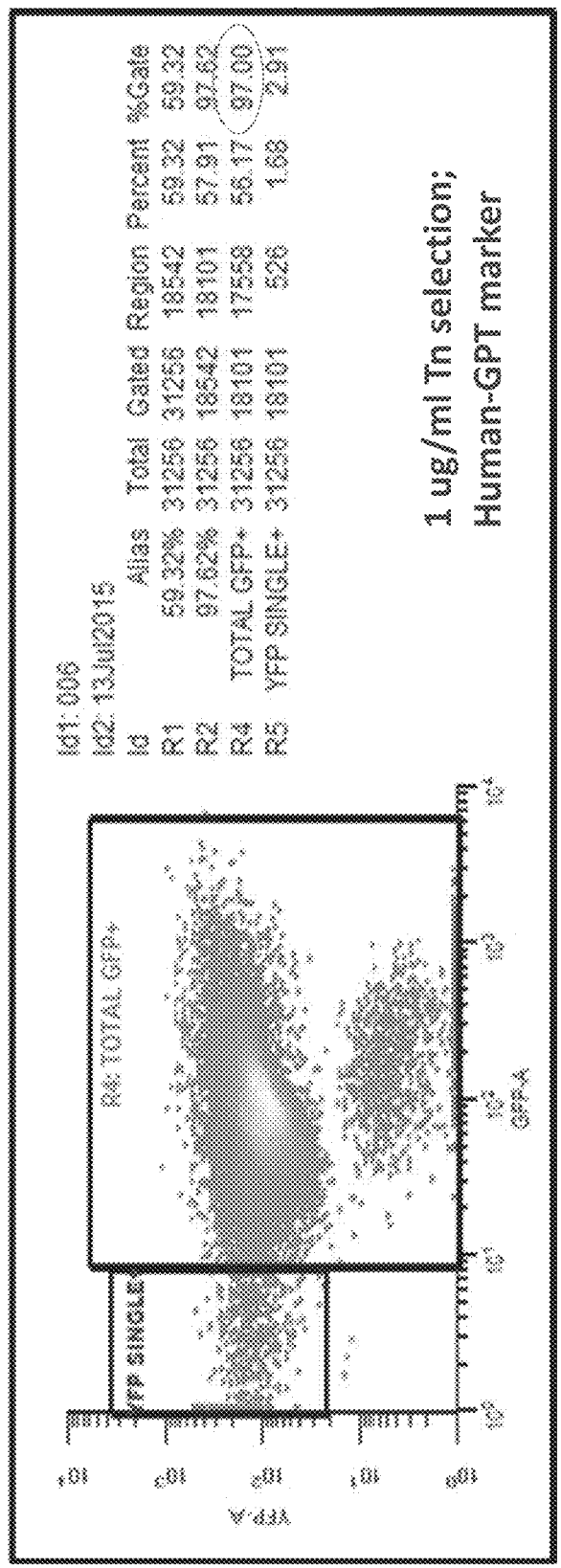
Figure 5F:
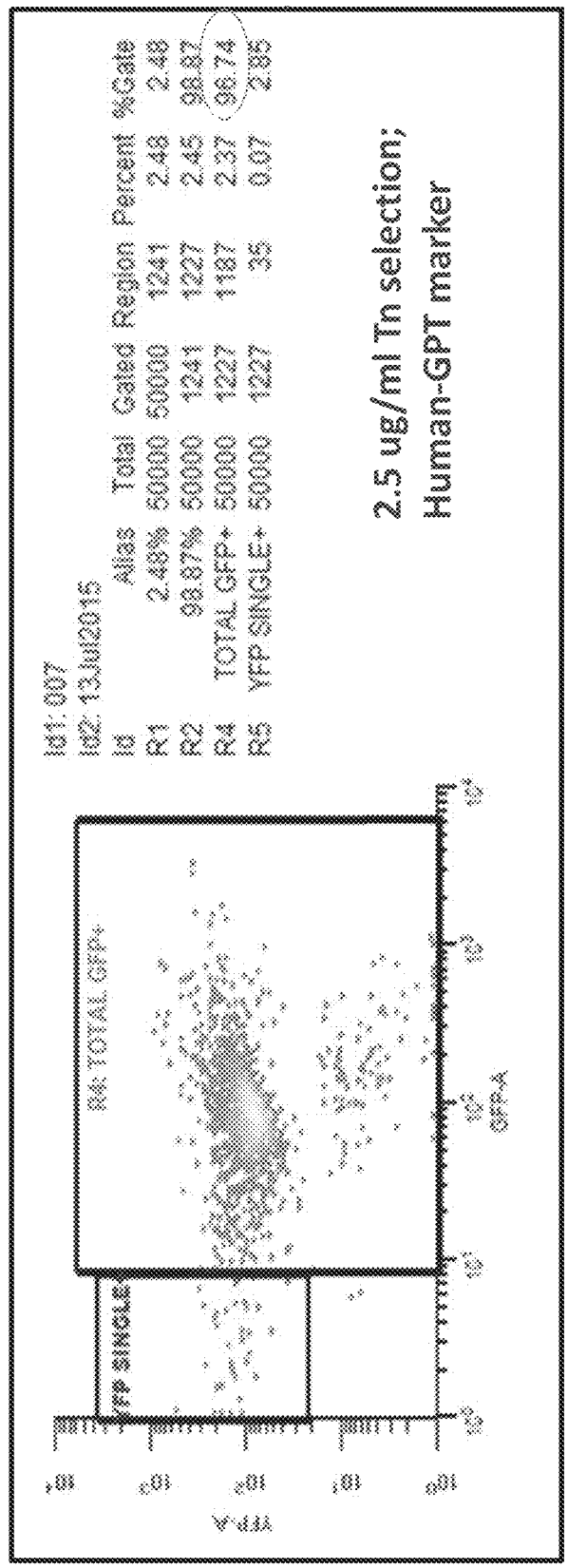

Cell populations were either incubated with 0, 1µg/ml, 2.5 µg/ml or 5µg/ml tunicamycin (Tn) or 400 µg hygromycin (Hyg), as outlined in Table 2. Observed recombinant populations (ORPs) were measured by fluorescent-activated cell sorting (FACS) analysis. Cells were sorted to quantitate each population of cells, and selection efficiency was calculated for cells expressing only GFP and not YFP (FIG. 4 or 5).

Selection efficiency (percent population of surviving cells expressing GFP) was compared between cell pools resistant to either Tn or Hyg (Table 2).

TABLE 2

Selection Efficiency

| Hpt or GPT | Cre | Selection agent (ug/ml Hyg or Tn) | Selection efficiency % (Total GFP+) |
|---|---|---|---|
| Hpt | + | - | 1.35 |
| Hpt | + | + (400 Hyg) | 98.8 |
| choGPT | + | - | 0.89 |
| choGPT | + | + (1Tn) | 86.9 |
| choGPT | + | + (2.5 Tn) | 96.1 |
| hGPT | + | - | 2.6 |
| hGPT | + | + (1Tn) | 97 |
| hGPT | + | + (2.5 Tn) | 96.7 |

It was observed that tunicamycin selection is as efficient as hygromycin selection. Both CHO-GPT and human GPT were efficient at selection of integrants in the presence of 1 ug/ml or 2.5 ug/ml Tunicamycin.

Example 2

Amplification of the Gene Product

Incremental selection was done by applying increasing concentrations of tunicamycin to the GPT expression system. CHO K1 cells were transfected with a plasmid vector containing the CHO-GPT gene (SEQ ID NO: 2) as above. The plasmid contains in 5' to 3' direction, a first Lox site, a SV40 late promoter, the CHO-GPT gene, an IRES, eGFP, and a second Lox site. The CRE-lox sites direct integration of the gene of interest into the genome resulting in a stable transfectant pool of cells with at least one GPT insertion per cell. (More integrants may occur due to random integration, as seen above). CHO cells were initially cultured in the presence of 1 µg/ml tunicamycin (Tn). Transfectants were then selected from the stable pool (named Cell Pool 2) and subsequently expanded in the presence of 1 µg/ml, 2.5 µg/ml or 5 µg/ml Tn. Selection rounds were conducted to identify cell populations capable of enhanced expression (multiple copies) of eGFP. The random integration events increased greatly, in the presence of 2.5 µg/ml or 5 µg/ml Tn.

Figure 6A:
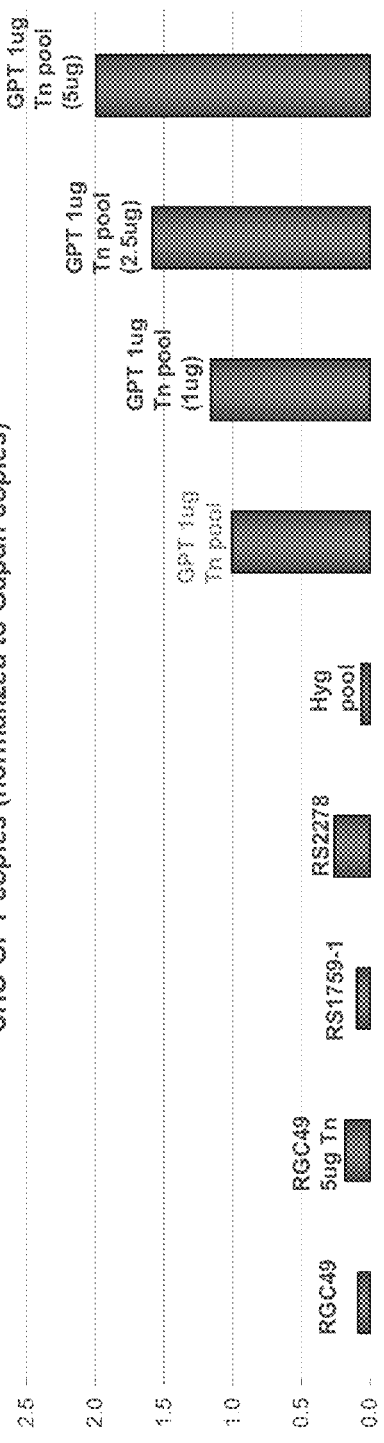
FIGS. 6A and 6B show GPT expressing cell pools compared to non-GPT expressing pools in their relative ability to enhance expression of an operably linked GOI, such as eGFP.

Copy number of gene product, either CHO GPT, eGFP or mGapdh (normalized control), was measured using standard qPCR methods. Copy number of eGFP in the cells from the 1 µg/ml Tn-resistant pool incubated further with 2.5 ug/ml Tn was at least 2 times the copy number of eGFP from the 1 µg/ml Tn-resistant pool incubated further with 1 µg/ml Tn. The gene copy number increased further when a 1 µg/ml Tn-treated pool was incubated further with 5 µg/ml Tn. The increase in gene copy number for eGFP correlates with the increased gene copy of CHO-GPT. (See FIGS. 6A and 6B.)

Figure 6B:
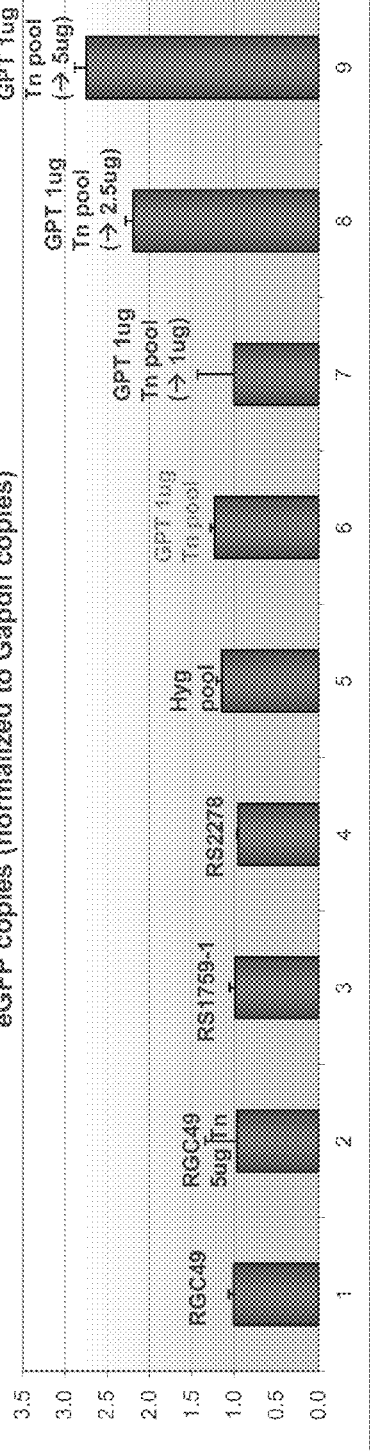
Figure 8:
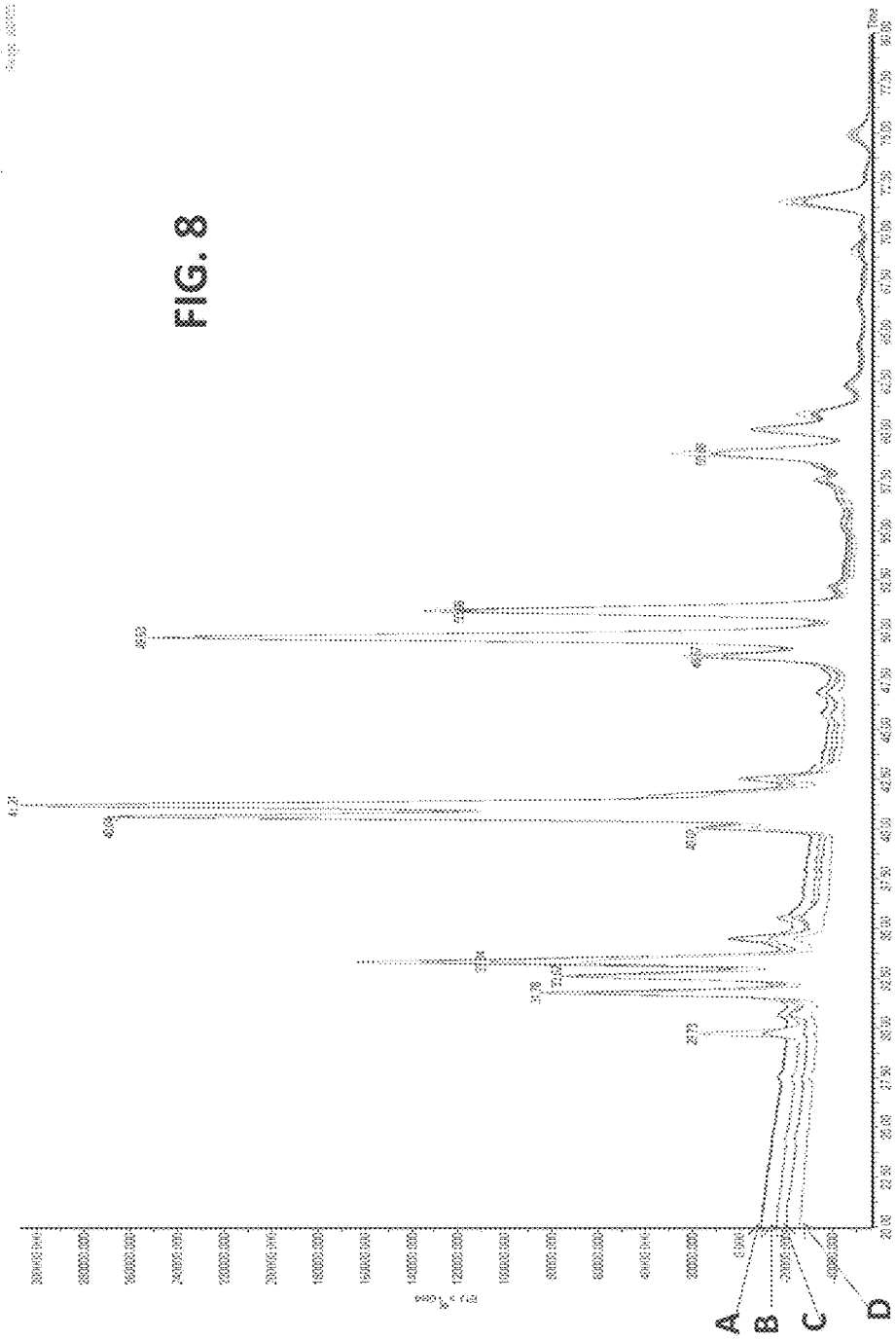
FIG. 8 illustrates the overlapping glycosylation profile of Fc-fusion protein 1 (FcFP1) sampled from (A) Lot B10002M410, (B) Lot 110728, (C) Lot 110728-01, and (D) Lot 110728-02. The glycoprofiles of each protein produced from the GPT lots are compatible with the reference standard protein and the major glycoform species are consistently produced. It is apparent that no new and unique species of glycoforms were produced in the GPT lots compared to the reference standard protein.

To determine whether increase in gene copy number translates to increased protein expression, the mean fluorescent intensity (MFI) was measured by FACS for the same cell pools expressing GPT and eGFP that were treated with multiple rounds of Tn selection, namely 1, 2.5 or 5 µg Tn (see e.g. samples 7, 8, and 9 in FIG. 6B). The comparison of eGFP expression for these cell pools is represented in Table 3.

The cell pool expressing GPT that was subjected to a second round of selection with 5 µg Tn resulted in just greater than 2.5 times the productive output compared to 1 µg Tn treatment, and 1.5 times the productive output compared to 2.5µg Tn treatment, with respect to eGFP production (Table 3).

TABLE 3 eGFP protein production

| GPT 1 ug pool + Second Tn (µg) Treatment | MFI |
|---|---|
| 1 µg | 1098 |
| 2.5 µg | 1867 |
| 5 µg | 2854 |

Without being bound by any one theory, incremental increases in the concentration of Tn amplified the selective pressure to the cells in a controlled manner, thus increasing the productive output.

Tn-resistant expression vectors were also employed in further experiments, described below, to test the effects of Tn selection on glycosylation patterns.

Example 3

Expression and Glycosylation Profile of an Exemplary Dimeric Protein

CHO cells expressing a "Trap" protein (Fc fusion protein-1, hereinafter referred to as FcFP1) were transfected with a GPT-containing expression vector. The plasmid has, in 5' to 3' direction, a Lox site, a SV40 late promoter, a Tn-resistant gene (CHO-GPT), an IRES eGFP, SV40 polyA and a second Lox site. 1 μg/mL Tn or 5 μg/mL Tn was used for selection of the GPT selectable marker. The selected pools cells were expanded in suspension cultures in serum-free production medium. GPT transfection was confirmed by expression of eGFP by FACS analysis. Pellets collected from selected pools were sent for copy number analysis for GPT expression and a 12 day productivity assay was set up to determine the expression level of FcFP1 in pools selected with different concentrations of Tunicamycin.

FcFP1 was selected for its complex glycosylation pattern, having an abundance of glycosylation sites. To determine glycosylation profiles, cells expressing FcF1 protein were expanded in cell culture under standard protocol (no Tn) or conditions of Tn treatment as represented in Table 4, then protein was isolated and purified.

on glycosylation profiles. The production lots were also compared to a reference standard which represents a therapeutically acceptable batch of protein. Representative glycan analysis is shown in FIGS. 7A-7D. Each lot, compared to the reference lot, consistently produces the same number of peaks, relative shape and relative intensity. An overlap of each chromatogram (FIG. 8) indicates that no unique or unusual peaks are uncovered.

Oligosaccharide profiling was done by well-known HPLC methods against the reference standard lot for the FcFP1 protein. Levels of sialylation were measured for the FcFP1 trap protein lots and the Z-number was calculated for each lot (3 replicates). Z-number represents the measure of variation between lots. The Z-number takes into account the relative number of peaks, as well as the relative shape and intensity of each peak. For example, the area of each OSA, 1SA, 2SA, 3SA and 4SA peak in FIGS. 7A-7D is quantitated as in Table 5.

TABLE 5

Quantitative Oligosaccharide Analysis

| Protein Lot | Replicate | OSA | 1SA | 2SA | 3SA | 4SA | OS PROFILE (Z-number) |
|---|---|---|---|---|---|---|---|
| Reference B100002M410 | 1 | 6506.43 | 13388.34 | 11268.60 | 5176.21 | 1728.15 | 1.53 |
| | 2 | 5869.80 | 11932.32 | 10159.21 | 4196.10 | 1550.09 | 1.51 |
| | 3 | 6870.18 | 14536.84 | 12090.21 | 5200.58 | 1707.74 | 1.51 |
| | Avg | 6415.47 | 13285.83 | 11172.65 | 4857.63 | 1661.99 | 1.52 ± 0.01 |
| FcFP1 Trap 110728 | 1 | 6159.09 | 9394.92 | 7368.03 | 3074.66 | 675.48 | 1.34 |
| | 2 | 7530.49 | 12117.03 | 9589.08 | 2951.63 | 810.09 | 1.36 |
| | 3 | 5508.95 | 8580.56 | 6902.59 | 3794.81 | 630.79 | 1.34 |
| | Avg | 6399.51 | 10030.84 | 7953.23 | 3074.66 | 705.45 | 1.35 ± 0.01 |
| FcFP1 trap 110728-1 | 1 | 5330.22 | 8149.81 | 6539.33 | 2490.06 | 641.37 | 1.35 |
| | 2 | 5034.39 | 9009.42 | 7059.61 | 2698.05 | 812.21 | 1.40 |
| | 3 | 6222.44 | 10235.08 | 8428.04 | 3276.75 | 848.83 | 1.39 |
| | Avg | 5529.02 | 9131.44 | 7342.33 | 2821.62 | 767.47 | 1.38 ± 0.03 |
| FcFP1 trap 110728-2 | 1 | 6300.77 | 10001.93 | 8109.12 | 3000.96 | 790.99 | 1.36 |
| | 2 | 5999.09 | 9952.47 | 7968.58 | 2885.50 | 717.70 | 1.36 |
| | 3 | 4322.29 | 6176.33 | 5187.48 | 1742.26 | 458.52 | 1.32 |
| | Avg | 5540.72 | 8710.24 | 7088.39 | 2542.91 | 655.74 | 1.35 ± 0.02 |

OS = oligosaccharide;
0SA = zero sialic acid residues;
1SA = one sialic acid residue;
2SA = two sialic acid residues;
3SA = three sialic acid residues;
4SA = four sialic acid residues

TABLE 4

FcFP1 protein production

| Protein | Lot# | Treatment |
|---|---|---|
| FcFP1 Trap | 110728 | None |
| FcFP1 Trap | 110728-1 | 1 μg/ml Tn |
| FcFP1 Trap | 110728-2 | 5 μg/ml Tn |

Detailed glycan analysis was performed using chromatography based on well-known methods for HPLC and fluorescent anthranilic acid (AA) tags (Anumula, and Dhume, *Glycobiology*, 8(7):685-694, 1998), for each lot of glycoprotein to determine whether Tn had a negative impact $$Z \text{ number} = \frac{(Area1SA + 2*Area2SA + 3*Area3SA + 4*Area4SA)}{(Area0SA + Area1SA + Area2SA + Area3SA + Area4SA)}$$

The Z-number calculated for each lot is within an acceptable range compared to the reference lot, therefore each protein lot is understood to achieve the same material as the therapeutic molecule. Since the presence of Tn is known to have a negative effect on glycosylation of N-linked glycoproteins, it was unexpected that protein production would be reliable and consistent, as well as productive, given the conditions of increased selection pressure by Tn.

The present invention may be embodied in other specific embodiments without departing from the spirit or essence thereof.

We claim:

1. An isolated cell comprising i) an exogenously added mammalian tunicamycin (Tn)-resistance gene comprising the nucleic acid sequence of SEQ ID NO: 12, operably linked to at least one regulatory element, and ii) a first exogenously added gene of interest (GOI).

2. The isolated cell of claim 1, wherein the at least one regulatory element is selected from the group consisting of a promoter, ribosome-binding site, and enhancer.

3. The isolated cell of claim 1, further comprising a second exogenously-added gene of interest (GOI).

4. The isolated cell of claim 3, wherein at least one of the first or second exogenously-added GOI is a human gene.

5. The isolated cell of claim 3, wherein at least one of the first or second exogenously added GOI is selected from the group consisting of antibody heavy chain, antibody light chain, antigen-binding fragment, and Fc-fusion protein.

6. The isolated cell of claim 5, wherein said at least one exogenously added GOI is operably linked to a promoter.

7. The isolated cell of claim 3, wherein the first exogenously added GOI and the second exogenously added GOI are independently selected from the group consisting of gene encoding for an antibody light chain or antigen-specific fragment thereof, an antibody heavy chain or antigen-specific fragment thereof, an Fc-fusion protein or a fragment thereof, and a receptor or ligand-specific fragment thereof.

8. The isolated cell of claim 3, wherein at least one of the first or second exogenously added GOI encodes a glycoprotein selected from the group consisting of an antibody light chain or antigen-binding fragment thereof, an antibody heavy chain or antigen-binding fragment thereof, an Fc-fusion protein or a fragment thereof, a ligand, and a receptor or ligand-binding fragment thereof.

9. The isolated cell of claim 3, wherein a recombinase recognition site is present between the first exogenously added GOI and the second exogenously added GOI.

10. The isolated cell of claim 3, further comprising a recombinase recognition site 5' to the first exogenously added GOI and a recombinase recognition site 3' with respect to the second exogenously added GOI.

11. The isolated cell of claim 1, wherein the regulatory element is an exogenously added regulatory element.

12. The isolated cell of claim 1, wherein the cell is a eukaryotic cell.

13. The isolated cell of claim 12, wherein the cell is a mammalian cell.

14. The isolated cell of claim 13, wherein the cell is selected from the group consisting of CHO—K1, COS-7, HEK293, tumor cell, lymphocyte, retinal cell, and stem cell.

15. The isolated cell of claim 13, wherein the cell is a CHO—K1 cell.

16. An isolated cell comprising a mammalian tunicamycin (Tn)-resistance gene, a first exogenously added GOI, and a second exogenously added GOI, wherein the Tn-resistance gene encodes a protein having at least 93% identity to the amino acid sequence of SEQ ID NO: 3, and is operably linked to at least one regulatory element and the first exogenously added GOI; and wherein at least one of the first or second exogenously added GOI is a human gene.

17. The cell of claim 16, wherein the cell is a mammalian cell.

18. The cell of claim 17, wherein the cell is a CHO—K1 cell.

19. The cell of claim 16, wherein the Tn-resistance gene encodes a protein having at least 98% identity to the amino acid sequence of SEQ ID NO: 3.

20. The cell of claim 16, wherein the Tn-resistance gene encodes a protein comprising the amino acid sequence of SEQ ID NO: 3.

21. An isolated cell comprising a mammalian tunicamycin (Tn)-resistance gene, a first exogenously added GOI, and a second exogenously added GOI, wherein the Tn-resistance gene encodes a protein having at least 93% identity to the amino acid sequence of SEQ ID NO: 3, and is operably linked to at least one regulatory element and the first exogenously added GOI; and wherein at least one of the first or second exogenously added GOI encodes a protein selected from the group consisting of an antibody light chain or antigen-binding fragment thereof, an antibody heavy chain or antigen-binding fragment thereof, an Fc-fusion protein or a fragment thereof, a ligand, and a receptor or ligand-binding fragment thereof.

22. The cell of claim 21, wherein the cell is a mammalian cell.

23. The cell of claim 22, wherein the cell is a CHO—K1 cell.

24. The cell of claim 21, wherein the Tn-resistance gene encodes a protein having at least 98% identity to the amino acid sequence of SEQ ID NO: 3.

25. The cell of claim 21, wherein the Tn-resistance gene encodes a protein comprising the amino acid sequence of SEQ ID NO: 3.

26. A method of producing a recombinant protein of interest (POI), wherein the method comprises:
   a) providing a mammalian host cell which comprises a nucleic acid molecule comprising (i) a mammalian tunicamycin (Tn)-resistance gene and (ii) a gene encoding the POI;
   b) culturing the cell of step a) in the presence of a first concentration of Tn;
   c) isolating a cell population expressing at least one copy of the Tn-resistance gene;
   d) culturing the isolated cell population of step c) in the presence of a second concentration of Tn that is increased over the first concentration of Tn in step b), wherein increasing the concentration of Tn increases production of the POI; and
   e) isolating the POI from the cell culture.

27. The method of claim 26, wherein the mammalian Tn-resistance gene comprises a Chinese hamster (*Cricetulus griseus*) Tn-resistance gene or a human Tn-resistance gene.

28. The method of claim 26, wherein the POI is selected from the group consisting of antibody heavy chain, antibody light chain, antigen-binding fragment, and Fc-fusion protein.

29. The method of claim 26, wherein the first concentration of Tn is 1 µg/mL.

30. The method of claim 26, further comprising culturing the cell population of step d) in the presence of a third concentration of Tn prior to step e), wherein said third concentration of Tn is increased over the second concentration of Tn in step d), and wherein increasing the concentration of Tn increases production of the POI.

31. The method of claim 30, wherein the second concentration of Tn is 2.5 pg/ml, and the third concentration is 5 pg/mL.

32. The method of claim 26, wherein the second concentration of Tn is 2.5 pg/ml or 5 pg/mL.

33. A method of glycosylating a N-glycan protein substrate, wherein the method comprises:
   a) providing a mammalian host cell encoding a nucleic acid molecule comprising a mammalian tunicamycin (Tn)-resistance gene operably linked to a gene encoding the protein substrate in need of glycosylation;
   b) culturing the cell of step a) in the presence of a first concentration of Tn;
   c) isolating a cell population expressing at least one copy of the Tn-resistance gene;
   d) culturing the isolated cell population of step c) in the presence of a second concentration of Tn that is increased over the first concentration of Tn in step b), wherein increasing the concentration of Tn increases production of the protein substrate; and
   e) isolating the protein substrate from the cell culture.

34. A method of producing a recombinant protein of interest (POI), wherein the method comprises:
   a) providing a mammalian host cell which comprises a nucleic acid molecule comprising (i) a mammalian tunicamycin (Tn)-resistance gene and (ii) a gene encoding the POI;
   b) culturing the cell of step a) in the presence of sequentially increasing concentrations of Tn, wherein increasing the concentration of Tn increases production of the POI in the cell; and
   c) isolating the POI from the cell culture.

35. The method of claim 34, wherein the mammalian Tn-resistance gene comprises a Chinese hamster (*Cricetulus griseus*) Tn-resistance gene or a human Tn-resistance gene.

36. The method of claim 34, wherein the POI is selected from the group consisting of antibody heavy chain, antibody light chain, antigen-binding fragment, and Fc-fusion protein.

37. The method of claim 34, wherein the first of the sequentially increasing concentrations of Tn is 1 pg/mL.

38. The method of claim 37, wherein the sequentially increasing concentrations of Tn comprises a second and third concentration of Tn.

39. The method of claim 38, wherein the second concentration of Tn is 2,5 pg/ml, and the third concentration is 5 pg/mL.

40. The method of claim 37, wherein the increasing concentrations of Tn comprises a second concentration of Tn, wherein the second concentration of Tn is 2.5 pg/ml or 5 pg/mL.

41. A method of glycosyiating a N-Glycan protein substrate, wherein the method comprises:
   a) providing a mammalian host cell which comprises a nucleic acid molecule comprising (i) a mammalian tunicamycin (Tn)-resistance gene and (ii) a gene encoding the protein substrate in need of glycosylation;
   b) culturing the cell of step a) in the presence of sequentially increasing concentrations of Tn, wherein increasing the concentration of Tn increases production of the POI in the cell; and
   c) isolating the protein substrate from the cell culture.

\* \* \* \* \*

SEQUENCE LISTING

<160> NUMBER OF SEQ ID NOS: 17

<210> SEQ ID NO 1
<211> LENGTH: 6964
<212> TYPE: DNA
<213> ORGANISM: Artificial Sequence
<220> FEATURE:
<223> OTHER INFORMATION: Synthetic

<400> SEQUENCE: 1

| | | | | | |
|---|---|---|---|---|---|
| aagcttatac | tcgagctcta | gattgggaac | ccgggtctct | cgaattcgag atctagttta | 60 |
| aacacgcggc | cgctaatcag | ccataccaca | tttgtagagg | ttttacttgc tttaaaaaac | 120 |
| ctcccacacc | tccccctgaa | cctgaaacat | aaaatgaatg | caattgttgt tgttaacttg | 180 |
| tttattgcag | cttataatgg | ttacaaataa | agcaatagca | tcacaaattt cacaaataaa | 240 |
| gcatttttt | cactgcattc | tagttgtggt | ttgtccaaac | tcatcaatgt atcttatcat | 300 |
| gtctaccggt | ataacttcgt | ataatgtata | ctatacgaag | ttagccggta gggcccctct | 360 |
| cttcatgtga | gcaaaaggcc | agcaaaaggc | caggaaccgt | aaaaaggccg cgttgctggc | 420 |
| gttttttccat | aggctccgcc | ccctgacga | gcatcacaaa | aatcgacgct caagtcagag | 480 |
| gtggcgaaac | ccgacaggac | tataaagata | ccaggcgttt | ccccctggaa gctccctcgt | 540 |
| gcgctctcct | gttccgaccc | tgccgcttac | cggatacctg | tccgcctttc tcccttcggg | 600 |
| aagcgtggcg | ctttctcata | gctcacgctg | taggtatctc | agttcggtgt aggtcgttcg | 660 |
| ctccaagctg | ggctgtgtgc | acgaaccccc | cgttcagccc | gaccgctgcg ccttatccgg | 720 |
| taactatcgt | cttgagtcca | acccggtaag | acacgactta | tcgccactgg cagcagccac | 780 |
| tggtaacagg | attagcagag | cgaggtatgt | aggcggtgct | acagagttct tgaagtggtg | 840 |
| gcctaactac | ggctacacta | gaagaacagt | atttggtatc | tgcgctctgc tgaagccagt | 900 |
| taccttcgga | aaaagagttg | gtagctcttg | atccggcaaa | caaaccaccg ctggtagcgg | 960 |
| tggttttttt | gtttgcaagc | agcagattac | gcgcagaaaa | aaaggatctc aagaagatcc | 1020 |
| tttgatcttt | tctacggggt | ctgacgctca | gtggaacgaa | aactcacgtt aagggatttt | 1080 |
| ggtcatgggc | gcgcctcata | ctcctgcagg | catgagatta | tcaaaaagga tcttaccta | 1140 |
| gatcctttta | aattaaaaat | gaagttttaa | atcaatctaa | agtatatatg agtaaacttg | 1200 |
| gtctgacagt | taccaatgct | taatcagtga | ggcacctatc | tcagcgatct gtctatttcg | 1260 |
| ttcatccata | gttgcctgac | tccccgtcgt | gtagataact | acgatacggg agggcttacc | 1320 |
| atctggcccc | agtgctgcaa | tgataccgcg | agacccacgc | tcaccggctc cagatttatc | 1380 |
| agcaataaac | cagccagccg | gaagggccga | gcgcagaagt | ggtcctgcaa ctttatccgc | 1440 |
| ctccatccag | tctattaatt | gttgccggga | agctagagta | agtagttcgc cagttaatag | 1500 |
| tttgcgcaac | gttgttgcca | ttgctacagg | catcgtggtg | tcacgctcgt cgtttggtat | 1560 |
| ggcttcattc | agctccggtt | cccaacgatc | aaggcgagtt | acatgatccc ccatgttgtg | 1620 |
| caaaaaagcg | gttagctcct | tcggtcctcc | gatcgttgtc | agaagtaagt tggccgcagt | 1680 |
| gttatcactc | atggttatgg | cagcactgca | taattctctt | actgtcatgc catccgtaag | 1740 |
| atgcttttct | gtgactggtg | agtactcaac | caagtcattc | tgagaatagt gtatgcggcg | 1800 |
| accgagttgc | tcttgcccgg | cgtcaatacg | ggataatact | gcgccacata gcagaacttt | 1860 |
| aaaagtgctc | atcattggaa | aacgttttc | ggggcgaaaa | ctctcaagga tcttaccgct | 1920 |
| gttgagatcc | agttcgatgt | aacccactcg | tgcacccaac | tgatcttcag catctttac | 1980 |
| tttcaccagc | gtttctgggt | gagcaaaaac | aggaaggcaa | aatgccgcaa aaaagggaat | 2040 |

```
aagggcgaca cggaaatgtt gaatactcat actcttcctt tttcaatatt attgaagcat    2100
ttatcagggt tattgtctca tgagcggata catatttgaa tgtatttaga aaaataaaca    2160 aatagggtt ccgcgcacat ttccccgaaa agtgccacct gacgtcaggt acacaacttc    2220
gtatagcata cattatacga agttatggta ccaagcctag gcctccaaaa aagcctcctc    2280
actacttctg gaatagctca gaggcagagg cggcctcggc ctctgcataa ataaaaaaaa    2340
ttagtcagcc atggggcgga gaatgggcgg aactgggcgg agttaggggc gggatgggcg    2400
gagttagggg cggactatg gttgctgact aattgagatg catgctttgc atacttctgc    2460
ctgctgggga gcctggggac tttccacacc tggttgctga ctaattgaga tgcatgcttt    2520
gcatacttct gcctgctggg gagcctgggg actttccaca ccggatccac catgtgggcc    2580
ttcccggagt gccgctgcc gctgctggtg aatttgttcg gctcgctgct gggatttgtg    2640
gctactgtga ccctcatccc tgccttccgt agccacttta tcgccgcgcg cctctgtggc    2700
caggacctca acaagctcag ccggcagcag atcccagaat cccagggagt gatctgcggt    2760
gctgttttcc ttatcatcct cttctgcttc atcccttttcc ccttcctgaa ctgctttgtg    2820
gaggagcagt gtaaggcatt ccccaccat gaatttgtgg ccctgatagg tgccctcctt    2880
gccatctgct gcatgatctt cctgggcttc gctgatgatg tactcaatct gcgctggcgc    2940
cataagctgc tgctgcccac agctgcctct ctacctctcc tcatggttta cttcactaac    3000
tttggcaata caaccattgt ggtacccaag cccttccgct ggattcttgg cctgcatttg    3060
gacttgggaa tcctatacta tgtctacatg ggactgcttg cggtgttctg taccaatgcc    3120
atcaacatcc tagcaggaat taatggccta gaggctggtc agtcactagt catctctgct    3180
tctatcattg tcttcaacct ggtagagctg aaggtgatt atcgggatga tcatgtcttt    3240
tccctctact tcatgatacc attttttttt accaccttgg gattgctata ccataactgg    3300
tacccatcac aggtgtttgt gggagatacc ttctgttatt ttgctggcat gacctttgcc    3360
gtggtgggaa tcttgggaca cttcagcaag accatgctac tcttctttat tccacaagtg    3420
ttcaatttcc tctactcgct gcctcagctc cttcacgcca tccctgccc tcgacaccgc    3480 atacccagac tcaatccgaa gacgggcaaa ctggagatga gctattccaa gttcaagacc    3540
aagaacctct cttcttggg cacctttatt ttaaaggtag cagagcgcct ccagctagtg    3600
acagttcacc gaggcgagag tgaggatggt gccttcactg aatgtaacaa catgaccctc    3660
atcaacttgc tactcaaaat ctttgggccc atacatgaga gaaacctcac actgctcctg    3720
ctgcttttgc agatcctgag cagcgctgtc accttctcca ttcgatacca gcttgtccga    3780
ctcttctatg atgtctgaac gcgtcccccc tctccctccc ccccccctaa cgttactggc    3840
cgaagccgct tggaataagg ccggtgtgcg tttgtctata tgttattttc caccatattg    3900
ccgtcttttg gcaatgtgag ggcccggaaa cctggccctg tcttcttgac gagcattcct    3960
aggggtcttt cccctctcgc caaaggaatg caaggtctgt tgaatgtcgt gaaggaagca    4020
gttcctctgg aagcttcttg aagacaaaca acgtctgtag cgacccttg caggcagcgg    4080 aaccccccac ctggcgacag gtgcctctgc ggccaaaagc cacgtgtata agatacacct    4140
gcaaaggcgg cacaacccca gtgccacgtt gtgagttgga tagttgtgga aagagtcaaa    4200
tggctctcct caagcgtatt caacaagggg ctgaaggatg cccagaaggt accccattgt    4260
atgggatctg atctggggcc tcggtgcaca tgctttacat gtgtttagtc gaggttaaaa    4320
aacgtctagg ccccccgaac cacggggacg tggttttcct ttgaaaaaca cgattgctcg    4380
```

```
aatcaccatg gtgagcaagg gcgaggagct gttcaccggg gtggtgccca tcctggtcga      4440
gctggacggc gacgtaaacg gccacaagtt cagcgtgtcc ggcgagggcg agggcgatgc      4500
cacctacggc aagctgaccc tgaagttcat ctgcaccacc ggcaagctgc ccgtgccctg      4560
gcccaccctc gtgaccaccc tgacctacgg cgtgcagtgc ttcagccgct accccgacca      4620
catgaagcag cacgacttct tcaagtccgc catgcccgaa ggctacgtcc aggagcgcac      4680
catcttcttc aaggacgacg gcaactacaa gacccgcgcc gaggtgaagt tcgagggcga      4740 cacccctggtg aaccgcatcg agctgaaggg catcgacttc aaggaggacg gcaacatcct      4800
ggggcacaag ctggagtaca actacaacag ccacaacgtc tacatcatgg ccgacaagca      4860
gaagaacggc atcaaggtga acttcaagat ccgccacaac atcgaggacg gcagcgtgca      4920
gctcgccgac cactaccagc agaacacccc catcggcgac ggccccgtgc tgctgcccga      4980
caaccactac ctgagcaccc agtccgccct gagcaaagac cccaacgaga gcgcgatca       5040 catggtcctg ctggagttcg tgaccgccgc cgggatcact ctcggcatgg acgagctgta      5100
caagtaatcg gccgctaatc agccatacca catttgtaga ggttttactt gctttaaaaa      5160
acctcccaca cctcccccctg aacctgaaac ataaaatgaa tgcaattgtt gttgttaact      5220
tgtttattgc agcttataat ggttacaaat aaagcaatag catcacaaat ttcacaaata      5280
aagcattttt ttcactgcat tctagttgtg gtttgtccaa actcatcaat gtatcttatc      5340
atgtcggcgc gttgacattg attattgact agttattaat agtaatcaat tacggggtca      5400
ttagttcata gcccatatat ggagttccgc gttacataac ttacggtaaa tggcccgcct      5460
ggctgaccgc ccaacgaccc ccgcccattg acgtcaataa tgacgtatgt tcccatagta      5520
acgccaatag ggactttcca ttgacgtcaa tgggtggagt atttacggta aactgcccac      5580
ttggcagtac atcaagtgta tcatatgcca gtacgccccc ctattgacgt caatgacggt      5640
aaatggcccg cctggcatta tgcccagtac atgaccttat gggactttcc tacttggcag      5700
tacatctacg tattagtcat cgctattacc atggtgatgc ggttttggca gtacatcaat      5760
gggcgtggat agcggtttga ctcacgggga tttccaagtc tccaccccat tgacgtcaat      5820
gggagtttgt tttggcacca aaatcaacgg gactttccaa aatgtcgtaa caactccgcc      5880
ccattgacgc aaatgggcgg taggcgtgta cggtgggagg tctatataag cagagctctc      5940
cctatcagtg atagagatct ccctatcagt gatagagatc gtcgacgttt agtgaaccgt      6000
cagatcgcct ggagacgcca tccacgctgt tttgacctcc atagaagaca ccgggaccga      6060
tccagcctcc gcggccggga acggtgcatt ggaacgcgga ttccccgtgc caagagtgac      6120
gtaagtaccg cctatagagt ctataggccc accccccttgg cttcttatgc atgctatact      6180 gttttggct tggggtctat acaccccgc ttcctcatgt tataggtgat ggtatagctt      6240
agcctatagg tgtgggttat tgaccattat tgaccactcc cctattggtg acgatacttt      6300
ccattactaa tccataacat ggctctttgc cacaactctc tttattggct atatgccaat      6360
acactgtcct tcagagactg acacggactc tgtatttta caggatgggg tctcatttat      6420
tatttacaaa ttcacatata caacaccacc gtccccagtg cccgcagttt ttattaaaca      6480
taacgtggga tctccacgcg aatctcgggt acgtgttccg gacatgggct cttctccggt      6540
agcggcggag cttctacatc cgagccctgc tcccatgcct ccagcgactc atggtcgctc      6600
ggcagctcct tgctcctaac agtggaggcc agacttaggc acagcacgat gcccaccacc      6660
accagtgtgc cgcacaaggc cgtggcggta gggtatgtgt ctgaaaatga gctcggggag      6720
cgggcttgca ccgctgacgc atttggaaga cttaaggcag cggcagaaga agatgcaggc      6780
```

```
agctgagttg ttgtgttctg ataagagtca gaggtaactc ccgttgcggt gctgttaacg    6840
gtggagggca gtgtagtctg agcagtactc gttgctgccg cgcgcgccac cagacataat    6900
agctgacaga ctaacagact gttccttttcc atgggtcttt tctgcagtca ccgtccttga    6960
cacg                                                                 6964

<210> SEQ ID NO 2
<211> LENGTH: 1231
<212> TYPE: DNA
<213> ORGANISM: Cricetulus griseus

<400> SEQUENCE: 2
caccatgtgg gccttcccgg agttgccgct gccgctgctg gtgaatttgt tcggctcgct      60
gctgggattt gtggctactg tgaccctcat ccctgccttc cgtagccact ttatcgccgc     120
gcgcctctgt ggccaggacc tcaacaagct cagccggcag cagatcccag aatcccaggg     180
agtgatctgc ggtgctgttt tccttatcat cctcttctgc ttcatccctt ccccttcct     240 gaactgcttt gtggaggagc agtgtaaggc attcccccac catgaatttg tggccctgat     300
aggtgccctc cttgccatct gctgcatgat cttcctgggc ttcgctgatg atgtactcaa     360
tctgcgctgg cgccataagc tgctgctgcc cacagctgcc tctctacctc tcctcatggt     420
ttacttcact aactttggca atacaaccat tgtggtaccc aagcccttcc gctggattct     480
tggcctgcat ttggacttgg gaatcctata ctatgtctac atgggactgc ttgcggtgtt     540
ctgtaccaat gccatcaaca tcctagcagg aattaatggc ctagaggctg gtcagtcact     600
agtcatctct gcttctatca ttgtcttcaa cctggtagag ctggaaggtg attatcggga     660
tgatcatgtc ttttccctct acttcatgat accatttttt tttaccacct tgggattgct     720
ataccataac tggtacccat cacaggtgtt tgtgggagat accttctgtt attttgctgg     780
catgaccttt gccgtggtgg aatcttggg acacttcagc aagaccatgc tactcttctt     840
tattccacaa gtgttcaatt tcctctactc gctgcctcag ctccttcacg ccatcccctg     900
ccctcgacac cgcataccca gactcaatcc gaagacgggc aaactggaga tgagctattc     960
caagttcaag accaagaacc tctctttctt gggcaccttt attttaaagg tagcagagcg    1020
cctccagcta gtgacagttc accgaggcga gagtgaggat ggtgccttca ctgaatgtaa    1080
caacatgacc ctcatcaact tgctactcaa aatctttggg cccatacatg agagaaacct    1140
cacactgctc ctgctgcttt tgcagatcct gagcagcgct gtcaccttct ccattcgata    1200
ccagcttgtc cgactcttct atgatgtctg a                                  1231

<210> SEQ ID NO 3
<211> LENGTH: 408
<212> TYPE: PRT
<213> ORGANISM: Cricetulus griseus

<400> SEQUENCE: 3

Met Trp Ala Phe Pro Glu Leu Pro Leu Pro Leu Leu Val Asn Leu Phe
1               5                   10                  15

Gly Ser Leu Leu Gly Phe Val Ala Thr Val Thr Leu Ile Pro Ala Phe
            20                  25                  30

Arg Ser His Phe Ile Ala Ala Arg Leu Cys Gly Gln Asp Leu Asn Lys
        35                  40                  45

Leu Ser Arg Gln Gln Ile Pro Glu Ser Gln Gly Val Ile Cys Gly Ala
    50                  55                  60
```

```
Val Phe Leu Ile Ile Leu Phe Cys Phe Ile Pro Phe Leu Asn
 65                  70                  75                  80

Cys Phe Val Glu Glu Gln Cys Lys Ala Phe Pro His His Glu Phe Val
                 85                  90                  95

Ala Leu Ile Gly Ala Leu Leu Ala Ile Cys Cys Met Ile Phe Leu Gly
            100                 105                 110

Phe Ala Asp Asp Val Leu Asn Leu Arg Trp Arg His Lys Leu Leu
        115                 120                 125

Pro Thr Ala Ala Ser Leu Pro Leu Leu Met Val Tyr Phe Thr Asn Phe
        130                 135                 140

Gly Asn Thr Thr Ile Val Val Pro Lys Pro Phe Arg Trp Ile Leu Gly
145                 150                 155                 160

Leu His Leu Asp Leu Gly Ile Leu Tyr Tyr Val Tyr Met Gly Leu Leu
                165                 170                 175

Ala Val Phe Cys Thr Asn Ala Ile Asn Ile Leu Ala Gly Ile Asn Gly
                180                 185                 190

Leu Glu Ala Gly Gln Ser Leu Val Ile Ser Ala Ser Ile Ile Val Phe
            195                 200                 205

Asn Leu Val Glu Leu Glu Gly Asp Tyr Arg Asp Asp His Val Phe Ser
210                 215                 220

Leu Tyr Phe Met Ile Pro Phe Phe Thr Thr Leu Gly Leu Leu Tyr
225                 230                 235                 240

His Asn Trp Tyr Pro Ser Gln Val Phe Val Gly Asp Thr Phe Cys Tyr
                245                 250                 255

Phe Ala Gly Met Thr Phe Ala Val Val Gly Ile Leu Gly His Phe Ser
            260                 265                 270

Lys Thr Met Leu Leu Phe Phe Ile Pro Gln Val Phe Asn Phe Leu Tyr
        275                 280                 285

Ser Leu Pro Gln Leu Leu His Ala Ile Pro Cys Pro Arg His Arg Ile
        290                 295                 300

Pro Arg Leu Asn Pro Lys Thr Gly Lys Leu Glu Met Ser Tyr Ser Lys
305                 310                 315                 320

Phe Lys Thr Lys Asn Leu Ser Phe Leu Gly Thr Phe Ile Leu Lys Val
                325                 330                 335

Ala Glu Arg Leu Gln Leu Val Thr Val His Arg Gly Glu Ser Glu Asp
            340                 345                 350

Gly Ala Phe Thr Glu Cys Asn Asn Met Thr Leu Ile Asn Leu Leu Leu
        355                 360                 365

Lys Ile Phe Gly Pro Ile His Glu Arg Asn Leu Thr Leu Leu Leu
        370                 375                 380

Leu Leu Gln Ile Leu Ser Ser Ala Val Thr Phe Ser Ile Arg Tyr Gln
385                 390                 395                 400

Leu Val Arg Leu Phe Tyr Asp Val
                405

<210> SEQ ID NO 4
<211> LENGTH: 408
<212> TYPE: PRT
<213> ORGANISM: Homo sapiens

<400> SEQUENCE: 4

Met Trp Ala Phe Ser Glu Leu Pro Met Pro Leu Leu Ile Asn Leu Ile
1               5                   10                  15

Val Ser Leu Leu Gly Phe Val Ala Thr Val Thr Leu Ile Pro Ala Phe
            20                  25                  30
```

Arg Gly His Phe Ile Ala Ala Arg Leu Cys Gly Gln Asp Leu Asn Lys
                35                  40                  45

Thr Ser Arg Gln Gln Ile Pro Glu Ser Gln Gly Val Ile Ser Gly Ala
 50                  55                  60

Val Phe Leu Ile Ile Leu Phe Cys Phe Ile Pro Phe Pro Phe Leu Asn
 65                  70                  75                  80

Cys Phe Val Lys Glu Gln Cys Lys Ala Phe Pro His His Glu Phe Val
                85                  90                  95

Ala Leu Ile Gly Ala Leu Leu Ala Ile Cys Cys Met Ile Phe Leu Gly
                100                 105                 110

Phe Ala Asp Asp Val Leu Asn Leu Arg Trp Arg His Lys Leu Leu Leu
                115                 120                 125

Pro Thr Ala Ala Ser Leu Pro Leu Leu Met Val Tyr Phe Thr Asn Phe
130                 135                 140

Gly Asn Thr Thr Ile Val Val Pro Lys Pro Phe Arg Pro Ile Leu Gly
145                 150                 155                 160

Leu His Leu Asp Leu Gly Ile Leu Tyr Tyr Val Tyr Met Gly Leu Leu
                165                 170                 175

Ala Val Phe Cys Thr Asn Ala Ile Asn Ile Leu Ala Gly Ile Asn Gly
                180                 185                 190

Leu Glu Ala Gly Gln Ser Leu Val Ile Ser Ala Ser Ile Ile Val Phe
                195                 200                 205

Asn Leu Val Glu Leu Glu Gly Asp Cys Arg Asp Asp His Val Phe Ser
210                 215                 220

Leu Tyr Phe Met Ile Pro Phe Phe Phe Thr Thr Leu Gly Leu Leu Tyr
225                 230                 235                 240

His Asn Trp Tyr Pro Ser Arg Val Phe Val Gly Asp Thr Phe Cys Tyr
                245                 250                 255

Phe Ala Gly Met Thr Phe Ala Val Val Gly Ile Leu Gly His Phe Ser
                260                 265                 270

Lys Thr Met Leu Leu Phe Phe Met Pro Gln Val Phe Asn Phe Leu Tyr
                275                 280                 285

Ser Leu Pro Gln Leu Leu His Ile Ile Pro Cys Pro Arg His Arg Ile
290                 295                 300

Pro Arg Leu Asn Ile Lys Thr Gly Lys Leu Glu Met Ser Tyr Ser Lys
305                 310                 315                 320

Phe Lys Thr Lys Ser Leu Ser Phe Leu Gly Thr Phe Ile Leu Lys Val
                325                 330                 335

Ala Glu Ser Leu Gln Leu Val Thr Val His Gln Ser Glu Thr Glu Asp
                340                 345                 350

Gly Glu Phe Thr Glu Cys Asn Asn Met Thr Leu Ile Asn Leu Leu Leu
                355                 360                 365

Lys Val Leu Gly Pro Ile His Glu Arg Asn Leu Thr Leu Leu Leu Leu
370                 375                 380

Leu Leu Gln Ile Leu Gly Ser Ala Ile Thr Phe Ser Ile Arg Tyr Gln
385                 390                 395                 400

Leu Val Arg Leu Phe Tyr Asp Val
                405

<210> SEQ ID NO 5
<211> LENGTH: 408
<212> TYPE: PRT
<213> ORGANISM: Macaca mulatta

<400> SEQUENCE: 5

```
Met Trp Ala Phe Ser Glu Leu Pro Met Pro Leu Leu Val Asn Leu Ile
1               5                  10                 15

Val Ser Leu Leu Gly Phe Val Ala Thr Val Thr Leu Ile Pro Ala Phe
            20                  25                  30

Arg Gly His Phe Ile Ala Ala Arg Leu Cys Gly Gln Asp Leu Asn Lys
        35                  40                  45

Thr Ser Arg Gln Gln Ile Pro Glu Ser Gln Gly Val Ile Ser Gly Ala
    50                  55                  60

Val Phe Leu Ile Ile Leu Phe Cys Phe Ile Pro Phe Pro Phe Leu Asn
65                  70                  75                  80

Cys Phe Val Lys Glu Gln Cys Lys Ala Phe Pro His His Glu Phe Val
                85                  90                  95

Ala Leu Ile Gly Ala Leu Leu Ala Ile Cys Cys Met Ile Phe Leu Gly
            100                 105                 110

Phe Ala Asp Asp Val Leu Asn Leu Arg Trp Arg His Lys Leu Leu Leu
        115                 120                 125

Pro Thr Ala Ala Ser Leu Pro Leu Leu Met Val Tyr Phe Thr Asn Phe
    130                 135                 140

Gly Asn Thr Thr Ile Val Val Pro Lys Pro Phe Arg Pro Ile Leu Gly
145                 150                 155                 160

Leu His Leu Asp Leu Gly Ile Leu Tyr Tyr Val Tyr Met Gly Leu Leu
                165                 170                 175

Ala Val Phe Cys Thr Asn Ala Ile Asn Ile Leu Ala Gly Ile Asn Gly
            180                 185                 190

Leu Glu Ala Gly Gln Ser Leu Val Ile Ser Ala Ser Ile Ile Val Phe
        195                 200                 205

Asn Leu Val Glu Leu Glu Gly Asp Cys Arg Asp His Val Phe Ser
    210                 215                 220

Leu Tyr Phe Met Ile Pro Phe Phe Thr Thr Leu Gly Leu Leu Tyr
225                 230                 235                 240

His Asn Trp Tyr Pro Ser Arg Val Phe Val Gly Asp Thr Phe Cys Tyr
                245                 250                 255

Phe Ala Gly Met Thr Phe Ala Val Val Gly Ile Leu Gly His Phe Ser
            260                 265                 270

Lys Thr Met Leu Leu Phe Phe Met Pro Gln Val Phe Asn Phe Leu Tyr
        275                 280                 285

Ser Leu Pro Gln Leu Leu His Ile Ile Pro Cys Pro Arg His Arg Ile
    290                 295                 300

Pro Arg Leu Asn Ile Lys Thr Gly Lys Leu Glu Met Ser Tyr Ser Lys
305                 310                 315                 320

Phe Lys Thr Lys Ser Leu Ser Phe Leu Gly Thr Phe Ile Leu Lys Val
                325                 330                 335

Ala Glu Ser Leu Arg Leu Val Thr Ile His Gln Ser Asp Thr Glu Asp
            340                 345                 350

Gly Glu Phe Thr Glu Cys Asn Asn Met Thr Leu Ile Asn Leu Leu Leu
        355                 360                 365

Lys Ile Phe Gly Pro Ile His Glu Arg Asn Leu Thr Leu Leu Leu Leu
    370                 375                 380

Leu Leu Gln Ile Leu Gly Ser Ala Phe Thr Phe Ser Ile Arg Tyr Gln
385                 390                 395                 400

Leu Val Arg Leu Phe Tyr Asp Val
                405
```

<210> SEQ ID NO 6
<211> LENGTH: 408
<212> TYPE: PRT
<213> ORGANISM: Pan troglodytes

<400> SEQUENCE: 6

```
Met Trp Ala Phe Ser Glu Leu Pro Met Pro Leu Leu Ile Asn Leu Ile
1               5                   10                  15

Val Ser Leu Leu Gly Phe Val Ala Thr Val Thr Leu Ile Pro Ala Phe
            20                  25                  30

Arg Gly His Phe Ile Ala Ala Arg Leu Cys Gly Gln Asp Leu Asn Lys
        35                  40                  45

Thr Ser Arg Gln Gln Ile Pro Glu Ser Gln Gly Val Ile Ser Gly Ala
    50                  55                  60

Val Phe Leu Ile Ile Leu Phe Cys Phe Ile Pro Phe Pro Phe Leu Asn
65                  70                  75                  80

Cys Phe Val Lys Glu Gln Cys Lys Ala Phe Pro His His Glu Phe Val
                85                  90                  95

Ala Leu Ile Gly Ala Leu Leu Ala Ile Cys Cys Met Ile Phe Leu Gly
            100                 105                 110

Phe Ala Asp Asp Val Leu Asn Leu Arg Trp Arg His Lys Leu Leu Leu
        115                 120                 125

Pro Thr Ala Ala Ser Leu Pro Leu Leu Met Val Tyr Phe Thr Asn Phe
    130                 135                 140

Gly Asn Thr Thr Ile Val Val Pro Lys Pro Phe Arg Pro Ile Leu Gly
145                 150                 155                 160

Leu His Leu Asp Leu Gly Ile Leu Tyr Tyr Val Tyr Met Gly Leu Leu
                165                 170                 175

Ala Val Phe Cys Thr Asn Ala Ile Asn Ile Leu Ala Gly Ile Asn Gly
            180                 185                 190

Leu Glu Ala Gly Gln Ser Leu Val Ile Ser Ala Ser Ile Ile Val Phe
        195                 200                 205

Asn Leu Val Glu Leu Glu Gly Asp Cys Arg Asp Asp His Val Phe Ser
    210                 215                 220

Leu Tyr Phe Met Ile Pro Phe Phe Thr Thr Leu Gly Leu Leu Tyr
225                 230                 235                 240

His Asn Trp Tyr Pro Ser Arg Val Phe Val Gly Asp Thr Phe Cys Tyr
                245                 250                 255

Phe Ala Gly Met Thr Phe Ala Val Val Gly Ile Leu Gly His Phe Ser
            260                 265                 270

Lys Thr Met Leu Leu Phe Phe Met Pro Gln Val Phe Asn Phe Leu Tyr
        275                 280                 285

Ser Leu Pro Gln Leu Leu His Ile Ile Pro Cys Pro Arg His Arg Ile
    290                 295                 300

Pro Arg Leu Asn Ile Lys Thr Gly Lys Leu Glu Met Ser Tyr Ser Lys
305                 310                 315                 320

Phe Lys Thr Lys Ser Leu Ser Phe Leu Gly Thr Phe Ile Leu Lys Val
                325                 330                 335

Ala Glu Ser Leu Gln Leu Val Thr Val His Gln Ser Glu Thr Glu Asp
            340                 345                 350

Gly Glu Phe Thr Glu Cys Asn Asn Met Thr Leu Ile Asn Leu Leu Leu
        355                 360                 365

Lys Ile Leu Gly Pro Ile His Glu Arg Asn Leu Thr Leu Leu Leu Leu
```

370                 375                 380
Leu Leu Gln Ile Leu Gly Ser Ala Ile Thr Phe Ser Ile Arg Tyr Gln
385                 390                 395                 400

Leu Val Arg Leu Phe Tyr Asp Val
                405

<210> SEQ ID NO 7
<211> LENGTH: 408
<212> TYPE: PRT
<213> ORGANISM: Canis familiaris

<400> SEQUENCE: 7

Met Trp Ala Phe Pro Glu Leu Pro Met Pro Leu Leu Val Asn Leu Val
1               5                   10                  15

Gly Ser Leu Leu Gly Phe Val Ala Thr Val Thr Leu Ile Pro Ala Phe
                20                  25                  30

Arg Gly His Phe Ile Ala Ala His Leu Cys Gly Gln Asp Leu Asn Lys
            35                  40                  45

Thr Gly Arg Gln Gln Ile Pro Glu Ser Gln Gly Val Ile Ser Gly Ala
50                  55                  60

Val Phe Leu Ile Ile Leu Phe Cys Phe Ile Pro Phe Pro Phe Leu Asn
65                  70                  75                  80

Cys Phe Met Glu Glu Gln Cys Lys Ala Phe Pro His His Glu Phe Val
                85                  90                  95

Ala Leu Ile Gly Ala Leu Leu Ala Ile Cys Cys Met Ile Phe Leu Gly
            100                 105                 110

Phe Ala Asp Asp Val Leu Asn Leu Arg Trp Arg His Lys Leu Leu Leu
        115                 120                 125

Pro Thr Ala Ala Ser Leu Pro Leu Leu Met Val Tyr Phe Thr Asn Phe
130                 135                 140

Gly Asn Thr Thr Ile Val Val Pro Lys Pro Phe Arg Pro Ile Leu Gly
145                 150                 155                 160

Leu His Leu Asp Leu Gly Ile Leu Tyr Tyr Val Tyr Met Gly Leu Leu
                165                 170                 175

Ala Val Phe Cys Thr Asn Ala Ile Asn Ile Leu Ala Gly Ile Asn Gly
            180                 185                 190

Leu Glu Ala Gly Gln Ser Leu Val Ile Ser Ala Ser Ile Ile Val Phe
        195                 200                 205

Asn Leu Val Glu Leu Glu Gly Asp Tyr Arg Asp Asp His Val Phe Ser
210                 215                 220

Leu Tyr Phe Met Ile Pro Phe Phe Phe Thr Thr Leu Gly Leu Leu Tyr
225                 230                 235                 240

His Asn Trp Tyr Pro Ser Gln Val Phe Val Gly Asp Thr Phe Cys Tyr
                245                 250                 255

Phe Ala Gly Met Thr Phe Ala Val Val Gly Ile Leu Gly His Phe Ser
            260                 265                 270

Lys Thr Met Leu Leu Phe Phe Met Pro Gln Val Phe Asn Phe Leu Tyr
        275                 280                 285

Ser Leu Pro Gln Leu Leu His Ile Ile Pro Cys Pro Arg His Arg Ile
290                 295                 300

Pro Arg Leu Asn Thr Lys Thr Gly Lys Leu Glu Met Ser Tyr Ser Lys
305                 310                 315                 320

Phe Lys Thr Lys Ser Leu Ser Phe Leu Gly Asn Phe Ile Leu Lys Val
                325                 330                 335

```
Ala Ala Ser Leu Gln Leu Val Thr Val His Gln Ser Glu Asn Glu Asp
            340                 345                 350

Gly Ala Phe Thr Glu Cys Asn Asn Met Thr Leu Leu Asn Leu Leu Leu
            355                 360                 365

Lys Val Leu Gly Pro Met His Glu Arg Asn Leu Thr Leu Leu Leu Leu
        370                 375                 380

Leu Leu Gln Ile Leu Gly Ser Ala Val Thr Phe Ser Ile Arg Tyr Gln
385                 390                 395                 400

Leu Val Arg Leu Phe Tyr Asp Val
                405

<210> SEQ ID NO 8
<211> LENGTH: 408
<212> TYPE: PRT
<213> ORGANISM: Cavia porcellus

<400> SEQUENCE: 8

Met Trp Ala Phe Ser Glu Val Pro Ile Pro Leu Leu Val Asn Leu Ile
1               5                   10                  15

Gly Ser Leu Leu Gly Phe Val Ala Thr Leu Thr Leu Ile Pro Ala Phe
            20                  25                  30

Arg Gly His Phe Ile Ala Ala Arg Leu Cys Gly Gln Asp Leu Asn Lys
        35                  40                  45

Thr Asn Arg Gln Gln Ile Pro Glu Ser Gln Gly Val Ile Ser Gly Ala
    50                  55                  60

Val Phe Leu Ile Ile Leu Phe Cys Phe Ile Pro Phe Pro Phe Leu Asn
65                  70                  75                  80

Cys Phe Val Lys Glu Gln Cys Lys Ala Phe Pro His His Glu Phe Val
                85                  90                  95

Ala Leu Ile Gly Ala Leu Leu Ala Ile Cys Cys Met Ile Phe Leu Gly
            100                 105                 110

Phe Ala Asp Asp Val Leu Asn Leu Arg Trp Arg His Lys Leu Leu Leu
            115                 120                 125

Pro Thr Ala Ala Ser Leu Pro Leu Leu Met Val Tyr Phe Thr Asn Phe
    130                 135                 140

Gly Asn Thr Thr Ile Val Val Pro Lys Pro Phe Arg Pro Val Leu Gly
145                 150                 155                 160

Leu His Leu Asp Leu Gly Ile Leu Tyr Tyr Val Tyr Met Gly Leu Leu
                165                 170                 175

Ala Val Phe Cys Thr Asn Ala Ile Asn Ile Leu Ala Gly Ile Asn Gly
            180                 185                 190

Leu Glu Ala Gly Gln Ser Leu Val Ile Ser Ala Ser Ile Ile Val Phe
        195                 200                 205

Asn Leu Val Glu Leu Gln Gly Asp Tyr Arg Asp His Val Phe Ser
    210                 215                 220

Leu Tyr Phe Met Ile Pro Phe Phe Thr Thr Leu Gly Leu Leu Tyr
225                 230                 235                 240

His Asn Trp Tyr Pro Ser Gln Val Phe Val Gly Asp Thr Phe Cys Tyr
                245                 250                 255

Phe Ala Gly Met Thr Phe Ala Val Val Gly Ile Leu Gly His Phe Ser
            260                 265                 270

Lys Thr Met Leu Leu Phe Phe Met Pro Gln Val Phe Asn Phe Leu Tyr
        275                 280                 285

Ser Leu Pro Gln Leu Leu His Ile Ile Pro Cys Pro Arg His Arg Ile
    290                 295                 300
```

Pro Arg Leu Asn Thr Lys Thr Gly Lys Leu Glu Met Ser Tyr Ser Lys
305                 310                 315                 320

Phe Lys Thr Asn Ser Leu Ser Phe Leu Gly Thr Phe Ile Leu Lys Val
                325                 330                 335

Ala Glu Arg Leu Gln Leu Val Thr Val His Arg Ser Glu Gly Glu Asp
            340                 345                 350

Gly Ala Phe Thr Glu Cys Asn Asn Met Thr Leu Ile Asn Leu Leu Leu
        355                 360                 365

Lys Ile Phe Gly Pro Ile His Glu Arg Asn Leu Thr Leu Leu Leu Leu
    370                 375                 380

Leu Leu Gln Ile Val Gly Ser Ala Val Thr Phe Ser Ile Arg Tyr Gln
385                 390                 395                 400

Leu Val Arg Leu Phe Tyr Asp Val
                405

<210> SEQ ID NO 9
<211> LENGTH: 410
<212> TYPE: PRT
<213> ORGANISM: Rattus norvegicus

<400> SEQUENCE: 9

Met Trp Ala Phe Pro Glu Leu Pro Leu Pro Leu Leu Val Asn
1               5                   10                  15

Leu Ile Gly Ser Leu Leu Gly Phe Val Ala Thr Val Thr Leu Ile Pro
                20                  25                  30

Ala Phe Arg Ser His Phe Ile Ala Ala Arg Leu Cys Gly Gln Asp Leu
            35                  40                  45

Asn Lys Leu Ser Arg Gln Gln Ile Pro Glu Ser Gln Gly Val Ile Ser
    50                  55                  60

Gly Ala Val Phe Leu Ile Ile Leu Phe Cys Phe Ile Pro Phe Pro Phe
65                  70                  75                  80

Leu Asn Cys Phe Val Glu Glu Gln Cys Lys Ala Phe Pro His His Glu
                85                  90                  95

Phe Val Ala Leu Ile Gly Ala Leu Leu Ala Ile Cys Cys Met Ile Phe
            100                 105                 110

Leu Gly Phe Ala Asp Asp Val Leu Asn Leu Arg Trp Arg His Lys Leu
        115                 120                 125

Leu Leu Pro Thr Ala Ala Ser Leu Pro Leu Leu Met Val Tyr Phe Thr
    130                 135                 140

Asn Phe Gly Asn Thr Thr Ile Val Val Pro Lys Pro Phe Arg Trp Ile
145                 150                 155                 160

Leu Gly Leu His Leu Asp Leu Gly Ile Leu Tyr Tyr Val Tyr Met Gly
                165                 170                 175

Leu Leu Ala Val Phe Cys Thr Asn Ala Ile Asn Ile Leu Ala Gly Ile
            180                 185                 190

Asn Gly Leu Glu Ala Gly Gln Ser Leu Val Ile Ser Ala Ser Ile Ile
        195                 200                 205

Val Phe Asn Leu Val Glu Leu Glu Gly Asp Tyr Arg Asp Asp His Val
    210                 215                 220

Phe Ser Leu Tyr Phe Met Met Pro Phe Phe Thr Thr Leu Gly Leu
225                 230                 235                 240

Leu Tyr His Asn Trp Tyr Pro Ser Gln Val Phe Val Gly Asp Thr Phe
                245                 250                 255

Cys Tyr Phe Ala Gly Met Thr Phe Ala Val Val Gly Ile Leu Gly His

```
                    260                 265                 270
Phe Ser Lys Thr Met Leu Leu Phe Phe Met Pro Gln Val Phe Asn Phe
            275                 280                 285

Leu Tyr Ser Leu Pro Gln Leu Phe Gln Ile Ile Pro Cys Pro Arg His
        290                 295                 300

Arg Met Pro Arg Leu Asn Thr Lys Thr Gly Lys Leu Glu Met Ser Tyr
305                 310                 315                 320

Ser Lys Phe Lys Thr Lys Ser Leu Ser Phe Leu Gly Thr Phe Ile Leu
                325                 330                 335

Lys Val Ala Glu Ser Leu Arg Leu Val Thr Val His Arg Gly Glu Ser
            340                 345                 350

Glu Asp Gly Ala Phe Thr Glu Cys Asn Asn Met Thr Leu Ile Asn Leu
        355                 360                 365

Leu Leu Lys Val Phe Gly Pro Thr His Glu Arg Asn Leu Thr Leu Phe
    370                 375                 380

Leu Leu Leu Leu Gln Val Leu Ser Ser Ala Val Thr Phe Ser Ile Arg
385                 390                 395                 400

Tyr Gln Leu Val Arg Leu Phe Tyr Asp Val
                405                 410

<210> SEQ ID NO 10
<211> LENGTH: 410
<212> TYPE: PRT
<213> ORGANISM: Mus musculus

<400> SEQUENCE: 10

Met Trp Ala Phe Pro Glu Leu Pro Leu Pro Leu Leu Val Asn
1               5                   10                  15

Leu Ile Gly Ser Leu Leu Gly Phe Val Ala Thr Val Thr Leu Ile Pro
            20                  25                  30

Ala Phe Arg Ser His Phe Ile Ala Ala Arg Leu Cys Gly Gln Asp Leu
        35                  40                  45

Asn Lys Leu Ser Gln Gln Gln Ile Pro Glu Ser Gln Gly Val Ile Ser
    50                  55                  60

Gly Ala Val Phe Leu Ile Ile Leu Phe Cys Phe Ile Pro Phe Pro Phe
65                  70                  75                  80

Leu Asn Cys Phe Val Glu Glu Gln Cys Lys Ala Phe Pro His His Glu
                85                  90                  95

Phe Val Ala Leu Ile Gly Ala Leu Leu Ala Ile Cys Cys Met Ile Phe
            100                 105                 110

Leu Gly Phe Ala Asp Asp Val Leu Asn Leu Arg Trp Arg His Lys Leu
        115                 120                 125

Leu Leu Pro Thr Ala Ala Ser Leu Pro Leu Leu Met Val Tyr Phe Thr
    130                 135                 140

Asn Phe Gly Asn Thr Thr Ile Val Val Pro Lys Pro Phe Arg Trp Ile
145                 150                 155                 160

Leu Gly Leu His Leu Asp Leu Gly Ile Leu Tyr Tyr Val Tyr Met Gly
                165                 170                 175

Leu Leu Ala Val Phe Cys Thr Asn Ala Ile Asn Ile Leu Ala Gly Ile
            180                 185                 190

Asn Gly Leu Glu Ala Gly Gln Ser Leu Val Ile Ser Ala Ser Ile Ile
        195                 200                 205

Val Phe Asn Leu Val Glu Leu Glu Gly Asp Tyr Arg Asp Asp His Ile
    210                 215                 220
```

```
Phe Ser Leu Tyr Phe Met Ile Pro Phe Phe Thr Thr Leu Gly Leu
225                 230                 235                 240

Leu Tyr His Asn Trp Tyr Pro Ser Arg Val Phe Val Gly Asp Thr Phe
            245                 250                 255

Cys Tyr Phe Ala Gly Met Thr Phe Ala Val Val Gly Ile Leu Gly His
                260                 265                 270

Phe Ser Lys Thr Met Leu Leu Phe Phe Met Pro Gln Val Phe Asn Phe
            275                 280                 285

Leu Tyr Ser Leu Pro Gln Leu Phe His Ile Ile Pro Cys Pro Arg His
            290                 295                 300

Arg Met Pro Arg Leu Asn Ala Lys Thr Gly Lys Leu Glu Met Ser Tyr
305                 310                 315                 320

Ser Lys Phe Lys Thr Lys Asn Leu Ser Phe Leu Gly Thr Phe Ile Leu
                325                 330                 335

Lys Val Ala Glu Asn Leu Arg Leu Val Thr Val His Gln Gly Glu Ser
                340                 345                 350

Glu Asp Gly Ala Phe Thr Glu Cys Asn Asn Met Thr Leu Ile Asn Leu
            355                 360                 365

Leu Leu Lys Val Phe Gly Pro Ile His Glu Arg Asn Leu Thr Leu Leu
370                 375                 380

Leu Leu Leu Leu Gln Val Leu Ser Ser Ala Ala Thr Phe Ser Ile Arg
385                 390                 395                 400

Tyr Gln Leu Val Arg Leu Phe Tyr Asp Val
                405                 410

<210> SEQ ID NO 11
<211> LENGTH: 1920
<212> TYPE: DNA
<213> ORGANISM: Mus musculus

<400> SEQUENCE: 11
gttgcttcct aagagcttct tgctggtcag gagggagggt caggtcctag cgtcctagct      60
gggttttgtt cccgctggcg ccggaatcct ctgcgggttg ggagccgcac tgccggctgc     120
cgaggccacg ggattgttcc tggcttacca gttagctgag taggcggcgg ggcggcggcc     180
accggagggt caccatgtgg gccttccgg agttgcccct gccgctgccg ctgctggtga     240
atttgatcgg ctcgctgttg ggattcgtgg ctacagtcac cctcatccct gccttccgta     300
gccactttat cgccgcgcgc ctctgtggcc aggacctcaa caagctcagc cagcagcaga     360
tcccagagtc ccagggagtg atcagcggtg ctgttttcct tatcatcctc ttctgcttca     420
tcccttttcc cttcctgaac tgcttcgtgg aggagcagtg taaggcattc ccccaccatg     480
aatttgtggc cctaataggt gccctccttg ccatctgctg catgatcttc ctggggtttg     540
ctgatgatgt cctcaatctc cgctggcgcc acaagctgct gctgcccaca gctgcctcac     600
tacctctcct catggtctac ttcacaaaact ttggcaatac aaccatcgtg gtgcccaagc     660
ccttccgctg gattctgggc ctgcatttgg acttggggat cctgtactac gtctacatgg     720
gctgcttgc agtgttctgt accaatgcca tcaacatcct ggcgggcatt aatggcctag     780
aggccggtca gtcactagtc atctctgctt ctatcattgt cttcaacctg gtggaactgg     840
aaggtgatta tcgagatgat catatctttt cccttttactt catgatacca ttttttctta     900
ccacccttgg gactgcttac acacaactggt acccgtcccg cgtgtttgtg ggagacacct     960
tctgttactt tgcgggcatg acttttgccg tggtggggat cttgggacac ttcagcaaga    1020
ccatgctgct cttctttatg ccacaagtat tcaatttcct ctactcactg cctcagctct    1080
```

-continued

```
tccatatcat cccctgccct cgacaccgga tgcccagact caacgcaaag acaggcaaac    1140
tggaaatgag ctattccaag ttcaagacca agaacctctc tttcctgggc acctttattt    1200
taaaggtagc agagaacctc cggttagtga cagttcacca aggtgagagt gaggacggtg    1260
ccttcactga gtgtaacaac atgaccctca tcaacttgct acttaaagtc tttgggccta    1320
tacatgagag aaacctcacc ctgctcctgc tgctcctgca ggtcctaagc agcgccgcca    1380
ccttctccat tcgttaccaa ctcgtccgac tcttctatga tgtctgagct ccctgacagc    1440
tgccctttac ctcacagtct ccattggacc tcagccagga ccagcctctg tctggtccga    1500
gatgaccctc tggtccaggc ctcgctgaca cttttgttct cagcttctgc catctgtgac    1560
tactgatatc ctggatggac accttgctgg acttgaagtc cgctagttgg actttgccta    1620
gggctttcat cttgccttgc cctcccttc tgtcccatct gcagcctcac caggtgggct    1680
tgtagcctct attatgcaaa tattcgtagc tcagctttca gagcgctaac tctaaaggaa    1740
ttcacctgag ccttgagaga gaacctgggc tagggctaga gttagggcta catactccaa    1800
ggtgacctca catttgacta tcaaatgaag tgttgtgatt gggaagcgta gaggcagggc    1860
catgtgctca gaacggtgac aataaaggac tgccttttac ttgttaaaaa aaaaaaaaaa    1920
```

<210> SEQ ID NO 12
<211> LENGTH: 2150
<212> TYPE: DNA
<213> ORGANISM: Homo sapiens

<400> SEQUENCE: 12

```
aagtatccgt tcttggctgc cttctttaa ttgcgtttcc agtactctct cggtgattct      60
actcttgaac ataggatgaa atttggaatc acacttctct tccacttcca tccccaccct    120
ctaatgccca tattaaaaat ggcggccgcc gccttccgca gtaatggttg ttcagcgaac    180
aagatccggg cggaaacagt agataggcgg gtgcagcggg gcagaacata ggttgcctta    240
gagaggttcc ccggtgtccc gacggcggct caagtcagag ttgctgggtt ttgctcagat    300
tggtgtggga agagcctgcc tgtggggagc ggccactcca tactgctgag gcctcaggac    360
tgctgctcag cttgcccgtt acctgaagag gcggcggagc cgggcccctg accggtcacc    420
atgtgggcct tctcggaatt gcccatgccg ctgctgatca atttgatcgt ctcgctgctg    480
ggatttgtgg ccacagtcac cctcatcccg gccttccggg ccacttcat tgctgcgcgc    540 ctctgtggtc aggacctcaa caaaaccagc cgacagcaga tcccagaatc ccagggagtg    600
atcagcggtg ctgttttcct tatcatcctc ttctgcttca tccctttccc cttcctgaac    660
tgctttgtga aggagcagtg taaggcattc ccccaccatg aatttgtggc cctgataggt    720
gccctccttg ccatctgctg catgatcttc tgggctttg cggatgatgt actgaatctg    780
cgctggcgcc ataagctgct gctacctaca gctgcctcac tacctctcct catggtctat    840
ttcaccaact ttggcaacac gaccattgtg gtgcccaagc ccttccgccc gatacttggc    900
ctgcatctgg acttgggaat cctgtactat gtctacatgg ggctgctggc agtgttctgt    960
accaatgcca tcaatatcct agcaggaatt aacggcctag aggctggcca gtcactagtc    1020
atttctgctt ccatcattgt cttcaacctg gtagagttgg aaggtgattg tcgggatgat    1080
catgtctttt ccctctactt catgataccc ttttttttca ccactttggg attgctctac    1140
cacaactggt acccatcacg ggtgtttgtg ggagataccc tctgttactt tgctggcatg    1200
acctttgccg tggtgggcat cttgggacac ttcagcaaga ccatgctact attcttcatg    1260
```

| | |
|---|---|
| ccccaggtgt tcaacttcct ctactcactg cctcagctcc tgcatatcat ccctgccct | 1320 |
| cgccaccgca tacccagact caatatcaag acaggcaaac tggagatgag ctattccaag | 1380 |
| ttcaagacca agagcctctc tttcttgggc acctttattt taaaggtggc agagagcctc | 1440 |
| cagctggtga cagtacacca gagtgagact gaagatggtg aattcactga atgtaacaac | 1500 |
| atgaccctca tcaacttgct acttaaagtc cttgggccca tacatgagag aaacctcaca | 1560 |
| ttgctcctgc tgctgctgca gatcctgggc agtgccatca ccttctccat tcgatatcag | 1620 |
| ctcgttcgac tcttctatga tgtctgagtc ccttgatcat tgtcctttac ctcacagtct | 1680 |
| ctaggattcc tgactcaggc tgacctctct ctctggtccc agactgcctc cttgcccagg | 1740 |
| cctctctcac tcttcatact cctccagatt ttgttctcag catttccctt tctctgtgat | 1800 |
| cattggcatc ctgggcgttt cttgccctct gctgactact gattggattt tacctatggc | 1860 |
| tttctgcaac ttgctactct ctccctctcc atcccatctt tgcagcctca tagggtggga | 1920 |
| tacagcagct tttttgcag ttatccacac tcacatttca gagtcctgac tctcaaggaa | 1980 |
| ccactggttt ttgggataga acttgggcca gggctaggaa cacaggctcc acggtgacat | 2040 |
| gtcatttgat tgtaaattaa gtgttctgat tagtaagaac taagcagggg gccacatgct | 2100 |
| ctcaatggag acaataaagt gttgtctttt tcttattgtt taaaaaaaaa | 2150 |

<210> SEQ ID NO 13
<211> LENGTH: 1840
<212> TYPE: DNA
<213> ORGANISM: Rattus norvegicus

<400> SEQUENCE: 13

| | |
|---|---|
| gggggctggc gccggaatcc tctgagtgta gggagctgca ctgctggctg ccgaggcctc | 60 |
| tggtttgttc ctggcttacc aagttagctg agtaggcggc ggagcggcgg ccccggagg | 120 |
| gtcactatgt gggccttccc ggagttacct ctgccgctgc cgctgttggt gaatttgatc | 180 |
| ggatcgctgt tgggatttgt ggctaccgtc accctcatcc ctgccttccg tagccacttt | 240 |
| atcgccgcgc gtctctgtgg ccaggacctc aacaagctca gccggcagca gatcccagag | 300 |
| tcccagggag tgatcagcgg tgctgttttc cttatcatcc tcttctgctt catccctttc | 360 |
| cctttcctga actgctttgt ggaggagcag tgtaaggcat ccccccacca tgaatttgtg | 420 |
| gccctgatag gtgccctcct tgctatctgc tgcatgatct tcctgggttt tgctgatgac | 480 |
| gtactcaatc tgcgatggcg tcataagctg ctgctcccca cagctgcctc actacctctc | 540 |
| ctcatggtct acttcactaa cttttggcaat acaaccattg tggtgccgaa gcccttccgc | 600 |
| tggattcttg gcctgcattt ggatttgggc atcctgtact atgtctacat gggactgctt | 660 |
| gcagtgttct gtaccaatgc catcaacatc ctagcgggaa ttaatggcct agaggctggt | 720 |
| caatcactag tcatctctgc ttctattatt gtcttcaacc tggtggagct ggaaggtgat | 780 |
| tatcgggacg atcatgtctt ttccctctac ttcatgatgc catttttttt taccaccttg | 840 |
| ggattgctgt accataactg gtacccgtct caggtgtttg tgggagacac cttctgttat | 900 |
| tttgctggca tgacctttgc cgtggtggga atcttgggac acttcagcaa gaccatgctg | 960 |
| ctcttcttta tgccacaagt attcaatttc tctctactcac tgcctcagct ctttcagatc | 1020 |
| atcccctgcc ctcgacaccg tatgcccaga ctcaatacga agacaggcaa actggagatg | 1080 |
| agctattcca agttcaagac caagagcctc tctttcttgg gcacgtttat tttaaaggta | 1140 |
| gcagagagc tccggctggt gacagttcac cgaggggaga gtgaggatgg tgccttcact | 1200 |
| gagtgtaaca acatgaccct catcaacttg ctacttaaag tctttgggcc tacacatgag | 1260 |

| | | |
|---|---|---|
| agaaacctca cactgttcct gctgctcctg caggttctga gcagcgctgt caccttctcc | 1320 | |
| attcgttacc agctcgtccg actcttctat gatgtctgag ctccctgacg actgcccttt | 1380 | |
| accacacagt ctccattgga cctcagccag acccacctc tgtccgctcc gaccgccttc | 1440 | |
| tggtccaggc tcagcttctg ccgtcatctg tgactactga catcctggat ggactcctta | 1500 | |
| gtggacttga cgtccactag ttggacttgc ctatgctttc ttgagtttgc tactccctcc | 1560 | |
| cttctgcag cctcaccagg tgggcctgta gcatctttta tgcaaatatt catggctcaa | 1620 | |
| ctttcagaac cctaactcta aaggaatccc ctgggccttg agagagaacc tgggctaggg | 1680 | |
| ctagagttag gcaacatac tccaaggtaa cctcacatct gactatcaaa ttaagtgttc | 1740 | |
| tgattaggaa gagcagaggc agggccatgt gctcagaatg gtgacaataa aggattgcct | 1800 | |
| tttacttgcc aaaaaaaaaa aaaaaaaaaa aaaaaaaaa | 1840 | |

<210> SEQ ID NO 14
<211> LENGTH: 5424
<212> TYPE: DNA
<213> ORGANISM: Macaca mulatta

<400> SEQUENCE: 14

| | | |
|---|---|---|
| tattaaaaat ggcggctgcc gccctccgca gtaatagttg ttcagcgaat aaaatccggg | 60 | |
| cggaaacagt aggtaggctg gttcagtggg ggcagaacct aggttgcctt agagaggttc | 120 | |
| ttcgaggtcc cgagggcggc tcaagtcaga gttgttggat tctgctcaga ttggtgtggg | 180 | |
| aagagcctgc ctgtggggag cggccactcc atactgctga ggcctcagga ctgctgctca | 240 | |
| gcttgccagt tacctgaaga ggcggcggag ccgggcccct gaccggtcac catgtgggcc | 300 | |
| ttctcggaat tgcccatgcc gctgctggtc aatttgatcg tctcgctgct gggatttgtg | 360 | |
| gccacagtca ccctcatccc agccttccgg ggccacttca ttgctgcgcg cctctgtggt | 420 | |
| caggacctca acaaaaccag ccgacaacag atgtgagcag cggcacacgg ttccgggcag | 480 | |
| ggggcaaggg ctaaggaagg agtggctagg gcaggggcgg ggaccggggt gtttgaccac | 540 | |
| acgtgaaaac tcagaactaa cccaggcagc ctggaactcg gagaggtgat gagcagaact | 600 | |
| tattcgcatt ggggaaagga tgggtaggga accttgggta tatcagggac tctagcagtg | 660 | |
| gtgctttcct ccctccgccc ccctccaccac ttcccaaaat aaaaaaccag gaatgagaag | 720 | |
| accgctttgg gttattgtaa cacctgcact agtgagtgac cacaccccct ttcctctttc | 780 | |
| ccctcgcccc cttgctgctg ggccacagcc cagaatccca gggagtgatc agcggtgctg | 840 | |
| ttttccttat catcctcttc tgcttcatcc ctttccccctt cctgaactgc tttgtgaagg | 900 | |
| agcagtgtaa ggcattcccc caccatgaag taagtgggtt cgtgggggtt gttgcctgtg | 960 | |
| gctgggacct gggaggtacc tgagagaatt ggtgttattt gggcttgtgg ggaggggcta | 1020 | |
| agaaatgata agaaaagaca agaattctta aaaggtgaaa tgggagcagg cttgagtcat | 1080 | |
| ggacctgccc tagcctcccc cagtttgtgg ccctgatagg tgccctcctt gccatctgct | 1140 | |
| gcatgatctt cctgggcttt gcggatgatg tactgaatct gcgctggcgc cataagctgc | 1200 | |
| tgctacccac agctgcctca ctacctctcc tcatggtcta tttcaccaac tttggcaaca | 1260 | |
| cgaccattgt ggtgccgaag cccttccgcc cgattcttgg cctgcatctg gacttgggta | 1320 | |
| ggtagtcctg ccactgctac tcctatggca cctacttcag ggcacccttc ctggtgcttc | 1380 | |
| acattctcct tcaagtgttc cttttctgtc tctgtgtctt cccagatcct ttctggtagc | 1440 | |
| ccttcatcct atcctctgtc ctcaccactt ttctaaatcc tcctccccta ggtggcacta | 1500 | |

```
cttttcctac catctctccc ttcaggaatc ctgtactatg tctacatggg gctgctggca   1560
gtgttctgta ccaatgccat caatatccta gcaggaatta atggcctaga ggctggccag   1620
tcactagtaa tttctgcttc catcattgtc ttcaacctgg tagagttgga aggtaggtgg   1680
gattgggggt ggggagagag aagtctgaat gttaaaggtg tggcctgata tatgactttg   1740
ggaaattcag ggaaaaaaag caatatgcgt agtaattata aagataagg gaggctactt    1800
actttgcaaa taatgcagat ttattgaaag tgagaaagaa aaatagcagc cgtgtcattt   1860
atagctggat tggcactaac agctaggcca tgatcttctc ccattgaata taaacaattt   1920
cacagaacct caacgttaca cagggtcatt ctgtgaccat gatggaggaa gaccaaaact   1980
cgacccctcc ctctataatc ctgtttgagc acagataaaa ccacaaaaac actgagcaac   2040
ccacaaaatg gccaagatcc tctctctctg ttaacgtgag ccatgagcga ctgctgcggc   2100
tttccaataa caactcagtt cctaccacct tttattttgt tttttgagac agggtctccc   2160
tctgtcaccc aggctggaga gcagtggcac gatcttagct cactgcatcc tctgactcaa   2220
acgatcctcc tgccccagac tcccaggtag ctggggctac aggcatgcgc caccacacct   2280
ggcaaatttt tgtattttt gtagagacag ggtttcacca cgttgcctag gctggtcttg    2340
aactcctggg ccgaagtgat tgtcagcct tggcctccca aagtgctggg attacactct    2400
tgagccactg tggccagcca gttcctacca cttcttagat aaacattaaa atgcttgatc   2460
agagaattat tgttgttttc ttttcttttt ctttttttt tttttttgag acggagtttc    2520
actcttgccc aggctggagt gcaatggtgc gatctcggct cactgcaacc tccacctccc   2580
aggttcaggc gattctcctg cctcagcctc cctagtagct gggattacag gcatgtgcca   2640
tcacgcccag ctagttttgt attttagta gagatgggat ttctccatgt tggtcaagct    2700
ggtctcaaac tccagacctc aggtgatccg cccacctcgg cctcccaaag tgctgggatt   2760
acaggtgtga gccaccgcac ccggccatga attacacctg cttctaaca gcacccaatc    2820
cagagcaaaa ctcttacttt cttttaccct ctcccaaaat acccaaaact gcaagccct    2880
cctaacactc tcttactgag acattccgtg gttcccaatg gtgtgtggtt tctgaagtct   2940
ccctttttac aacaagtcat taaacctagc ttcgaactat agatgtgttt ctagtggtct   3000
ttggctgatg gacatcaaca aatgtttatt aaagctaagt acttttaaa catgatcgta    3060
tttaaatctt gtaatggttt tatgtggcac atgttataat cagccctgtt ttacagatga   3120
gtaaacagat ttagagaagt taaatgtgtc atgatcaaga tcaaggtcac aaagctaaga   3180
agtaaagttg gtgtccaaac tgacatcaga atgggctaaa ccaaatttaa gacagtaact   3240
agtttggaag gctgcatgaa agaggtggaa tattgggaat tgccttgggt gacataaaag   3300
gggtattgag ttcttgaaag tgacttgggt gaggtggatg atacagctgt aaacagaact   3360
tagacaaaaa taggaccatg gtatgcagaa gaagtgggta ttaatttcc cttctttctt    3420
ccttgcttcc aaaggtgatt gtcgggatga tcatgtcttt tccctctact tcatgatacc   3480
ctttttttc accactttgg gattgctgta ccacaactgg taagtaggcc tatggataag    3540
gggaaaaggg gaaaactacc cgaacacatg gcaaagatgg cccttatcat aacccacctt   3600
gtggtggaga ggtaaaacct gtgcataact ccatggaatt ttctgtgtct tcagttggtc   3660
gtattctgaa atttctccct acccaacagt atttggggat gagtgcgtgg aggtcccagg   3720
aatagatgaa ttcagggcct tggatcctgc agagttgctg cacaactgga gtctcctcta   3780
agtcagaact agggtcaggg ctagtacagt gcccataggg tgtgatgtga gagaaaggat   3840
tggtaatgcc tcttgccact ggctcggatc ctctccccca cacaggtacc catcacgggt   3900
```

```
gtttgtggga gacaccttct gttactttgc tggcatgacc tttgccgtgg tgggcatctt   3960
gggacacttc agcaagacca tgctactatt cttcatgccc caggtgttca acttcctcta   4020
ctcactgcct cagctcctgc atatcatccc ctgccctcgc caccgcatac ccaggtagcc   4080
gctttggggc ttgaaatgga catcatagcc ttttcacttg ggatatctaa tgccagcctt   4140
tacattgctg tgcaaaggga gtgggcccaa agaagggcta tttccatgtg agtaaccctt   4200
tataacttcc aaagcacatt tatttgcatc atctgatact cacagtggtt ctgataacag   4260
caagcagcag agccagaaat agatctcagg ttgactccac attcaatgct cttcctattg   4320
attagccaca gggaggaggg ttcaaatagt ggcccagtca catgaagctg tcttcccccc   4380
gcagactcaa tatcaagaca ggcaaactgg agatgagcta ttccaagttc aagaccaaga   4440
gcctctcttt cttgggcacc tttatttttaa aggtaacagg gtaacaagga ggtaaggccc   4500
taggctgcca tcctgacctt gaggaatggg gaacctaggc ctacatcaga tccaagggga   4560
acttggaagc attaaataga tccacattcc taaagcatag gtattagctg aggttctctt   4620
cacctctggt ccctccaggt ggcagagagc ctccggctgg tgacaataca ccaaagtgat   4680
actgaggatg tgaattcac tgaatgtaac aacatgaccc tcatcaactt gctacttaaa   4740
atctttgggc ccatacatga gagaaacctc acattgctcc tgctgctgct gcaggtgagg   4800
atggggattg ggtttatacc tccttgtctc ccttttctccg tgattcttat tccagtccat   4860
ttctccttgc agatcctggg cagtgccttc accttctcca ttcgatatca gctcgttcga   4920
ctcttctatg atgtctgagt cccttgatca ttgtccttta cctcacagtc tctaggattc   4980
ctgactcagg ctgacctctc tctggtccca gactgcctcc ttgcccaggc ctctctcact   5040
cttcatactc ttccagattt tgttctcagc atttttcttt ccctgtgatc actggcatcc   5100
tgggcgtttc ttgcccccta ctgtctactg attggatttt acttatgact ttctgcaact   5160
tgctactctc cctctccatc ctgtctttgc agcctcacag ggtgggatac agaagttttt   5220
tttttgcagt tatccacagt cacatttcag agtcctgact ctcaaggaac tactggtttt   5280
tgggatagaa cttgggccag ggctagggac acaggctcca cagtgacctg ttatttgatt   5340
gtaaattaag tgttctgatt agtaagaagt aagcagggggg ccacatgctc tcaatggaga   5400
caataaagtg ttgtctattt ctta                                           5424
```

<210> SEQ ID NO 15
<211> LENGTH: 5894
<212> TYPE: DNA
<213> ORGANISM: Pan troglodytes
<220> FEATURE:
<221> NAME/KEY: misc_feature
<222> LOCATION: (3408)..(3408)
<223> OTHER INFORMATION: n is a, c, g, or t

<400> SEQUENCE: 15

```
aaaccgtagc tgcgtttccg ggaactgagt tgtgtttacc ttggcttccg actatgttgg     60
caacaggttt cctgcaagaa actggcgcgt ctccacaccc tcgtccctcc tccccacccc    120
ctgcctttca atagccatct tcctggagcc ggaggcatcc cagattaagg gagaggtacg    180
ggccctttaa gcttgaccta tggaggcgga cggagctaaa actgacgtgg aaccggaatg    240
tgagcggtgt cagacacgtg gtacaaggag gcattcatct tggaaccggg caattggcat    300
ttccgctctg ggtagtacat ctttaacata atgttaggga agtatccgtt cttggctgcc    360
tttctttaat tgcgtttcca gtactctctc ggtgattcta ctcttgaaca taggatgaaa    420
```

```
tttggaatca cacttctctt gcacttccat ccccaccctc taatgcccat attaaaaatg    480
gcggccgccg ccttccgcag taatggttgt tcagcgaaca agatccgggc ggaaacagta    540
gataggcggg tgcagcgggg cagaacatag gttgccttag agaggttctc cggtgtctcg    600
agggcggctc aagttagagt tgttgggttt tgctcagatt ggtgtgggaa gagcctgcct    660
gtggggagcg gccactccat actgctgagg cctcaggact gctgctcagc ttgcccgtta    720
cctgaagagg cggcggagcc gggcccctga ccggtcacca tgtgggcctt ctcggaattg    780
cccatgccgc tgctgatcaa tttgatcgtc tcgctgctgg gatttgtggc cacagtcacc    840
ctcatcccgg ccttccgggg ccacttcatt gctgcgcgcc tctgtggtca ggacctcaac    900
aaaaccagcc gacagcagat gtgagcagcg gcacacgggt ctgggcaggg ggcaagggct    960
aaggaaggag tggctagggc aggggcgggg accgggtgc ttgaccacac gtgaagactc    1020
agaactaacc caggcagcct ggaactcgga gaggtgatga gcagaactta ctcgcattgg    1080
ggaaggatg ggtagggacc cttgggtata tctgggactc tggcagtggt gctttcctcc    1140
ctccgccccc ctcaccactt accagaataa aaaaccggga atgagaagac cactttgggt    1200
tattgtaaca cctgcactag tgagtgacca cgcccccttt gctcttcccc ctcgcccct    1260
tgctgctggg ccacagccca gaatcccagg gagtgatcag cggtgctgtt ttccttatca    1320
tcctcttctg cttcatccct ttcccccttcc tgaactgctt tgtgaaggag cagtgtaagg    1380
cattcccca ccatgaagta agtgggtcg tgggggtgat gcctgtggc tgggacctgg    1440
gaggtacctg agagaattgg ggttatttgg gcttgtgggg agggctaag aaattatcag    1500
aaaagacagg aattcttaaa aggtggaatg ggagcaggct tgagtcatgg acctgcccga    1560
gccccccccca gtttgtggcc ctgataggtg ccctccttgc catctgctgc atgatcttcc    1620
tgggctttgc ggatgatgta ctgaatctgc gctggcgcca taaactgctg ctacctacag    1680
ctgcctcact acctctcctc atggtctatt tcaccaactt tggcaacacg accattgtgg    1740
tgcccaagcc cttccgcccg atacttggcc tgcatctgga cttgggtagg tagtcctacc    1800
actgctgccc ctatggcacc tacttcaggg aacccttcct ggtgctccac attctcctcc    1860
aagtgttcct tttctgtctc tgtgtcttcc cagatccttt ctggtagccc ttcatcctat    1920
cgtccgtcct caccacttt ctaaaaattc ttaaatcctc ctccctagg tggcactact    1980
tcttttccta ccatttctcc ccgcaggaat cctgtactat gtctacatgg ggctgctggc    2040
agtgttctgt accaatgcca tcaatatcct agcaggaatt aacggcctag aggctggcca    2100
gtcactagtc atttctgctt ccatcattgt cttcaacctg gtagagttgg aaggtaggtg    2160
ggattgggggg tggggagaga gaagtctgag cattaaaggt gtggcctgat atatgacttt    2220
gggaaattca gggaaaaaaa gcaatatgtg tagtaattat agaagataag ggaagctact    2280
tactttgcaa ataacaatgc agatttatta aaagtgagaa agaaaaatag cagccctgtc    2340
atttatagct ggattggcac taatagctag gccatgatct tctcccattg aatataaaca    2400
gtttcacaga accccaacgt tacacagggt cattctgtga ccatgatgga gcaagactaa    2460
aactagaccc ctccctctgt aatcatgttt gagcacaggc aaaaccacaa gaacactgag    2520
caacccacaa aatggccaag atccctctc tcggctaaca tgagcgactg ctgctgctct    2580
ccaataacaa ctcagttcct accacttctt ttttttttt ttgagacagg gtctccctct    2640
gtcatgcagg ctggagagca gtggcgcaat cttagctcac tgcatcctct gactcaaacg    2700
atcctcctgc cccagcctcc caagtagctg ggctacagg catgtgccac cacacctggc    2760
aaatttttgt atttttttgta gagacagggt ttcaccatgt tccctaggct ggtcttgaac    2820
```

```
tcctggactc aagtgatctg ccaggcctcc caaagtgctg ggattcactc ttgagccact    2880
gtgcccagcc agttcctacc atttcttaaa taaacattaa aatgcttgat catagaatta    2940
ctcttgcttt cttttctttt cttttctttt tttttgaga cggagttttg ttcttgccca    3000
ggccggagta caatggtgcg atctcggctc accgcaacct ccgcctccca ggttcaagcg    3060
attctcctgc ctcagcctcc ctagtagctg ggattacagg cacgtgccac cacgcccagc    3120
taattttgta tttctagtag agacggggtt tctccatgtt ggtcaggctg gtctcgaact    3180
cctgacctca ggtgatctgc ctgcttcagc ctcccaaagt gctgggatta caggcgtgag    3240
tcaccgcacc cggccatgaa ttactcctgc tttctaacag cacccagtcc agagcaaaac    3300
tactttcttt caccctctcc caaaataccc aaaacaaacg ctactacaag cccctcctaa    3360
caccctctta ctgagacatt ccgtggttcc caatggtgtg tggtttcnga agtctcccct    3420
tttacaacaa gtcattaaac ctagctttga gctatagatg tgtttctgat ggtcttggct    3480
gatgaacatc aacaagtgtt tattaaagct aagtactttt taaacactat cttatttaaa    3540
tcttgtaatg gttttatgtg gcagatgtta taatcagccc tgttttacag atgagaaaac    3600
aggcttagag aagtcaaatg tgtcatgatc aagatgaagg tcacaaagct aagaagtaaa    3660
gttggtatcc aaacttacat cagaatgggc taaaccaaat ttaagatagt aactagtttg    3720
gaaggctgca cgaaagaggt ggaatattgg gaattgcctt gggtgacata aaaggagtat    3780
tgagttctta aaagtgactt gggtgaggtg gatgataaca gctgtaaaca gaacttagac    3840
aaaaatagga ccaaggtttg cagaggaagt gggtattaac ttttccttct ttcttccttg    3900
cttccaaagg tgattgtcgg gatgatcatg tcttttccct ctacttcatg atacccttt     3960 ttttcaccac tttgggattg ctctaccaca actggtaagt aggcctgtgg ataaggggac    4020
aactacctga acacatggca aagatggccc ttatcataac ccaccttgtg gtggtgaagc    4080
taaacctgcg catacctcta tggagttttc tgcgtcttca gttggtagta ttctgaaatt    4140
tctctctacc cagtagtagt tagggatgag tgcgtggagg ccccaggaat agttgaattc    4200
agggccttgg atcctgcaga gttgctgcac aactggagtc tcctctgagt cagaactagg    4260
gtcagggcta gtccagtgcc catagggtgt gatgtgagag aagggattgg taatgcctct    4320
tgccactggc tcggatcctc ttcccccaca caggtaccca tcacgggtgt tgtgggaga    4380 taccttctgt tactttgctg gcatgacctt tgccgtggtg ggcatcttgg gacacttcag    4440
caagaccatg ctactattct tcatgcccca ggtgttcaac ttcctctact cactgcctca    4500
gctcctgcat atcatcccct gccctcgcca ccgcataccc aggtagccgc tttgggcttt    4560
gaaatggaca tcatagcctt ttcacttggg atatctaatg ccagcctata catttgctgt    4620
gcaaagggag tgggcccaaa gaagggctat ttccatgtga gtagcccttt ataacttaca    4680
aagcacattt atttgcataa tctgctacag tggttctgat aacagtaagc agcagagcca    4740
gaaatagatc tcaggttgac tccacattca atgctcttcc tattagccac agggaggagg    4800
gttcaaatag tggcccagtc acatgaagct atcttccccc cgcagactca atatcaagac    4860
aggcaaactg gagatgagct attccaagtt caagaccaag agcctctctt tcttgggcac    4920 ctttattta aaggtaacag ggtaacaagg aggtaaggcc ctaggctgcc atcctgacct    4980
tgaggaatgg ggaacctagt cctacatcag atccaagggg aacttgaaag cattaaatag    5040
atccacattc ctaaagcata ggtattagct gaggttctct tcacctctgg tccctccagg    5100
tggcagagag cctccagctg gtgacagtac accagagtga gactgaagat ggtgaattca    5160
```

```
ctgaatgtaa caacatgacc ctcatcaact tgctacttaa aatccttggg cccatacatg      5220
agagaaacct cacattgctc ctgctgctgc tgcaggtgag gatgggaatc gagtttatac      5280
ctccgtgtct ccctttctgc gtgattctta ctccagtcca tttctccttg cagatcctgg      5340
gcagtgccat caccttctcc attcgatatc agctcgttcg actcttctat gatgtctgag      5400
tcccttgatc attgtccttt acctcacagt ctctaggatt cctgactcag gctgacctct      5460
ctctctggtc ccagactgcc tcttgccca ggcctctctc actcttcata ctcctccaga      5520
ttttgttctc agcattttcc tttctctgtg atcattggca tcctgggcgt tcttgccct      5580 ctactgacta ctgattggat tttacctatg gctttctgcg acttgctact ctctccctct      5640
ccatcccatc tttgcagcct catagggtgg gatacagcag ctttttttgc agttatccac      5700
actcacattt cagagtcctg actctcaagg aaccactggt ttttgggata gaacttgggc      5760
cagggctagg aacacaggct ccacggtgac atgtcatttg attgtaaatt aagtgttctg      5820
attagtaaga actaagcagg gggccacatg ctctcaatgg agacaataaa gtgttgtctt      5880
tttcttattg ttta                                                        5894

<210> SEQ ID NO 16
<211> LENGTH: 4557
<212> TYPE: DNA
<213> ORGANISM: Canis familiaris

<400> SEQUENCE: 16
gtgaggaggc aagtgcggcg ggggacagcc gagggtgcgc gctggaggct cgcgggagtc        60
ctgggggcgc ctcaattcag agttgggttt tgctcaggcc gctgtgggag gatccagcct       120
gtgccgagcg gctgctcctc cccgcggggg gctccgggct accgcccagc tcgcccatta       180
gccgaggcgc cggcagagcg gggccccctgg ctggtcatca tgtgggcctt ccggagttg       240 ccgatgccgc tgctggtgaa tttggtcggc tcgctgctgg gatttgtggc cacggtcacc       300
ctcatccccg ccttccgtgg ccacttcatc gccgcgcacc tctgtggcca ggacctcaac       360
aaaaccggcc ggcagcagat gtgagcggtg gcacccgggt ccggggaggg ggccggcagg       420
gcaagggcgg gacctggggt gcctgaccc gcggacacgc agcgctaacc ccgcagacag       480
ctgcgggctc tgggagacga agggcagcgc tggccaactc tgggaaggga tgttgcagta       540
caggggaccc tcgggtgtat cagggactcc agcgctggtg cccttccacc ccccttcccc       600
gtagatcgct gtaatgcttg ctctagtgag tgaccacgcc ccctctcctc tccccgccc       660 cctccctttg ctgctgggcc acagcccaga gtcccaggga gtgatcagcg gtgctgtttt       720
ccttatcatc ctcttctgct tcatcccttt cccttcctg aactgtttta tggaggagca       780
gtgtaaagcc ttcccccatc acgaagtaag tgggtgagtt ggggcggtt gcttgggct       840 ggggcctggg agctacctgg gagagttgtg gttattaggg tttggtgga ggggctgagg       900 aaggagcgaa gagacgggtg ttttgcaag atgatgtggg cataggcttg agcggtgacc       960
tgcccgagcc tcccccagtt cgtggccctg ataggtgcgc tccttgccat ctgctgcatg      1020
attttcctgg gctttgcgga cgatgtactg aatctgcgct ggcgccacaa gctgctgctg      1080
cctacagctg cctcgctacc tcttcttatg gtctatttca ccaactttgg caacacgacc      1140
attgtggtgc ccaagccttt ccggccgatt cttggcctgc atctggactt gggtgagtag      1200
ccctgtgact gacgtccctg tggcccttac tttgggcac ccttaccctg ggagataatc      1260
tagcagagca tcattcctgg tgctccagat cctcttccaa gtgtcccat cttgttcctg      1320 tgtcttctca gatccgttct gttggtcctt cgtccaatcc tctgtcctca ccacttttct      1380
```

```
cagaagaata ttcttaagtc ctcatttcta tggatggcac acttcttact ctcttcttcc    1440
cccagggatc ctgtattatg tttacatggg gctgctggca gtgttctgta ccaatgccat    1500
caatatccta gcaggaatta atggcctaga ggcaggccag tcgctagtta tttctgcttc    1560
catcatcgtc ttcaatctgg tggagctgga aggtaggtga gagtgggagt ctgagtatta    1620
aggaaactgc ctgatacctg gctttgggga attcaggaaa aaataaaagc aatatattaa    1680
gattaaatgt aaagaaaaac agctctgtca ttgacagctg aattggcact aataggtagg    1740
ccatggtctt ctgctgaaca taaacaattt cacagaactt cacaatcaga cgaggtcact    1800
ctatgtccat gatagagtaa agcaaaccca gattcctcca taaacatgtc tgagtatagc    1860
cagaactgca ttttgtgcat cccacaaaaa tgactaggat ctccctcttc tggctaaggt    1920
gagcaattgc ttccttctga taacttggtt ctacttagag aaaactaaga tgctcataga    1980
attacttcca ctgacagcac ccagtcttgg gcaaaacttt gcctccttcc tttctccccc    2040
aaattactca aaacaatcct ataacacatc ttcctaatac ttccctactg aggcatcccc    2100
tggttaccta tggtgcgtgg tctacagtgt ctctcttgtt acacgtcagt aaacccagct    2160
ttgactgcag gtgtgtttct ggtggtcttt ggctgatgga tatcagtgct tattaaaaca    2220
aaatactctt aaagcattta aactttgtaa tgtggcaagt gttctcatga accatatttt    2280
acagttgagg aaacagaggg cgagagaatt taagtgtgtc atgatcaagg tcacacagtt    2340
agaaagtaaa gctagtattc aaacctgggc tgaatgatct aaaccaaatt gaagacagca    2400
acttgtatta ggaagggttc atgaatgagg tggaatatta ggaattgcct gagtgacaca    2460
aaagaagtag tgagttctgg aatgggactt ggaagaggtg gaaagtacag ctggggacag    2520
aacttgagac agaaatagga cccagttatg caggggaag tacctttca actcatcctt    2580 cttctttttt cttcttcccc tgcttccaaa ggtgattatc gggatgatca cgtcttttcc    2640
ctctacttta tgataccctt tttttccacc accttgggat tgctctacca taactggtaa    2700
gtgggccatg tgaacatgta gcaagtatgg tcctgttggt cctgacccaa ctcctgttgg    2760
agaggctaag cctgcgcaca cctgtattga gtgttttctg gatgcctagt tggtaatatt    2820
cttcaattac tctctaccca gttgcagtta gagacaagtg ctgtggagcc cccaagaaga    2880
gatgaattca gggctttggg ttctggaggc ttgttggaag atctggagtt cctccgggc    2940 caggactaga gtcagggcta gtccagggtt cagggcgtgt aatatgagag aaaagactga    3000
tagtgcctcc tgccactggc tcagatcctc tcccccacac aggtacccat cacaggtgtt    3060
tgtgggagat accttctgtt actttgctgg catgaccttt gccgtggtgg gcatcttggg    3120
acacttcagc aagaccatgc tactcttctt catgccccag gtgttcaact tcctctactc    3180
actgcctcag ctcctgcata tcatacccctg ccctcgccac cgcattccca ggtagccact    3240
ttggggctta aaagggacat cttagctttt tcacttggga tgcataaagc cagccttctg    3300
catctgctgt gtaagggaaa tgggcccaaa ggagggctct ttccgtgcaa ttagcccta    3360 taaatgacag agcacattca cccacataat ctgatcagct ctgatcacac agtggtaagc    3420
agagccggaa acagatcttc aggttgtctg attccacttt cggtactctt cctattaatt    3480
gaccgcagtg tggagagttc ttggagtagt ggcccagtca cataaagctc tcttcccct    3540 gcagactcaa taccaagaca ggcaaactgg agatgagcta ttccaagttc aagaccaaga    3600
gcctctcttt cttgggcaac tttattctaa aggtaacagg gtaacgaggt aaggctctag    3660
gccaccatcc ggaattcagg gcctggggac cctcggcttg catcagatcc aaggggagcc    3720
```

| | |
|---|---|
| tggaagcatg aagcagatcc cccattgctg aagcagagtt gaagttctct ccacctctgg | 3780 |
| cccctccagg tagcagcgag cctgcagcta gtgacagtgc accagagtga gaatgaggat | 3840 |
| ggtgccttca cggagtgtaa caacatgacg ctcctcaact tgctccttaa ggttctcggg | 3900 |
| cccatgcatg agagaaacct gactctgctc ctgctgctgc tccaggtgtg gtcagggaag | 3960 |
| ggctttgctg gctctggtct ccctttctcc atggctctga ctctggtgtg tttctttctc | 4020 |
| ctcacagatc cttggcagtg ctgtcacctt tccatccgg taccagcttg tccggctctt | 4080 |
| ctacgatgtc tgagtccccc aatccttgcc cttcactgca tagtctgcag ggttcctgac | 4140 |
| tcaggcctgc ctctttctgg gccaggcacg cttccgggcc caggcctctc tcacctctta | 4200 |
| cttttctcca gattttgtac ttagcgattc cgttccgctg tgatcgacat cctgggcctg | 4260 |
| tcttgccctg tactgactgt tgattggact ttgcctgtgg cttcttcaa cttgctgctc | 4320 |
| tccctctcta tcccatccct gcggcctccc aaagtgggat actgtgcttt ttatgcagtt | 4380 |
| atccaccact cggactctcg aggaatatgt tgggcctggg gatagaaccc tggctgggga | 4440 |
| gagggacaca ggctcgaaga tcacttgatt atttgaccat aaattaagta ttctgattcg | 4500 |
| taagagcaga ttgggggggcc aggtgctccc agtggtgaca ataaagtgtt gtctttt | 4557 |

<210> SEQ ID NO 17
<211> LENGTH: 5374
<212> TYPE: DNA
<213> ORGANISM: Cricetulus griseus

<400> SEQUENCE: 17

| | |
|---|---|
| caaggcagag cctaggttgc tttataaaac ctcttgggga agcccgaggg cggttcaaat | 60 |
| taagagttgt tgggttttgc cccgcctcgc atgtgaggag cggacactgc tcacggctga | 120 |
| gacctcgggg ctgcttccca ccagttagct gagaaggctg cggagctgga acctctggcc | 180 |
| actcgccatg tgggccttct ctgaggtacc gattccgctg ctggtgaatt tgatcggctc | 240 |
| gctgctggga tttgtggcca cgctcaccct catcccggcc tttcgtggcc actttatcgc | 300 |
| tgcgcgcctc tgtggccagg acctcaacaa aaccaaccgg cagcagatgt gagcagtggc | 360 |
| acacgggtgt cccgggcagg ggccaggggt gggcaaggca caggcgagct ctgaggtgct | 420 |
| taaatgtgcg tacgaaccaa atctaactgg agttgtccgg gaccctggga ctcgatggcc | 480 |
| agaagtgggtt agcactgggg aatgctaagg aaggggaccc ttgagtgaga acatccagcg | 540 |
| gcgcctgcct ccccccgccc cccactgccc tcccgctcca ctgctccccc gcctcactcc | 600 |
| tgggaagatc ttttgggtca catggttttt gcactaacca cgcccatttc ttcttccttc | 660 |
| tccacccct tgctgcgggg ccacagccca gaatcccagg gagtgatcag cggtgccgtt | 720 |
| ttccttatca tcctgttctg cttcatcccc ttccccttct tgaactgctt tgtgaaggag | 780 |
| cagtgtaagg ctttcccca ccatgaagta agtgggttcg tgggggcggt tgcctgggc | 840 |
| ctggagggtt cccgagagag ttggggttgt gtggatttga ggaggaggga ctgaggacct | 900 |
| agtggaaaag acagaaattt ttgaaagctt gaatggcagt aggcttgagt catgacctgc | 960 |
| ccgagcctcc cccagtttgt ggccctcata ggtgcccttc ttgccatctg ctgcatgatt | 1020 |
| ttcttgggct tcgcggacga tgtcctgaat ctacgctggc gccataagct gctgctgccc | 1080 |
| acagctgcat cactacctct tcttatggtc tattttacca actttggcaa cacaaccatt | 1140 |
| gtggtaccca agcccttccg cccagttctt ggcttgcatc tggatttggg tgagtatccc | 1200 |
| tgctgctaca gccctgtgg cacttatttc aagtcaccct cccccaaag gtgcccagca | 1260 |
| gagcaccctt cttgatgttc cacactcccc tgttttgtt ccgtccctgt gaatgctcag | 1320 |

```
gttctctctt gtgccctgtc attgtgtgtt ctgttttcag aataccgtta gatcctttcc    1380
tagctgtcac tgcttttat actatgtctt gcagggatcc tgtactatgt ctacatgggg    1440
ctcctggcag tgttctgtac caatgccatc aatatcctag caggaattaa cggcctagag    1500
gccggccagt cattggtcat ctctgcttcc atcattgtct tcaacctggt ggagctgcaa    1560
ggttggtggg aagagagaga tctcagtgtt cagagaattg cctgatatat agctttgaga    1620
aaagggggc ttatagaaga tagggaaagc tatttacttt gcaaataaca atgaagagtt    1680
acttgagtag gaggaagaaa aatagcagtc tgtcatttat agctggattg gcatgagtag    1740
ctagaccatg actgtttcct attggacata aatagtttca tagaaccca gcatgagaga    1800
ggggcgccct gaccgtggtg aaacaagaca gaaaccagac ttctcccact gtaatcatgt    1860
ctgaacaccg acaaaagcac aggaacaaag tcagcccaaa catcccttct tgtctaatgt    1920
gagagggtat agcttctttg cagtaacaac tcagttcctg ctacttctta agttgttcag    1980
tcagaaaatt acttctgctt tctgacatca ggcagtccag agcacaactt ttccttgcag    2040
cctccccaga accacttaaa gtgaatccta ttgtaagtcc cttctaacaa cctttagagt    2100
acctgcccag catgaggcct tgggtacagt ccccagtatc tctgtttgca tgcatgtaca    2160
catacccaca tgcacacact gaacttactt attgaaggta agcaatattt atttgcattt    2220
tttgtgtgtg tgacaaaatt tcactatgta attcagaata gccttgaatt cactatgtag    2280
cctaggccgt cctcgaactt acagtgataa tcctgcctca gcttcctaag tgctaagatt    2340
caaggtatgc actaccaggc cagctaagaa agcaattttt aaactaggta tggtggcaca    2400
catcactaat tctaacactc tgggagactt gggcaggaag atcatgagtt tgagctcagc    2460
ctgggcactt ggtaagtctc tgtttctaga aataaaacat ggagtggtga tacacacctg    2520
taatcccagc attcatgagg ctgggcagg aggatcacca caaggtcaag acctgcctgg    2580
gttacataag caagttcaag gccagcgtga actacgtagt gagaccctgc ctcaaacaaa    2640
caaataaata aataaacatg atcctgagtt tggttcccag tactcccccc aataaatgaa    2700
atgaaatgaa agagctgggg aggcagctta gtgctaaggt ccaggacccc atgtgaaggc    2760
agctgcgtgt atgtgttatc agccctgttt catacactag ataataaaac tggttttcaa    2820
acttaagtca gcatgtctgg acaaagtgaa gactttaact tgttttttgac ggtttcatga    2880
cagtagtgag ctattgggaa ctgcctgggt accatcaaag gaataatgag gggctgggga    2940
tttagctcag cggcataagc gcctgccttg caagcaggca gtcatgagtt tgatccccgg    3000
taccgataaa aaggaaaaag acaaaaaaaa aaggaataat gagttttga aggtggctcg    3060
ggtgagggga ggtggcaaca gagacaggga tgcgacagac aaaatgaaga gcagggaca    3120
taggggagat gggtgttcac ttttccttct ttgtcctttg tttcccaagg tgattaccgg    3180
gatgatcatg tcttttccct ctacttcatg ataccgtttt ttttcaccac cttgggattg    3240
ctgtatcata actggtaagg aggctgtggc tcagggaaaa ggaaaacaac taactggtca    3300
ttggacaaag atggtcctga tcttaaccca gctcctgaaa gacaggctga acttgcgcat    3360
acttttgctc agtgttttct gggtattcag ttggtggatt gcctcccccc gccccgtttt    3420
tttttgaga cacctgtggc ctctcgagtg ctaggccagt gctttactac tgagtcttgc    3480
cctctagtat tctcaggttt gttctttcct cagcagttgg agacaagtgc tatggagccc    3540
caggaataat tatggggact tgcgttctgc agacttgcta gaccctcctg tccgaactag    3600
gatcagggga gcatgtgtgg tggctcacac ctgtaatccc agcactcagg agactgaggc    3660
```

```
aggaggatta ccatgagatc gagggcaccc tcagctcaca tagtgactt  gaggccagcc    3720 tggactacat agcgagactc ttgtctccaa aagaaaaaaa aagaaagaat aaaagaacag    3780
gggtctgagt tcgtccagta cctagcctgt gtgatgtgag agaaaagact gtgatgcctc    3840
ttggcactgg cttggatcct ttcccccaca caggtaccca tctcaggtgt ttgtgggaga    3900
caccttctgt tactttgctg gcatgacctt tgccgtggta ggcatcttgg gacacttcag    3960
caagaccatg ctgctcttct tcatgccaca ggtgttcaac ttcctctact cgctgcctca    4020
gctcctgcat atcatcccct gtcctcgcca ccgtataccc aggtagctgt ttgggggctg    4080
gaaagccttt ctactgggat gtctaacacc aggctctaca tttgctgtgc aaagaatgtg    4140
ggcccatagg aaggctaact ttttcatgt  aggtggccct ttaagtttac acagcacgtt    4200
tacttccata atctcattta atactcacag tagttctgat catagagtag taagcagcag    4260
agccagaaat agatctcact ccatgatcag tgtttttctt agtcattaac ggaagaaagt    4320 ttttgagta  gtgacccagt cacacgaagc tgtctttccc ctacagactc aataccaaga    4380
caggcaaact ggagatgagc tattccaagt tcaagaccaa cagcctttct ttcttgggca    4440
cctttatttt aaaggtaaca aggtaacgag gaggtaaggc cccaggccac catcctgaac    4500
ttgggacatg ggggacccag gcctacatta gatctagagg gagcttggaa gcattaagca    4560
gagccctgtt cctgacatac aggtattggc tgaagttttt ctgtctgtct ctggtctctc    4620
taggtagcag agagactcca gctagtgaca gtgcaccgga gtgagggtga ggacggggcc    4680
ttcactgagt gtaacaacat gaccctcatc aacttgctgc ttaaaatctt tgggcccata    4740
catgagagga acctcacatt gctcttgctg ctgctacagg tgagcctggg gtgagtttgt    4800
gcctcctcat gtccttttct ctatggttct tattctagtc catttctcct tgcagatcgt    4860
gggcagtgct gtcaccttct ccattcgata ccagcttgtc cgactcttct atgacgtttg    4920
agttcctgaa gattgccctc tgccacactg tctccagggg tcctgctcag gccagccagt    4980
ctggttctgt gggcctctcc caatcttcag tctccttcag atttattccc agcattttc     5040 ataacctatg attatcaaca tcctgagcca tttttgccct ccagcaacta ctaactggac    5100
tttgcctatg gcctccttca acttgccact ctccctaccc atcacagcca gaggcttgat    5160
gtagcagctt ttatgcagat atccacaact cagctttcag agtcctcact ctcaaagaac    5220
atgctgggcc ttgagataga acctgagcta gggctaggga cactggtgca agggtgattt    5280
gatatttgat tataaattaa gtgttctgat tagtaagaca gaaggggagc ctggtgctcc    5340
caacggtgac aataaagtgt taccttttc  ttgt                                5374
```